(12) United States Patent
Monnet et al.

(10) Patent No.: US 10,689,441 B2
(45) Date of Patent: *Jun. 23, 2020

(54) ANTI—TLR4 ANTIBODIES AND METHODS OF USE THEREOF

(71) Applicant: NovImmune S.A., Geneva (CH)

(72) Inventors: Emmanuel Monnet, Geneva (CH); Limin Shang, Geneva (CH); Susana Salgado-Pires, Geneva (CH); Walter Ferlin, Saint Cergues (FR); Greg Elson, Collonges sous Saleve (FR)

(73) Assignee: NovImmune SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,112

(22) Filed: Dec. 8, 2014

(65) Prior Publication Data

US 2015/0158946 A1    Jun. 11, 2015

Related U.S. Application Data

(60) Provisional application No. 61/912,617, filed on Dec. 6, 2013.

(51) Int. Cl.
| | |
|---|---|
| *A61K 39/395* | (2006.01) |
| *A61K 39/00* | (2006.01) |
| *C07K 16/28* | (2006.01) |
| *A61K 35/28* | (2015.01) |
| *A61K 45/06* | (2006.01) |

(52) U.S. Cl.
CPC .............. *C07K 16/28* (2013.01); *A61K 35/28* (2013.01); *A61K 39/3955* (2013.01); *A61K 45/06* (2013.01); *C07K 16/2896* (2013.01); *A61K 2039/505* (2013.01); *C07K 2317/30* (2013.01); *C07K 2317/33* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,522,811 A | 6/1985 | Eppstein et al. | |
| 5,151,510 A | 9/1992 | Stec | |
| 7,312,320 B2 | 12/2007 | Elson | |
| 7,348,316 B2 * | 3/2008 | Rossignol | A61K 31/70 514/53 |
| 2008/0050366 A1 | 2/2008 | Elson et al. | |
| 2012/0142098 A1 * | 6/2012 | Elson | C07K 16/28 435/375 |
| 2012/0177648 A1 * | 7/2012 | Kosco-Vilbois | C07K 16/28 424/135.1 |

FOREIGN PATENT DOCUMENTS

| | | |
|---|---|---|
| WO | WO 03/106692 A2 | 12/2003 |
| WO | WO 2005/065015 A2 | 7/2005 |
| WO | WO 2005/117975 A2 | 12/2005 |
| WO | WO 2007/110678 A2 | 10/2007 |
| WO | WO 2009/101479 A2 | 8/2009 |
| WO | WO 2009/138494 A2 | 11/2009 |
| WO | WO 2013/149111 A2 | 10/2013 |

OTHER PUBLICATIONS

Goldberg et al, FASEB J. 2007, vol. 21, pp. 2840-2848.*
Zhao et al., Cell Mol Immunol. Mar. 2013; 10(2): 165-175.*
Dunn-Siegrist et al., (Journal of Biological Chemistry, 2007, vol. 282, No. 48, pp. 34817-34827.*
Baldrick P. "Pharmaceutical excipient development: the need for preclinical guidance." Regul. Toxicol Pharmacol. 32(2):2 W-8 (2000).
Bowie et al. "A Method to Identify Protein Sequences That Fold into a Known Three-Dimensional Stucture", 1991, Science, vol. 253, p. 164-171.
Charman WN "Lipids, lipophilic drugs, and oral drug delivery—some emerging concepts." J Pharm Sci. 89(8):967-78 (2000).
Daubeuf et al. "TLR4/MD-2 Monoclonal Antibody Therapy Affords Protection in Experimental Models of Septic Shock," J. Immunol., vol. 179, p. 6107-6114 (1997).
Davies et al. "Antibod-Antigen Complexes", Annual Rev Biochem vol. 59, p. 439-473 (1990).
Devetten M P et al. "Graft-versus-host disease: How to translate new insights into new therapeutic strategies", Biology of Blood and Marrow Transplantation, vol. 10, p. 815-825 (2004).
Di W., et al. "Relationship between TLR4 and acute graft-versus-host disease in murine haploidentical hematopoietic stem cell transplantation model", Acta Universitatis Medicinalis Nanjing Natural Science, vol. 33, No. 4, p. 462-466 (2013).
Fauchere, "Elements for the Rational Design of Peptide Drugs", Advances in Drug Research, vol. 15, p. 29-69 (1986).
Evans et al. "Design of Nonpeptidal Ligands for a Peptide Receptor: Cholecystokinin Antagonists", J. Med. Chem., vol. 30, p. 1229-1239 (1987).
LaPlanche et al. "Phosphorothioate-modified oligodeoxyribonucleotides. III. NMR and UV spectroscoptc studies of the $R_p$-$R_p$, $S_p$-$S_p$, and $R_p$-$S_p$ duplexes, [dCGG$_s$AATTCC)]$_2$, derived from diastereomeric 0-ethyl phosphorothioates", Nucleic Acids Research, vol. 14, No. 22, p. 9081-9093 (1986).
Lefranc, M-P., "Nomenclature of the Human Immunoglobulin Genes", Current Protocols in Immunology, supplement 40, A1.P.1-A.IP.37 (2000).

(Continued)

*Primary Examiner* — Daniel C Gamett
(74) *Attorney, Agent, or Firm* — Cooley LLP; Ivor R. Elrifi; Cynthia A. Kozakiewicz

(57) ABSTRACT

This invention relates generally to anti-Toll-like Receptor 4 (TLR4 antagonists) including antibodies that specifically bind Toll-like Receptor 4 (TLR-4), to methods of using the anti-TLR4 antagonists as therapeutics and to methods of using the anti-TLR4 antagonists for inhibiting, delaying the progression of, or otherwise ameliorating a symptom of Graft-versus-Host disease (GvHD) and/or improving survival of GvHD subjects and/or transplanted biological materials in subjects.

19 Claims, 1 Drawing Sheet
Specification includes a Sequence Listing.

(56) References Cited

OTHER PUBLICATIONS

Malmqvist, "Biospecific interaction analysis using biosensor technology", Nature, vol. 361, p. 186-187 (1993).
Marasco et al., "Design, intracellular expression, and activity of a human anti-human immunodeficiency virus type 1 gp120 single-chain antibody", Proc. Natl. Acad. Sci. USA, vol. 90, p. 7889-7893 (1993).
Needleman and Wunsch "A General Method Applicable to the Search for Similarities in the Amino Acid Sequence of Two Proteins", J. Mol. Biol., vol. 48, p. 443-453 (1970).
Nijhuis O. et al., "Endothelial Cells Are Main Producers of Interleukin 8 through Toll-Like Receptor 2 and 4 Signaling during Bacterial Infection in Leukopenic Cancer Patients", Clinical and Diagnostic Laboratory Immunology, vol. 10, No. 4, p. 558-563 (2003).
Pearson and Lipman "Improved tools for biological sequence comparison", Proc. Natl. Acad. Sci. USA, vol. 85, p. 2444-2448 (1988).
Pivarcsi et al., "expression and function of Toll-like receptor 2 and 4 in human keratinocytes", International Immunology, vol. 15, No. 6, p. 721-730 (2003).
Powell et al. "Compendium of excipients for parenteral formulations" PDA J Pharm Sci Technol. 52:238-311 (1998).
Rizo and Gierasch "Constrained Peptides: Models of Biocative Peptides and Protein Substructures", Ann. Rev. Biochem., vol. 61, p. 387-418 (1992).
Shimazu R. et al., "MD-2, a Molecule that Confers Lipopolysaccharide Responsiveness on Toll-like Receptor 4", J. Exp. Med., vol. 189, p. 1777-1782 (1999).
Sivula J. et al. "Toll-Like Receptor Gene Polymorphisms Confer Susceptibility to Graft-Versus-Host Disease in Allogenic Hematopoietic Stem Cell Transplantation", Scandinavian Journal of Immunology, vol. 76, pp. 336-341 (2012).
Smith an Waterman "Comparison of Biosequences", Advances in applied Mathematics, vol. 2, p. 482-489 (1981).
Stec et al. "Automated Solid-Phase Synthesis, Separation, and Stereochemistry of Phosphorothioate Analogues of Oligodeoxyribonucleotides", J. Am. Chem. Soc., vol. 106, No. 20, p. 6077-6079 (1984).
Stein et al. "Physicochemical properties of Phosphorothioate oligodeoxynucleotides", Nucl. Acids Res., vol. 16, No. 8, p. 3209-3221 (1988).
Thornton et al. "Prediction of progress at last", Nature, vol. 354, p. 105-106 (1991).
Uhlmann and Peyman "Antisense Oligonucleotides: A New Therapeutic Principle", Chemical Reviews, vol. 90, No. 4, p. 544-584 (1990).
Veber and Freidinger "The design of metabolically-stable peptide analogs", TINS, p. 392-396 (1985).
Wang W. "Lyophilization and development of solid protein pharmaceuticals." Int. J. Pharm. vol. 203, p. 1-60 (2000).
Zon et al. "Phosphorothioate oligonucleotides: chemistry, purification, analysis, scale-up and future directions", Anti Cancer Drug Design vol. 6, p. 539-568 (1991).
Zon et al. Oligonucleotides and Analogues: A Practical Approach, p. 87-108, (1991).
Gale, R.P. and Y. Reisner (Jun. 28, 1986) "Graft Rejection and Graft-Versus-Host Disease: Minor Images" The Lancet, 327(8496): 1468-1470.

* cited by examiner

ANTI—TLR4 ANTIBODIES AND METHODS OF USE THEREOF

RELATED APPLICATION

This application claims the benefit of U.S. Provisional Application No. 61/912,617, filed Dec. 6, 2013. The contents of this application are hereby incorporated by reference in their entirety.

INCORPORATION OF SEQUENCE LISTING

The contents of the text file named "NOV1034001US_SeqList.txt", which was created on Feb. 4, 2015 and is 159 KB in size, are hereby incorporated by reference in their entirety.

FIELD OF THE INVENTION

This invention relates generally to anti-Toll-like Receptor 4 (TLR4 antagonists) including antibodies that specifically bind Toll-like Receptor 4 (TLR-4), to methods of using the anti-TLR4 antagonists as therapeutics and to methods of using the anti-TLR4 antagonists in methods of treating, inhibiting, delaying the progression of, or otherwise ameliorating a symptom of Graft-versus-host disease (GvHD) in a subject and/or improving survival of stem cell-transplanted or bone marrow-transplanted subjects.

BACKGROUND OF THE INVENTION

Stem cell transplantation such as allogeneic hematopoietic stem cell transplantation (allo-HCT) and allo bone marrow transplantation (BMT) is a curative therapy for human blood-borne cancer. Unfortunately, donor immune cells may consider normal host tissues as non-self and initiate immune attack against those tissues, resulting in the phenomenon of GvHD. Although progress has been made in reducing GvHD after allo-HCT and allo-BMT, it remains a major complication and limits more widespread application of the therapies in hematologic malignancy. GvHD occurs when donor immune cells attacks the normal tissues of the recipient. Severe tissue damage and death are the consequences of the disease.

Thus, there remains a need for methods to prevent GvHD and improve survival of the allo-HCT or allo-BMT patients.

SUMMARY OF THE INVENTION

The invention provides methods of inhibiting, delaying the progression of, or otherwise ameliorating a symptom of Graft-versus-Host disease (GvHD) and/or improving survival of subjects who are receiving, have received and/or will be receiving transplanted biological materials, including for example, subjects who have received and/or are receiving a stem cell transplant, a bone marrow transplant or other stem cell-related transplant, using anti-Toll-like Receptor 4 (TLR4 antagonists) including antibodies that specifically bind Toll-like receptor 4 (TLR4). In some embodiments, the GvHD is acute. In some embodiments, the GvHD is chronic. In some embodiments, the GvHD is a subtype of GvHD and/or a disease that is associated with or otherwise considered a side effect of GvHD, such as by way of non-limiting example, idiopathic pneumonia syndrome (IPS), bronchiolitis obliterans (BOS), bronchiolitis obliterans organizing pneumonia (BOOP), acute pancreatitis, and/or acute hepatitis.

The invention provides methods of inhibiting, delaying the progression of, or otherwise ameliorating a symptom of GvHD and/or improving survival of stem cell-transplanted subjects, including bone marrow transplant subjects, by administering to the subject the anti-TLR4 antagonist. In some embodiments, the GvHD is acute. In some embodiments, the GvHD is chronic. In some embodiments, the GvHD is a subtype of GvHD and/or a disease that is associated with or otherwise considered a side effect of GvHD, such as by way of non-limiting example, IPS, BOS, BOOP, acute pancreatitis, and/or acute hepatitis. In some embodiments, the anti-TLR4 antagonist is or is derived from an antibody or immunologically active fragment thereof that binds TLR4. In some embodiments, the anti-TLR4 antagonist is a peptide-based antagonist. In some embodiments, the anti-TLR4 antagonist a nucleic acid-based antagonist. In some embodiments, the anti-TLR4 antagonist is a small molecule inhibitor of TLR4. For example, suitable small molecule inhibitors include, by way of non-limiting example, TAK-242 (resatorvid) and/or E5564 (Eritoran).

In some embodiments, the methods also include the step of administering to the subject who has been implanted with a stem cell-related biological material, e.g., one or more stem cell transplantations and/or one or more bone marrow transplantations, one or more additional doses of an anti-TLR4 antagonist, wherein the antagonist is administered in an amount sufficient to inhibit, delay the progression of, or otherwise ameliorate a symptom of GvHD and/or improve survival of the transplanted biological material the subject. The additional dose(s) of anti-TLR4 antagonist can be administered before, during, or after the transplant. The additional dose(s) of anti-TLR4 antagonist can be the same anti-TLR4 antagonist or a different anti-TLR4 antagonist.

The invention provides methods of inhibiting, delaying the progression of, or otherwise ameliorating a symptom of GvHD and/or improving survival of stem cell-transplanted subjects, including bone marrow transplant subjects, by administering to the subject the antibody or immunologically active fragment thereof that specifically binds a Toll-like receptor 4 (TLR4) polypeptide.

In some embodiments, the methods also include the step of administering to the subject who has been implanted with a stem cell-related biological material, e.g., one or more stem cell transplantations and/or one or more bone marrow transplantations, one or more additional doses of an antibody or immunologically active fragment thereof that specifically binds TLR4, wherein the antibody is administered in an amount sufficient to inhibit, delay the progression of, or otherwise ameliorate a symptom of GvHD and/or improve survival of the transplanted biological material the subject. The additional dose(s) of anti-TLR4 antibody can be administered before, during, or after the transplant. The additional dose(s) of anti-TLR4 antibody can be the same anti-TLR4 antibody or a different anti-TLR4 antibody.

The invention provides methods of inhibiting GvHD and/or improving survival of GvHD subjects by contacting the stem cell-related biological material to be transplanted, e.g., one or more stem cell transplantations and/or one or more bone marrow transplantations, with an anti-TLR4 antagonist to produce a transplantable composition, implanting the transplantable composition at a desired location in the subject, and administering to the subject one or more additional doses of an anti-TLR4 antagonist, wherein the antagonist is administered in an amount sufficient to inhibit GvHD and/or improve survival of the GvHD subjects. The additional dose(s) of anti-TLR4 antagonist can be administered during the transplant, after the transplant or both. The additional dose(s) of anti-TLR4 antagonist can be the same anti-TLR4 antagonist or a different anti-TLR4 antagonist. In some embodiments, the anti-TLR4 antagonist is or is derived from an antibody or immunologically active fragment thereof that binds TLR4. In some embodiments, the anti-TLR4 antagonist is a peptide-based antagonist. In some embodiments, the anti-TLR4 antagonist a nucleic acid-based antagonist. In some embodiments, the anti-TLR4 antagonist is a small molecule inhibitor of TLR4.

The invention provides methods of inhibiting GvHD and/or improving survival of GvHD subjects by contacting the stem cell-related biological material to be transplanted, e.g., one or more stem cell transplantations and/or one or more bone marrow transplantations, with an antibody or immunologically active fragment thereof that specifically binds a Toll-like receptor 4 (TLR4) polypeptide to produce a transplantable composition, implanting the transplantable composition at a desired location in the subject, and administering to the subject one or more additional doses of an antibody or immunologically active fragment thereof that specifically binds TLR4, wherein the antibody is administered in an amount sufficient to inhibit GvHD and/or improve survival of the GvHD subjects. The additional dose(s) of anti-TLR4 antibody can be administered during the transplant, after the transplant or both. The additional dose(s) of anti-TLR4 antibody can be the same anti-TLR4 antibody or a different anti-TLR4 antibody.

The invention also provides methods of treating a subject who has received or will receive a transplant of stem cell-related biological material by administering to the subject one or more doses of an anti-TLR4 antagonist, wherein the antagonist is administered in an amount sufficient to inhibit GvHD and/or improve survival of the GvHD subject. In some embodiments, the anti-TLR4 antagonist is or is derived from an antibody or immunologically active fragment thereof that binds TLR4. In some embodiments, the anti-TLR4 antagonist is a peptide-based antagonist. In some embodiments, the anti-TLR4 antagonist a nucleic acid-based antagonist. In some embodiments, the anti-TLR4 antagonist is a small molecule inhibitor of TLR4.

The invention also provides methods of treating a subject who has received or will receive a transplant of stem cell-related biological material by administering to the subject one or more doses of an antibody or immunologically active fragment thereof that specifically binds a Toll-like receptor 4 (TLR4) polypeptide, wherein the antibody is administered in an amount sufficient to inhibit GvHD and/or improve survival of the GvHD subject.

In some embodiments, the GvHD is acute. In some embodiments, the GvHD is chronic. In some embodiments, the GvHD is a subtype of GvHD and/or a disease that is associated with or otherwise considered a side effect of GvHD, such as by way of non-limiting example, IPS, BOS, BOOP, acute pancreatitis, and/or acute hepatitis.

In some embodiments, the subject is a mammal. In a preferred embodiment, the subject is a human.

In some embodiments, the stem cell-related biological material to be transplanted is one or more cells or cell types, one or more tissues or tissue types, or an organ or portion thereof. For example, the biological material to be transplanted is allogeneic biological material.

In some embodiments, the biological material to be transplanted is bone marrow cells. In some embodiments, the bone marrow cells are allogeneic bone marrow cells.

In some embodiments, the biological material to be transplanted is hematopoietic stem cells. In some embodiments, the hematopoietic stem cells are allogeneic hematopoietic stem cells.

In some embodiments, the anti-TLR4 antagonist is administered prophylactically to a subject before the biological material has been transplanted, for example, in subjects known or suspected of being "high risk" for GvHD, such as, by way of non-limiting example, older recipients and/or recipients receiving transplanted materials from non-family related donors.

In some embodiments, the anti-TLR4 antagonist that is used to contact the biological material prior to transplantation, i.e., the first anti-TLR4 antagonist, is the same anti-TLR4 antagonist that is administered to the subject before, during and/or after the biological material has been transplanted, i.e., the second anti-TLR4 antagonist. In some embodiments, the first and second anti-TLR4 antagonists are administered at the same dosage. In some embodiments, the first and second anti-TLR4 antagonists are administered at a different dosage.

In some embodiments, the anti-TLR4 antibody that is used to contact the biological material prior to transplantation, i.e., the first anti-TLR4 antibody, is the same anti-TLR4 antibody that is administered to the subject before, during and/or after the biological material has been transplanted, i.e., the second anti-TLR4 antibody. In some embodiments, the first and second anti-TLR4 antibodies are administered at the same dosage. In some embodiments, the first and second anti-TLR4 antibodies are administered at a different dosage.

In some embodiments, the anti-TLR4 antagonist that is used to contact the biological material prior to transplantation, i.e., the first anti-TLR4 antagonist, is a different antibody than the anti-TLR4 antagonist that is administered to the subject before, during and/or after the biological material has been transplanted, i.e., the second anti-TLR4 antagonist. In some embodiments, the first and second anti-TLR4 antagonists are administered at the same dosage. In some embodiments, the first and second anti-TLR4 antagonists are administered at a different dosage.

In some embodiments, the anti-TLR4 antibody that is used to contact the biological material prior to transplantation, i.e., the first anti-TLR4 antibody, is a different antibody than the anti-TLR4 antibody that is administered to the subject before, during and/or after the biological material has been transplanted, i.e., the second anti-TLR4 antibody. In some embodiments, the first and second anti-TLR4 antibodies are administered at the same dosage. In some embodiments, the first and second anti-TLR4 antibodies are administered at a different dosage.

Administration of an anti-TLR4 antagonist, including an anti-TLR4 antibody or fragment thereof, to a patient who is receiving, has received and/or will be receiving stem cell-related transplanted material is considered successful if any of a variety of laboratory or clinical objectives is achieved. For example, administration of an anti-TLR4 antagonist, including an anti-TLR4 antibody or fragment thereof, to a patient who is receiving, has received and/or will be receiving stem cell-related transplanted material is considered successful if one or more of the symptoms associated with GvHD is alleviated, reduced, inhibited or does not progress to a further, i.e., worse, state. Administration of an anti-TLR4 antagonist, including an anti-TLR4 antibody or frag ment thereof, to a patient who is receiving, has received and/or will be receiving stem cell-related transplanted material is considered successful if one or more of the symptoms associated with GvHD is considered successful if GvHD enters remission or does not progress to a further, i.e., worse, state.

Symptoms of acute and chronic GvHD range from mild to severe. Symptoms of acute GvHD, which usually happens within the first three months after a transplant, include by way of non-limiting example, abdominal pain or cramps, nausea, vomiting, diarrhea, dry or irritated eyes, jaundice, skin rash, itching, and/or redness on areas of the skin. Symptoms of chronic GvHD, which usually starts more than 3 months after a transplant, and, in some instances, can last a lifetime, include by way of non-limiting example, dry eyes or vision changes, dry mouth, white patches inside the mouth, sensitivity to spicy foods, fatigue, muscle weakness, chronic pain, skin rash with raised, discolored areas, as well as skin tightening or thickening, shortness of breath, vaginal dryness, and/or weight loss.

The anti-TLR4 antibodies or immunologically active fragments thereof provided herein are capable of blocking, e.g., neutralizing, receptor activation and subsequent intracellular signaling induced TLR4 ligands, e.g., LPS or any other TLR4 ligand described herein. In some embodiments, the antibody is an antibody or an immunologically active fragment thereof. In some embodiments, the antibody or immunologically active fragment thereof that binds TLR4 is a monoclonal antibody. In some embodiments, the antibody or immunologically active fragment thereof that binds TLR4 is a mouse, chimeric, humanized, fully human monoclonal antibody, domain antibody, single chain, $F_{ab}$, $F_{ab'}$ and $F_{(ab')2}$ fragments, scFvs, or an $F_{ab}$ expression library. In some embodiments, the anti-TLR4 antibodies also bind the human TLR4/MD-2 receptor complex.

In some embodiments, the antibody or an immunologically active fragment thereof binds a human TLR4 polypeptide. In some embodiments, the human TLR4 polypeptide comprises the amino acid sequence:

(SEQ ID NO: 11)

```
  1 mmsasrlagt lipamaflsc vrpeswepcv evvpnityqc melnfykipd nlpfstknld
 61 lsfnplrhlg sysffsfpel qvldlsrcei qtiedgayqs lshlstlilt gnpiqslalg
121 afsglsslqk lvavetnlas lenfpighlk tlkelnvahn liqsfklpey fsnltnlehl
181 dlssnkiqsi yctdlrvlhq mpllnlsldl slnpmnfiqp gafkeirlhk ltlrnnfdsl
241 nvmktciqgl aglevhrlvl gefrnegnle kfdksalegl cnltieefrl ayldyylddi
301 idlfncltnv ssfslvsvti ervkdfsynf gwqhlelvnc kfgqfptlkl kslkrltfts
361 nkggnafsev dlpslefldl srnglsfkgc csqsdfgtts lkyldlsfng vitmssnflg
421 leglehldfq hsnlkqmsef svflslrnli yldishthtr vafngifngl sslevlkmag
481 nsfqenflpd iftelrnltf ldlsqcqleq lsptafnsls slqvlnmshn nffsldtfpy
541 kclnslqvld yslnhimtsk kqelqhfpss laflnitqnd factcehqsf lqwikdqrql
601 lvevermeca tpsdkqgmpv lslnitcqmn ktiigvsvls vlvvsvvavl vykfyfhlml
661 lagcikygrg eniydafviy ssqdedwvrn elvknleegv ppfqlclhyr dfipgvaiaa
721 niihegfhks rkvivvvsqh fiqsrwcife yeiaqtwqfl ssragiifiv lqkvektllr
781 qqvelyrlls rntyleweds vlgrhifwrr lrkalldgks wnpegtvgtg cnwqeatsi
```

In some embodiments, the anti-TLR4 antagonist, e.g., an antibody or immunologically active fragment thereof that specifically binds TLR4, is administered before, during and/or after transplantation in combination with one or more additional agents. In some embodiments, the anti-TLR4 antagonist, e.g., an anti-TLR4 antibody, and the additional agent(s) are administered simultaneously. For example, the anti-TLR4 antagonist, e.g., an anti-TLR4 antibody, and the additional agent(s) can be formulated in a single composition or administered as two or more separate compositions. In some embodiments, the anti-TLR4 antagonist, e.g., an anti-TLR4 antibody, and the additional agent(s) are administered sequentially.

In some embodiments, the additional agent(s) is an immunosuppressive agent. For example, the additional agent(s) is selected from methotrexate, cyclosporin A, tacrolimus, sirolimus, everolimus, a corticosteroid, anti-thymocyte globulin, Infliximab, Etanercept and Adalimumab. The additional agent(s) can also include any compound or other molecule that exhibits an immunosuppressive effect.

In some embodiments, the antibody or immunologically active fragment thereof that binds TLR4 comprises a variable heavy chain complementarity determining region 1 ($V_H$ CDR1) comprising an amino acid sequence at least 90%, 91%, 92%, 93%, 94%, 95%, 96%, 97% 98%, 99% or more identical to the amino acid sequence of GGYSWH (SEQ ID NO: 1); a $V_H$ CDR2 region comprising an amino acid sequence at least 90%, 91%, 92%, 93%, 94%, 95%, 96%, 97% 98%, 99% or more identical to the amino acid sequence of YIHYSGYTDFNPSLKT (SEQ ID NO: 2); and a $V_H$ CDR3 region comprising an amino acid sequence at least 90%, 91%, 92%, 93%, 94%, 95%, 96%, 97% 98%, 99% or more identical to the amino acid sequence of KDPSDAFPY (SEQ ID NO: 3); a variable light chain complementarity determining region 1 ($V_L$ CDR1) region comprising an amino acid sequence at least 90%, 91%, 92%, 93%, 94%, 95%, 96%, 97% 98%, 99% or more identical to the amino acid sequence of RASQSISDHLH (SEQ ID NO: 4); a $V_L$ CDR2 region comprising an amino acid sequence at least 90%, 91%, 92%, 93%, 94%, 95%, 96%, 97% 98%, 99% or more identical to the amino acid sequence of YASHAIS (SEQ ID NO: 5); and a $V_L$ CDR3 region comprising an amino acid sequence at least 90%, 91%, 92%, 93%, 94%, 95%, 96%, 97% 98%, 99% or more identical to the amino acid sequence of QQGHSFPLT (SEQ ID NO: 6). In some embodiments, the antibody or immunologically active fragment thereof that binds TLR4 further comprises an amino acid sequence at least 90%, 91%, 92%, 93%, 94%, 95%, 96%, 97% 98%, 99% or more identical to the heavy chain variable amino acid sequence QVQLQESGPGLVKPS-DTLSLTCAVSGYSITGGYSWHWIRQPPGKGLEWM-GYIHYSGYT DFNPSLKTRITISRDTSKNQFSLKLSS-VTAVDTAVYYCARKDPSDAFPYWGQGTLVTVS S (SEQ ID NO: 7) and an amino acid sequence at least 90%, 91%, 92%, 93%, 94%, 95%, 96%, 97% 98%, 99% or more identical to the light chain variable amino acid sequence EIVLTQSPDFQSVTPKEKVTITCRASQSISDHLHWY-QQKPDQSPKLLIKYASHAISGVPS RFSGSGSGTD-FTLTINSLEAEDAATYYCQQGHSFPLTFGGGTKVEIK (SEQ ID NO: 8). In some embodiments, the antibody or immunologically active fragment thereof that binds TLR4 further comprises an amino acid sequence at least 90%, 91%, 92%, 93%, 94%, 95%, 96%, 97% 98%, 99% or more identical to the heavy chain amino acid sequence MGWS-WIFLFLLSGTAGVHCQVQLQESGPGLVKPSDTLSLT-CAVSGYSITGGYSWHWIR QPPGKGLEWMGYIHYS-GYTDFNPSLKTRITISRDTSKNQFSLKLSSVTAVDTA-VYYCAR KDPSDAFPYWGQGTLVTVSSASTKGPSVF-PLAPSSKSTSGGTAALGCLVKDYFPEPVTV SWNS-GALTSGVHTFPAVLQSSGLYSLSSVVTVPSSSLGTQ-TYICNVNHKPSNTKVDKR VEPKSCDKT-HTCPPCPAPELLGGPSVFLFPPKPKDTLMISRTPE-VTCVVVDVSHEDPEV KFNWYVDGVEVHNAKTK-PREEQYNSTYRVVSVLTVLHQDWLNGKEYKCK-VSSKAFP APIEKTISKAKGQPREPQVYTLPPSREE-MTKNQVSLTCLVKGFYPSDIAVEWESNGQPE NNYK-TTPPVLDSDGSFFLYSKLTVDKSRWQQGNVFSCSVM-HEALHNHYTQKSLSLSP GK (SEQ ID NO: 9) and an amino acid sequence at least 90%, 91%, 92%, 93%, 94%, 95%, 96%, 97% 98%, 99% or more identical to the light chain amino acid sequence MEWSWVFLFFLSVTTGVH-SEIVLTQSPDFQSVTPKEKVTITCRASQSISDHLHWY-QQKP DQSPKLLIKYASHAISGVPSRFSGSGSGTD-FTLTINSLEAEDAATYYCQQGHSFPLTFGG GTKVEIKRTVAAPSVFIFPPSDEQLKSGTASVVCLLN-NFYPREAKVQWKVDNALQSGN SQESVTEQDSKD-STYSLSSTLTLSKADYEKHKVY-ACEVTHQGLSSPVTKSFNRGEC (SEQ ID NO: 10).

In some embodiments, anti-TLR4 antibody or immunologically active fragment thereof is or is derived from an antibody as described in PCT/IB2005/004206, filed Jun. 14, 2005 and published as WO 2007/110678, the contents of which are hereby incorporated by reference in their entirety.

In some embodiments, anti-TLR4 antibody or immunologically active fragment thereof is or is derived from an antibody as described in PCT application PCT/IB2008/003978, filed May 14, 2008 and published as WO 2009/101479, the contents of which are hereby incorporated by reference in their entirety.

In some embodiments, anti-TLR4 antibody or immunologically active fragment thereof is or is derived from the anti-TLR4 antibody known as HTA125, which is described, for example, in Shimazu, et al., J. Exp. Med., vol. 189:1777-1782 (1999); Nijhuis et al., Clin. Diag. Lab. Immunol., vol. 10(4): 558-63 (2003); and Pivarcsi et al., Intl. Immunopharm., vol. 15(6):721-730 (2003), the contents of each of which are hereby incorporated by reference in their entirety.

In some embodiments, the anti-TLR4 antibody or immunologically active fragment thereof is or is derived from a domain antibody such as, for example, the domain antibodies that bind TLR4 described in PCT application PCT/EP2009/055926, filed May 15, 2009 and published as WO 2009/13848, the contents of which are hereby incorporated by reference in their entirety.

In some embodiments, the anti-TLR4 antibody or immunologically active fragment thereof binds to an epitope comprising one or more amino acid residues on human TLR4 between residues 289 and 375 of SEQ ID NO: 11. For example, in some embodiments, the antibody or immunologically active fragment thereof binds to an epitope that comprises at least residues 328 and 329 of SEQ ID NO: 11. For example, in some embodiments, the antibody or immunologically active fragment thereof binds to an epitope that comprises at least residues 349 through 351 of SEQ ID NO: 11. For example, in some embodiments, the antibody or immunologically active fragment thereof binds to an epitope that comprises at least residues 369 through 371 of SEQ ID NO: 11. For example, in some embodiments, the antibody or immunologically active fragment thereof binds to an epitope that comprises at least residues 328, 329, 349 through 351 and 369 through 371 of SEQ ID NO: 11. For example, in some embodiments, the antibody or immunologically active fragment thereof binds to an epitope that comprises at least residues 293 through 295 of SEQ ID NO: 11. For example, in some embodiments, the antibody or immunologically active fragment thereof binds to an epitope that comprises at least residues 296 and 297 of SEQ ID NO: 11. For example, in some embodiments, the antibody or immunologically active fragment thereof binds to an epitope that comprises at least residues 319 through 321 of SEQ ID NO: 11. For example, in some embodiments, the antibody or immunologically active fragment thereof binds to an epitope that comprises at least residues 293 through 295, 296, 297 and 319 through 321 of SEQ ID NO: 11.

In some embodiments, anti-TLR4 antibody or immunologically active fragment thereof is or is derived from an antibody as described in PCT/US2013/034543, filed Mar. 29, 2013 and published as WO 2013/14911, the contents of which are hereby incorporated by reference in their entirety.

The anti-TLR4 antibodies of the invention also include antibodies that include a heavy chain variable amino acid sequence that is at least 90%, 91%, 92%, 93%, 94%, 95%, 96%, 97% 98%, 99% or more identical an amino acid sequence shown herein, and/or a light chain variable amino acid that is at least 90%, 91%, 92%, 93%, 94%, 95%, 96%, 97% 98%, 99% or more identical an amino acid sequence shown herein.

In some embodiments, the anti-TLR4 antibodies described herein also include at least one specific amino acid substitution within, for example, an Fc region or an FcR binding fragment thereof (e.g., a polypeptide having amino acid substitutions within an IgG constant domain) such that the modified antibody elicits alterations in antigen-dependent effector function while retaining binding to antigen as compared to an unaltered antibody. For example, the altered antibodies elicit the prevention of proinflammatory mediator release. In a preferred embodiment, the altered antibodies are human and of the IgG1 isotype.

The anti-TLR4 antibodies of the invention include an altered antibody in which at least one amino acid residue in the constant region of the Fc portion of the antibody has been modified. For example, at least one amino acid in the CH2 domain of the Fc portion has been replaced by a different residue, i.e., an amino acid substitution. In the altered antibodies described herein, one or more of the amino acid residues that correspond to residues 325, 326 and 328 is substituted with a different residue as compared to an unaltered antibody. The numbering of the residues in the gamma heavy chain is that of the EU index (see Edelman, G. M. et al., 1969; Kabat, E, A., T. T. Wu, H. M. Perry, K. S. Gottesman, and C. Foeller., 1991. *Sequences of Proteins of Immunological Interest*, 5th Ed. U.S. Dept. of Health and Human Services, Bethesda, Md., NIH Publication n. 91-3242). In a preferred embodiment, EU amino acid position 325 of the gamma heavy chain constant region is substituted with serine, and EU amino acid position 328 of the gamma heavy chain constant region is substituted with phenylalanine, such that the EU positions 325 to 328 of the gamma heavy chain constant region of the altered human IgG1 antibody comprise the amino acid sequence SKAF (SEQ ID NO: 76).

Pharmaceutical compositions according to the invention can include an antibody of the invention and a carrier. These pharmaceutical compositions can be included in kits, such as, for example, diagnostic kits.

DETAILED DESCRIPTION OF THE INVENTION

Figure 1:
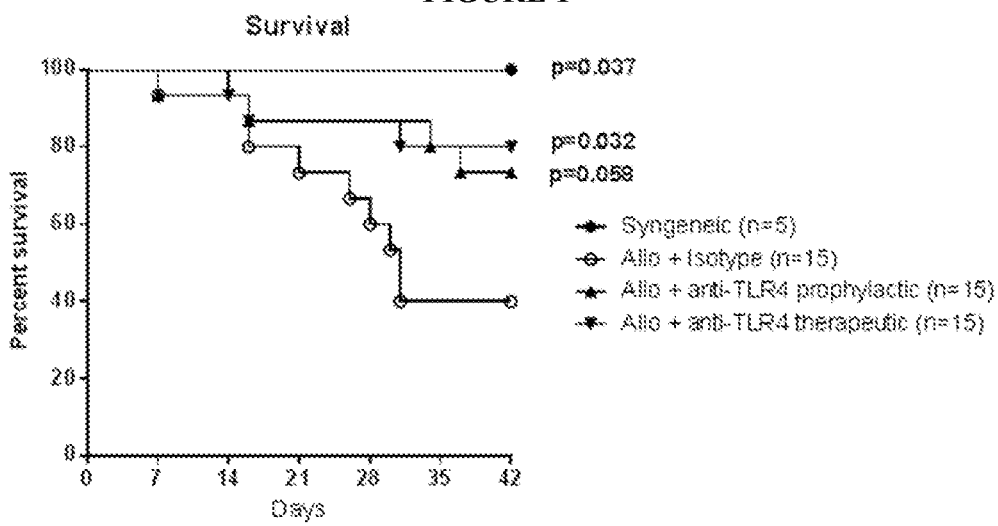
FIG. 1 is a graph depicting the protective effect of anti-TLR4 treatment against animal death in a murine model of GvHD. Statistics were performed with Log-rank (Mantel-Cox) test relative to Allo-isotype group.

The present invention provides antagonists to Toll like Receptor 4 (TLR4), such as, for example, monoclonal antibodies (mAbs) that specifically bind Toll like Receptor 4, and more specifically, human TLR4. These anti-TLR4 antagonists, including anti-TLR4 antibodies are used in methods of inhibiting GvHD and/or improving survival of GvHD subjects.

In some embodiments, the anti-TLR4 antagonists are antibodies and immunologically active fragments thereof that bind TLR4. Anti-TLR4 antibodies include antibodies that bind the human TLR4/MD-2 receptor complex and also bind TLR4 independently of the presence of MD-2.

TLR4 antibodies of the invention include, for example, antibodies having the combination of heavy chain and light chain sequences shown below.

Exemplary antibodies of the invention include, for example, the anti-TLR4 antibodies described in PCT/IB2005/004206, filed Jun. 14, 2005 and published as WO 2007/110678, the anti-TLR4 antibodies described in PCT application PCT/IB2008/003978, filed May 14, 2008 and published as WO 2009/101479, the contents of each of which are hereby incorporated by reference in their entirety, and commercially available antibodies such as HTA125.

Exemplary antibodies of the invention include, for example, the antibody referred to herein as NI-0101, which binds the human TLR4/MD2 complex and also binds TLR4 independently of the presence of MD-2. The sequences of the NI-0101 (hu15c1) antibody are shown below, with the CDR sequences underlined in the VH and VL amino acid sequences:

NI-0101 heavy chain nucleotide sequence:
(SEQ ID NO: 12)
ATGGGATGGAGCTGGATCTTTCTCTTCCTCCTGTCAGGAACTGCAGGTGT

ACATTGCCAGGTGCAGCTTCAGGAGTCCGGCCCAGGACTGGTGAAGCCTT

CGGACACCCTGTCCCTCACCTGCGCTGTCTCTGGTTACTCCATCACCGGT

GGTTATAGCTGGCACTGGATACGGCAGCCCCAGGGAAGGGACTGGAGTG

GATGGGGTATATCCACTACAGTGGTTACACTGACTTCAACCCCTCCCTCA

AGACTCGAATCACCATATCACGTGACACGTCCAAGAACCAGTTCTCCCTG

AAGCTGAGCTCTGTGACCGCTGTGGACACTGCAGTGTATTACTGTGCGAG

AAAAGATCCGTCCGACGCCTTTCCTTACTGGGGCCAAGGGACTCTGGTCA

CTGTCTCTTCCGCCTCCACCAAGGGCCCATCGGTCTTCCCCCTGGCACCC

TCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGA

CCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGAC

CTACATCTGCAACGTGAATCACAAGCCCAGCAACACCAAGGTGGACAAGA

GAGTTGAGCCCAAATCTTGTGACAAAACTCACACATGCCCACCGTGCCCA

GCACCTGAACTCCTGGGGGGACCGTCAGTCTTCCTCTTCCCCCCAAAACC

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

TGAATGGCAAGGAGTACAAATGCAAGGTCTCCAGTAAAGCTTTCCCTGCC

CCCATCGAGAAAACCATCTCCAAAGCCAAAGGGCAGCCCCGAGAACCACA

GGTGTACACCCTGCCCCCATCCCGGGAGGAGATGACCAAGAACCAGGTCA

GCCTGACCTGCCTGGTCAAAGGCTTCTATCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTATAGCAAGCTCACCGTGGACA

AGAGCAGGTGGCAGCAGGGGAACGTCTTCTCATGCTCCGTGATGCATGAG

GCTCTGCACAACCACTACACGCAGAAGAGCCTCTCCCTGTCTCCGGGTAA

ATAG

NI-0101 heavy chain amino acid sequence:
(SEQ ID NO: 9)
MGWSWIFLFLLSGTAGVHCQVQLQESGPGLVKPSDTLSLTCAVSGYSIT<u>G</u>

<u>GYSWHW</u>IRQPPGKGLEWMG<u>YIHYSGYTDFNPSLKT</u>RITISRDTSKNQFSL

KLSSVTAVDTAVYYCAR<u>KDPSDAFPY</u>WGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSSKAFPA

```
-continued
PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

NI-0101 light chain nucleotide sequence:
                              (SEQ ID NO: 13)
ATGGAATGGAGCTGGGTCTTTCTCTTCTTCCTGTCAGTAACTACAGGTGT

CCACTCCGAAATTGTGTTGACGCAGTCTCCAGACTTTCAGTCTGTGACTC

CAAAGGAAAAAGTCACCATCACCTGCAGGGCCAGTCAGAGTATCAGCGAC

CACTTACACTGGTACCAACAGAAACCTGATCAGTCTCCCAAGCTCCTCAT

CAAATATGCTTCCCATGCCATTTCTGGGGTCCCATCGAGGTTCAGTGGCA

GTGGGTCTGGGACAGACTTCACTCTCACCATCAATAGCCTAGAGGCTGAA

GATGCTGCAACGTATTACTGTCAGCAGGGTCACAGTTTTCCGCTCACTTT

CGGCGGAGGGACCAAGGTGGAGATCAAACGTACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG

NI-0101 light chain amino acid sequence:
                              (SEQ ID NO: 10)
MEWSWVFLFFLSVTTGVHSEIVLTQSPDFQSVTPKEKVTITCRASQSISD

HLHWYQQKPDQSPKLLIKYASHAISGVPSRFSGSGSGTDFTLTINSLEAE

DAATYYCQQGHSFPLTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC
```

The NI-0101 (hu15c1) antibody includes VH CDRs having the sequences GGYSWH (SEQ ID NO: 1), YIHYSGYTDFNPSLKT (SEQ ID NO: 2), and KDPSDAFPY (SEQ ID NO: 3), and VL CDRs having the sequences RASQSISDHLH (SEQ ID NO: 4), YASHAIS (SEQ ID NO: 5) and QQGHSFPLT (SEQ ID NO: 6).

The amino acid and nucleic acid sequences of the heavy chain variable (VH) and light chain variable (VL) regions of the anti-TLR4/MD-2 antibodies are shown below. The amino acids encompassing the complementarity determining regions (CDR) as defined by Chothia et al. 1989, E. A. Kabat et al., 1991 are highlighted in underlined and italicized text below. (See Chothia, C, et al., Nature 342:877-883 (1989); Kabat, E A, et al., Sequences of Protein of immunological interest, Fifth Edition, US Department of Health and Human Services, US Government Printing Office (1991)).

Anti-TLR4 antibodies include the antibodies described in co-pending U.S. application Ser. No. 11/009,939, filed Dec. 10, 2004 and Ser. No. 11/151,916, filed Jun. 15, 2004 and in WO 05/065015, filed Dec. 10, 2004 and PCT/US2005/020930, filed Jun. 15, 2004, each of which is hereby incorporated by reference in its entirety. Several exemplary antibodies include the antibodies referred to therein as 18H10, 16G7, 15C1 and 7E3.

Anti-TLR4 antibodies include the antibodies described in co-pending U.S. application Ser. No. 11/151,916, filed Jun. 15, 2004 (U.S. Patent Publication No. US 2008-0050366 A1) and in PCT/IB2005/004206, filed Jun. 15, 2004 (PCT Publication No. WO 07/110678), each of which is hereby incorporated by reference in its entirety. The sequences of several exemplary antibodies are shown below.

```
15C1 Hu V_H version 4-28
                              (SEQ ID NO: 14)
QVQLQESGPG LVKPSDTLSL TCAVSGYSI X_1 GGYSWH WIRQ

PPGKGLEW X_2 G YIHYSGYTDF NPSLKT R X_3 T X_4 SRDTSKNQFS

LKLSSVTAVD TAVYYCAR KD PSDGFPY WGQ GTLVTVSS

CDR 1:
                              (SEQ ID NO: 1)
GGYSWH

CDR 2:
                              (SEQ ID NO: 2)
YIHYSGYTDFNPSLKT

CDR 3:
                              (SEQ ID NO: 3)
KDPSDGFPY
Where X_1 is Thr or Ser
Where X_2 is Ile or Met
Where X_3 is Val or Ile
Where X_4 is Met or Ile 15C1 Hu V_H version 3-66
                              (SEQ ID NO: 15)
EVQLVESGGG LVQPGGSLRL SCAX_1SGYSIT GGYSWH WVRQ

APGKGLEWX_2S YIHYSGYTDF NPSLKT RFTI SRDNSKNTX_3Y

LQMNSLRAED TAVYYCAR KD PSDGFP YWGQ GTLVTVSS

CDR 1:
                              (SEQ ID NO: 1)
GGYSWH

CDR 2:
                              (SEQ ID NO: 2)
YIHYSGYTDFNPSLKT

CDR 3:
                              (SEQ ID NO: 3)
KDPSDGFPY
Where X_1 is Ala or Val
Where X_2 is Val or Met
Where X_3 is Leu or Phe 15C1 Hu VL version L6
                              (SEQ ID NO: 16)
EIVLTQSPAT LSLSPGERAT LSC RASQSIS DHLH WYQQKP

GQAPRLLIX_1Y ASHAIS GIPA RFSGSGSGTD FTLTISSLEP

EDFAVYYC QN GHSFPLT FGG GTKVEIK

CDR1:
                              (SEQ ID NO: 4)
RASQSISDHLH

CDR2:
                              (SEQ ID NO: 5)
YASHAIS

CDR3:
                              (SEQ ID NO: 17)
QNGHSFPLT
Where X_1 is Lys or Tyr 15C1 Hu VL version A26
```

```
                                                     (SEQ ID NO: 18)
EIVLTQSPDF QSVTPKEKVT ITCRASQSIS DHLHWYQQKP

DQSPKLLIKY ASHAISGVPS RFSGSGSGTD FTLTINSLEA

EDAATYYCQN GHSFPLTFGG GTKVEIK
```

CDR1:
```
                                                     (SEQ ID NO: 4)
RASQSISDHLH
```

CDR2:
```
                                                     (SEQ ID NO: 5)
YASHAIS
```

CDR3:
```
                                                     (SEQ ID NO: 17)
QNGHSFPLT
```

18H10 Hu VH version 1-69
```
                                                     (SEQ ID NO: 19)
QVQLVQSGAE VKKPGSSVKV SCKASGFNIK DSYIHWVRQA

PGQGLEWX₁GW TDPENVNSIY DPRFQGRVTI TADX₂STSTAY

X₃ELSSLRSED TAVYYCARGY NGVYYAMDYW GQGTTVTVSS
```

CDR1:
```
                                                     (SEQ ID NO: 20)
DSYIH
```

CDR2:
```
                                                     (SEQ ID NO: 21)
WTDPENVNSIYDPRFQG
```

CDR3:
```
                                                     (SEQ ID NO: 22)
GYNGVYYAMDY
Where X₁ is Met or Ile
Where X₂ is Lys or Thr
Where X₃ is Met or Leu
```

18H10 Hu VL version L6
```
                                                     (SEQ ID NO: 23)
EIVLTQSPAT LSLSPGERAT LSCSASSSVI YMHWYQQKPG

QAPRLLIYRT YNLASGIPAR FSGSGSGTDX₁ TLTISSLEPE

DFAVYYCHQW SSFPYTFGQG TKVEIK
```

CDR1:
```
                                                     (SEQ ID NO: 24)
SASSSVIYMH
```

CDR2:
```
                                                     (SEQ ID NO: 25)
RTYNLAS
```

CDR3:
```
                                                     (SEQ ID NO: 26)
HQWSSFPYT
Where X₁ is Phe or Tyr
```

7E3 Hu VH version 2-70
```
                                                     (SEQ ID NO: 27)
QVTLRESGPA LVKPTQTLTL TCTFSGFSLX₁ TYNIGVGWIR

QPPGKALEWL AHIWWNDNIY YNTVLKSRLT X₂SKDTSKNQV

VLTMTNMDPV DTATYYCX₃RM AEGRYDAMDY WGQGTLVTVS

S
```

CDR1:
```
                                                     (SEQ ID NO: 28)
TYNIGVG
```

CDR2:
```
                                                     (SEQ ID NO: 29)
HIWWNDNIYYNTVLKS
```

CDR3:
```
                                                     (SEQ ID NO: 30)
MAEGRYDAMDY
Where X₁ is Ser or Thr
Where X₂ is Ile or Phe
Where X₃ is Ile or Ala
```

7E3 Hu VH version 3-66
```
                                                     (SEQ ID NO: 31)
EVQLVESGGG LVQPGGSLRL SCAX₁SGFSLT TYNIGVGWVR

QAPGKGLEWX₂ SHIWWNDNIY YNTVLKSRLT X₃SX₄DNSKNTX₅

YLQMNSLRAE DTAVYYCX₆RM AEGRYDAMDY WGQGTLVTVS

S
```

CDR1:
```
                                                     (SEQ ID NO: 28)
TYNIGVG
```

CDR2:
```
                                                     (SEQ ID NO: 29)
HIWWNDNIYYNTVLKS
```

CDR3:
```
                                                     (SEQ ID NO: 30)
MAEGRYDAMDY
Where X₁ is Phe or Ala
Where X₂ is Val or Leu
Where X₃ is Ile or Phe
Where X₄ is Lys or Arg
Where X₅ is Leu or Val
Where X₆ is Ile or Ala
```

7E3 Hu VL version L19
```
                                                     (SEQ ID NO: 32)
DIQMTQSPSS VSASVGDRVT ITCRASQDIT NYLNWYQQKP

GKAPKLLIYY TSKLHSGVPS RFSGSGSGTD X₁TLTISSLQP

EDFATYX₂CQQ GNTFPWTFGG GTKVEIK
```

CDR1:
```
                                                     (SEQ ID NO: 33)
RASQDITNYLN
```

CDR2:
```
                                                     (SEQ ID NO: 34)
YTSKLHS
```

CDR3:
```
                                                     (SEQ ID NO: 35)
QQGNTFPWT
Where X₁ is Phe or Tyr
Where X₂ is Tyr or Phe
```

Anti-TLR4 antibodies include the antibodies described in PCT/IB2008/003978, filed May 14, 2008 (PCT Publication No. WO 2009/101479), the contents of which are hereby incorporated by reference in their entirety. These anti-TLR4 antibodies are modified to include one or more mutations in the CDR3 portion. The sequences of several exemplary antibodies are shown below.

15C1 humanized VH mutant 1 amino acid sequence:
```
                                                     (SEQ ID NO: 36)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

PSDAFPYWGQGTLVTVSS
```

15C1 humanized VH mutant 1 nucleic acid sequence:
(SEQ ID NO: 37)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

CCGTCCGACGCCTTTCCTTACTGGGGCCAAGGGACTCTGGTCACTGTCTC

TTCC

15C1 humanized VH mutant 2 amino acid sequence:
(SEQ ID NO: 38)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

PSEGFPYWGQGTLVTVSS

15C1 humanized VH mutant 2 nucleic acid sequence:
(SEQ ID NO: 39)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

CCGTCCGAGGGATTTCCTTACTGGGGCCAAGGGACTCTGGTCACTGTCTC

TTCC

15C1 humanized VL mutant 1 amino acid sequence:
(SEQ ID NO: 40)
EIVLTQSPDFQSVTPKEKVTITCRASQSISDHLHWYQQKPDQSPKLLIKY

ASHAISGVPSRFSGSGSGTDFTLTINSLEAEDAATYYCQNSHSFPLTFGG

GTKVEIK

15C1 humanized VL mutant 1 nucleic acid sequence:
(SEQ ID NO: 41)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGAATAGTCACAGTTTTCCGCTCACTTTCGGCGGA

GGGACCAAGGTGGAGATCAAA

15C1 humanized VL mutant 2 amino acid sequence:
(SEQ ID NO: 42)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

15C1 humanized VL mutant 2 nucleic acid sequence:
(SEQ ID NO: 43)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

15C1 humanized VL mutant 3 amino acid sequence:
(SEQ ID NO: 44)
EIVLTQSPDFQSVTPKEKVTITCRASQSISDHLHWYQQKPDQSPKLLIKY

ASHAISGVPSRFSGSGSGTDFTLTINSLEAEDAATYYCQNSSSFPLTFGG

GTKVEIK

15C1 humanized VL mutant 3 nucleic acid sequence:
(SEQ ID NO: 45)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGAATAGTAGTAGTTTTCCGCTCACTTTCGGCGGA

GGGACCAAGGTGGAGATCAAA

15C1 humanized VL mutant 4 amino acid sequence:
(SEQ ID NO: 46)
EIVLTQSPDFQSVTPKEKVTITCRASQSISDHLHWYQQKPDQSPKLLIKY

ASHAISGVPSRFSGSGSGTDFTLTINSLEAEDAATYYCQQSHSFPLTFGG

GTKVEIK

15C1 humanized VL mutant 4 nucleic acid sequence:
(SEQ ID NO: 47)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGAGTCACAGTTTTCCGCTCACTTTCGGCGGA

GGGACCAAGGTGGAGATCAAA

Antibodies of the invention interfere with or otherwise antagonize signaling via human TLR4 and/or human TLR4/MD-2 complexes. In some embodiments, antibodies of the invention also bind cynomolgus monkey TLR4 and/or cynomolgus monkey TLR4/MD-2 complexes. In some embodiments, the antibody binds to an epitope that includes one or more amino acid residues on human and/or cynomolgus monkey TLR4 having the following sequences:

>Human TLR4 amino acid sequence
(SEQ ID NO: 11)
MMSASRLAGTLIPAMAFLSCVRPESWEPCVEVVPNITYQCMELNFYKIPD

NLPFSTKNLDLSFNPLRHLGSYSFFSFPELQVLDLSRCEIQTIEDGAYQS

LSHLSTLILTGNPIQSLALGAFSGLSSLQKLVAVETNLASLENFPIGHLK

TLKELNVAHNLIQSFKLPEYFSNLTNLEHLDLSSNKIQSIYCTDLRVLHQ

-continued
MPLLNLSLDLSLNPMNFIQPGAFKEIRLHKLTLRNNFDSLNVMKTCIQGL

AGLEVHRLVLGEFRNEGNLEKFDKSALEGLCKLTIEEFRLAYLDYYLDDI

IDLFNCLTNVSSFSLVSVTIERVKDFSYNFGWQHLELVNCKFGQFPTLKL

KSLKRLTFTSNKGGNAFSEVDLPSLEFLDLSRNGLSFKGCCSQSDFGTTS

LKYLDLSFNGVITMSSNFLGLEQLEHLDFQHSNLKQMSEFSVFLSLRNLI

YLDISHTHTRVAFNGIFNGLSSLEVLKMAGNSFQENFLPDIFTELRNLTF

LDLSQCQLEQLSPTAFNSLSSLQVLNMSHNNFFSLDTFPYKCLNSLQVLD

YSLNHIMTSKKQELQHFPSSLAFLNLTQNDFACTCEHQSFLQWIKDQRQL

LVEVERMECATPSDKQGMPVLSLNITCQMNKTIIGVSVLSVLVVSVVAVL

VYKFYPHLMLLAGCIKYGRGENIYDAFVIYSSQDEDWVRNELVKNLEEGV

PPFQLCLHYRDFIPGVAIAANIIHEGFHKSRKVIVVVSQHFIQSRWCIFE

YEIAQTWQFLSSRAGIIFIVLQKVEKTLLRQQVELYRLLSRNTYLEWEDS

VLGRHIFWRRLRKALLDGKSWNPEGTVGTGCNWQEATSI

>Cynomolgus monkey TLR4 amino acid sequence 1
(SEQ ID NO: 77)
MTSALRLAGTLIPAMAFLSCVRPESWEPCVEVVPNITYQCMELKFYKIPD

NIPFSTKNLDLSFNPLRHLGSYSFLRFPELQVLDLSRCEIQTIEDGAYQS

LSHLSTLILTGNPIQSLALGAFSGLSSLQKLVAVETNLASLENFPIGHLK

TLKELNVAHNLIQSFKLPEYFSNLTNLEHLDLSSNKIQNIYCKDLQVLHQ

MPLSNLSLDLSLNPINFIQPGAFKEIRLHKLTLRSNFDDLNVMKTCIQGL

AGLEVHRLVLGEFRNERNLEEFDKSSLEGLCKLTIEEFRLTYLDCYLDNI

IDLFNCLANVSSFSLVSVNIKRVEDFSYNFRWQHLELVNCKFEQFPTLEL

KSLKRLTFTANKGGNAFSEVDLPSLEFLDLSRNGLSFKGCCSQSDFGTTS

LKYLDLSFNDVITMSSNFLGLEQLEHLDFQHSNLKQMSQFSVFLSLRNLI

YLDISHTHTRVAFNGIFDGLLSLKVLKMAGNSFQENFLPDIFTDLKNLTF

LDLSQCQLEQLSPTAFDTLNKLQVLNMSHNNFFSLDTFPYKCLPSLQVLD

YSLNHIMTSNNQELQHFPSSLAFLNLTQNDFACTCEHQSFLQWIKDQRQL

LVEAERMECATPSDKQGMPVLSLNITCQMNKTIIGVSVFSVLVVSVVAVL

VYKFYPHLMLLAGCIKYGRGENIYDAFVIYSSQDEDWVRNELVKNLEEGV

PPFQLCLHYRDFIPGVAIAANIIHEGFHKSRKVIVVVSQHFIQSRWCIFE

YEIAQTWQFLSSRAGIIFIVLQKVEKTLLRQQVELYRLLSRNTYLEWEDS

VLGQHIFWRRLRKALLDGKSWNPEEQ

Antibodies of the invention interfere with or otherwise antagonize signaling via human and/or cynomolgus monkey TLR4 and/or human and/or cynomolgus monkey TLR4/MD-2 complexes. In some embodiments, the antibody binds to an epitope that includes one or more amino acid residues on human and/or cynomolgus monkey TLR4 between residues 289 and 375 of SEQ ID NO: 11-(human TLR4) and/or SEQ ID NO: 77 (cynomolgus TLR4). For example, TLR4 antibodies specifically bind to an epitope that includes residue 349 of SEQ ID NO: 11 (human) and/or SEQ ID NO: 77 (cynomolgus). In some embodiments, the epitope also includes additional residues, for example, residues selected from the group consisting of at least residues 328 and 329 of SEQ ID NO: 11 (human) and/or SEQ ID NO: 77 (cynomolgus); at least residue 351 of SEQ ID NO: 11 (human) and/or SEQ ID NO: 77 (cynomolgus); and at least residues 369 through 371 of SEQ ID NO: 11 (human) and/or SEQ ID NO: 77 (cynomolgus), and any combination thereof.

In some embodiments, the anti-TLR4 antibody or immunologically active fragment thereof is or is derived from monoclonal antibodies recognizing human and/or cynomolgus monkey TLR4/MD-2 receptor expressed on the cell surface. The antibodies are capable of blocking, e.g., neutralizing, receptor activation and subsequent intracellular signaling induced TLR4 ligands, e.g., LPS or any other TLR4 ligand described herein. Antibodies of the invention include antibodies that bind human and cynomolgus monkey TLR4/MD-2 receptor complex and also bind TLR4 independently of the presence of MD-2.

In some embodiments, the anti-TLR4 antibody or immunologically active fragment thereof interferes with or otherwise antagonizes signaling via human and/or cynomolgus monkey TLR4/MD-2 receptor expressed on the cell surface, e.g., by blocking receptor activation and subsequent intracellular signaling induced by LPS. Exemplary monoclonal antibodies of these embodiments include: 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5. The sequences of these antibodies are shown below.

These antibodies have distinct specificities. Some antibodies show specificity for both the human and cynomolgus monkey TLR4 and/or both the human and cynomolgus monkey TLR4/MD-2 receptor complex, and they have been shown to inhibit receptor activation and subsequent intracellular signaling via LPS. For example, 1C12, 1E11, 1E11 N103D, 1E11.C1, 1E11.C2, 1E11.C3, 1E11.C4, 1E11.C5, 1E11.C6, 1E11.C2E1, 1E11.C2E2, 1E11.C2E3, 1E11.C2E4 and 1E11.C2E5 bind both human and cynomolgus monkey TLR4 independently of the presence of human or cynomolgus monkey MD-2. 1A1, 1A6, 1B12, 1C7, 1C10, 1D10 and 1G12 only bind to cynomolgus monkey TLR4 independently of the presence of cynomolgus monkey MD-2. 1E11.E1, 1E11.E2, 1E11.E3, 1E11.E4 and 1E11.E5 bind only to human TLR4 independently of the presence of human MD-2.

In some embodiments, the invention provides an isolated antibody that specifically binds Toll-like receptor 4 (TLR4), wherein the antibody binds to an epitope that includes at least residue 349 of SEQ ID NO: 11 and an epitope that includes at least residue 349 of SEQ ID NO: 77. In some embodiments, the antibody includes a heavy chain with three complementarity determining regions (CDRs) including a variable heavy chain complementarity determining region 1 (CDRH1) amino acid sequence of GYSITGGYS (SEQ ID NO: 49); a variable heavy chain complementarity determining region 2 (CDRH2) amino acid sequence of IHYSGYT (SEQ ID NO: 56); and a variable heavy chain complementarity determining region 3 (CDRH3) amino acid sequence of ARKDSG($X_1$)($X_2$)($X_3$)PY (SEQ ID NO: 57), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 68); a variable light chain complementarity determining region 2 (CDRL2) amino acid sequence of YAS (SEQ ID NO: 69); and a variable light chain complementarity determining region 3 (CDRL3) amino acid sequence of QQGHSFPLT (SEQ ID NO: 6). In some embodiments, the epitope further includes at least residues 328 and 329 of SEQ ID NO: 11 and SEQ ID NO: 77. In some embodiments, the epitope further includes at least residue 351 of SEQ ID NO: 11 and SEQ ID NO: 77. In some embodiments, the epitope further includes one or more residues between residues 369 through 371 of SEQ ID NO: 11 and SEQ ID NO: 77. In some embodiments, the epitope further includes at least residues 369 through 371 of SEQ ID NO: 11 and SEQ ID NO: 77. In some embodiments, the antibody specifically binds to an epitope that includes at least residues 328, 329, 349, 351 and 369 through 371 of SEQ ID NO: 11 and SEQ ID NO: 77. In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine.

In some embodiments, the three heavy chain CDRs include an amino acid sequence at least 90%, 91%, 92%, 93%, 94%, 95%, 96%, 97% 98%, 99% or more identical to a variable heavy chain complementarity determining region 1 (VH CDR1, also referred to herein as CDRH1) amino acid sequence selected from the group consisting of G(F/Y)PI(R/G/W)(Y/F/G)GYS (SEQ ID NO: 48), GYSITGGYS (SEQ ID NO: 49); GFPIRYGYS (SEQ ID NO: 50); GYPIRFGYS (SEQ ID NO: 51); GYPIRHGYS (SEQ ID NO: 52); GFPIGQGYS (SEQ ID NO: 53); GYPIWGGYS (SEQ ID NO: 54) and GYPIGGGYS (SEQ ID NO: 55), a variable heavy chain complementarity determining region 2 (VH CDR2, also referred to herein as CDRH2) amino acid sequence of IHYSGYT (SEQ ID NO: 56); and a variable heavy chain complementarity determining region 3 (VH CDR3, also referred to herein as CDRH3) amino acid sequence selected from the group consisting of ARKDSG(N/Q/D/E)$X_1X_2$PY (SEQ ID NO: 57) where $X_1$ and $X_2$ are each independently any hydrophobic amino acid, ARKDSGNYFPY (SEQ ID NO: 58); ARKDSGRLLPY (SEQ ID NO: 59); ARKDSGKWLPY (SEQ ID NO: 60); ARKDSGHLMPY (SEQ ID NO: 61); ARKDSGHNYPY (SEQ ID NO: 62); ARKDSGKNFPY (SEQ ID NO: 63); ARKDSGQLFPY (SEQ ID NO: 64); ARKDSGHNLPY (SEQ ID NO: 65); ARKDSGDYFPY (SEQ ID NO 66) and ARKDSGRYWPY (SEQ ID NO: 67). The three light chain CDRs include an amino acid sequence at least 90%, 91%, 92%, 93%, 94%, 95%, 96%, 97% 98%, 99% or more identical to a variable light chain complementarity determining region 1 (VL CDR1, also referred to herein as CDRL1) amino acid sequence of QSISDH (SEQ ID NO: 68); a variable light chain complementarity determining region 2 (VL CDR2, also referred to herein as CDRL2) amino acid sequence of YAS (SEQ ID NO: 69); and a variable light chain complementarity determining region 3 (VL CDR3, also referred to herein as CDRL3) amino acid sequence selected from the group consisting of QQG(Y/N)(D/E)(F/Y)PXT (SEQ ID NO: 70) where X is any hydrophobic amino acid, QQGHSFPLT (SEQ ID NO: 6); QQGNDFPVT (SEQ ID NO: 71); QQGYDEPFT (SEQ ID NO: 72); QQGYDFPLT (SEQ ID NO: 73); QQGYDYPLT (SEQ ID NO: 74) and QQGYEFPLT (SEQ ID NO: 75). The antibodies bind to human and cynomolgus monkey TLR4/MD-2 complex, to human and cynomolgus TLR4 when not complexed with human and cynomolgus MD-2, to human TLR4/MD-2 complex, to human TLR4 when not complexed with human MD-2, to cynomolgus monkey TLR4/MD-2 complex or cynomolgus TLR4 when not complexed with cynomolgus MD-2.

An exemplary TLR4 monoclonal antibody is the 1E11 antibody described herein. As shown below, the 1E11 antibody includes a heavy chain variable region (SEQ ID NO: 79) encoded by the nucleic acid sequence shown in SEQ ID NO: 78, and a light chain variable region (SEQ ID NO: 81) encoded by the nucleic acid sequence shown in SEQ ID NO: 80.

>1E11 VH nucleic acid sequence
(SEQ ID NO: 78)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11 VH amino acid sequence
(SEQ ID NO: 79)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11 VL nucleic acid sequence
(SEQ ID NO: 80)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11 VL amino acid sequence
(SEQ ID NO: 81)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11 antibody have the following sequences: GYSITGGYS (SEQ ID NO: 49); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1A1 antibody described herein.

>1A1 VH nucleic acid sequence
(SEQ ID NO: 82)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

-continued
GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGCCGCCTCCTCCCTTACTGGGGCCAAGGGACTCTGGTCACTGTCTC

TTCC

>1A1 VH amino acid sequence
(SEQ ID NO: 83)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGRLLPYWGQGTLVTVSS

>1A1 VL nucleic acid sequence
(SEQ ID NO: 84)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1A1 VL amino acid sequence
(SEQ ID NO: 85)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A1 antibody have the following sequences: GYSITGGYS (SEQ ID NO: 49); IHYSGYT (SEQ ID NO: 56); and ARKDS-GRLLPY (SEQ ID NO: 59). The light chain CDRs of the 1A1 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1A6 antibody described herein.

>1A6 VH nucleic acid sequence
(SEQ ID NO: 86)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCAAGTGGTTGCCTTACTGGGGCCAAGGGACTCTGGTCACTGTCTC

TTCC

>1A6 VH amino acid sequence
(SEQ ID NO: 87)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGKWLPYWGQGTLVTVSS

>1A6 VL nucleic acid sequence
(SEQ ID NO: 88)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1A6 VL amino acid sequence
(SEQ ID NO: 89)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 49); IHYSGYT (SEQ ID NO: 56); and ARKDS-GKWLPY (SEQ ID NO: 60). The light chain CDRs of the 1A6 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1B12 antibody described herein.

>1B12 VH nucleic acid sequence
(SEQ ID NO: 90)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGGCACCTCATGCCTTACTGGGGCCAAGGGACTCTGGTCACTGTCTC

TTCC

>1B12 VH amino acid sequence
(SEQ ID NO: 91)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHLMPYWGQGTLVTVSS

>1B12 VL nucleic acid sequence
(SEQ ID NO: 92)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1B12 VL amino acid sequence
(SEQ ID NO: 93)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 49); IHYSGYT (SEQ ID NO: 56); and ARKDS-GHLMPY (SEQ ID NO: 61). The light chain CDRs of the 1B12 antibody have the following sequences: QSISDH (SEQ ID NO: 68); YAS (SEQ ID NO: 69); and QQGHSF-PLT (SEQ ID NO: 6).

An exemplary TLR4 monoclonal antibody is the 1C7 antibody described herein.

>1C7 VH nucleic acid sequence
(SEQ ID NO: 94)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGGCACAACTACCCTTACTGGGGCCAAGGGACTCTGGTCACTGTCTC

TTCC

>1C7 VH amino acid sequence
(SEQ ID NO: 95)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHNYPYWGQGTLVTVSS

>1C7 VL nucleic acid sequence
(SEQ ID NO: 96)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1C7 VL amino acid sequence
(SEQ ID NO: 97)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C7 antibody have the following sequences: GYSITGGYS (SEQ ID NO: 49); IHYSGYT (SEQ ID NO: 56); and ARKDS-GHNYPY (SEQ ID NO: 62). The light chain CDRs of the 1C7 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1C10 antibody described herein.

>1C10 VH nucleic acid sequence
(SEQ ID NO: 98)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCAAGAACTTCCCTTACTGGGGCCAAGGGACTCTGGTCACTGTCTC

TTCC

>1C10 VH amino acid sequence
(SEQ ID NO: 99)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGKNFPYWGQGTLVTVSS

>1C10 VL nucleic acid sequence
(SEQ ID NO: 100)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1C10 VL amino acid sequence
(SEQ ID NO: 101)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C10 antibody have the following sequences: GYSITGGYS (SEQ ID NO: 49); IHYSGYT (SEQ ID NO: 56); and ARKDS-GKNFPY (SEQ ID NO: 63). The light chain CDRs of the 1C10 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1C12 antibody described herein.

>1C12 VH nucleic acid sequence
(SEQ ID NO: 102)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCCAGTTGTTCCCTTACTGGGGCCAAGGGACTCTGGTCACTGTCTC

TTCC

>1C12 VH amino acid sequence
(SEQ ID NO: 103)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGQLFPYWGQGTLVTVSS

>1C12 VL nucleic acid sequence
(SEQ ID NO: 104)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1C12 VL amino acid sequence
(SEQ ID NO: 105)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C12 antibody have the following sequences: GYSITGGYS (SEQ ID NO: 49); IHYSGYT (SEQ ID NO: 56); and ARKDS-GQLFPY (SEQ ID NO: 64). The light chain CDRs of the 1C12 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1D10 antibody described herein.

>1D10 VH nucleic acid sequence
(SEQ ID NO: 106)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

AGCGGCCACAACTTGCCTTACTGGGGCCAAGGGACTCTGGTCACTGTCTC

TTCC

>1D10 VH amino acid sequence
(SEQ ID NO: 107)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGHNLPYWGQGTLVTVSS

>1D10 VL nucleic acid sequence
(SEQ ID NO: 108)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1D10 VL amino acid sequence
(SEQ ID NO: 109)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1D10 antibody have the following sequences: GYSITGGYS (SEQ ID NO: 49); IHYSGYT (SEQ ID NO: 56); and ARKDS-GHNLPY (SEQ ID NO: 65). The light chain CDRs of the 1D10 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11 N103D antibody described herein.

>1E11 N103D VH nucleic acid sequence
(SEQ ID NO: 110)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

```
GCTCTGTGACCGCTGTGGACACTGCAGTGTATTACTGTGCGAGAAAAGAT

TCGGGCGACTACTTCCCTTACTGGGGCCAAGGGACTCTGGTCACTGTCTC

TTCC
```

>1E11 N103D VH amino acid sequence
(SEQ ID NO: 111)
```
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGDYFPYWGQGTLVTVSS
```

>1E11 N103D VL nucleic acid sequence
(SEQ ID NO: 112)
```
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA
```

>1E11 N103D VL amino acid sequence
(SEQ ID NO: 113)
```
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11 N103D antibody have the following sequences: GYSITGGYS (SEQ ID NO: 49); IHYSGYT (SEQ ID NO: 56); and ARKDSGDYFPY (SEQ ID NO: 66). The light chain CDRs of the 1E11 N103D antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1G12 antibody described herein.

>1G12 VH nucleic acid sequence
(SEQ ID NO: 114)
```
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCCGGGCGGTACTGGCCTTACTGGGGCCAAGGGACTCTGGTCACTGTCTC

TTCC
```

>1G12 VH amino acid sequence
(SEQ ID NO: 115)
```
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGRYWPYWGQGTLVTVSS
```

>1G12 VL nucleic acid sequence
(SEQ ID NO: 116)
```
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA
```

>1G12 VL amino acid sequence
(SEQ ID NO: 117)
```
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1G12 antibody have the following sequences: GYSITGGYS (SEQ ID NO: 49); IHYSGYT (SEQ ID NO: 56); and ARKDSGRYWPY (SEQ ID NO: 67). The light chain CDRs of the 1E11 N103D antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11.C1 antibody described herein.

>1E11.C1 VH nucleic acid sequence
(SEQ ID NO: 118)
```
CAGGTGCAGCTTCAGGAGTCCGGCCCAGGACTGGTGAAGCCTTCGGACAC

CCTGTCCCTCACCTGCGCTGTCTCTGGTTTCCCGATCCGCTACGGGTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
```

>1E11.C1 VH amino acid sequence
(SEQ ID NO: 119)
```
QVQLQESGPGLVKPSDTLSLTCAVSGFPIRYGYSWHWIRQPPGKGLEWMG

YIHYSGYTDFNPSLKTRITISRDTSKNQFSLKLSSVTAVDTAVYYCARKD

SGNYFPYWGQGTLVTVSS
```

>1E11.C1 VL amino acid sequence
(SEQ ID NO: 120)
```
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC
```

-continued

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C1 VL amino acid sequence
(SEQ ID NO: 121)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C1 antibody have the following sequences: GFPIRYGYS (SEQ ID NO: 50); IHYSGYT (SEQ ID NO: 56); and ARKDS-GNYFPY (SEQ ID NO: 58). The light chain CDRs of the 1E11.C1 antibody have the following sequences: QSISDH (SEQ ID NO: 68); YAS (SEQ ID NO: 69); and QQGHSF-PLT (SEQ ID NO: 6).

An exemplary TLR4 monoclonal antibody is the 1E11.C2 antibody described herein.

>1E11.C2 VH nucleic acid sequence
(SEQ ID NO: 122)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2 VH amino acid sequence
(SEQ ID NO: 123)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTSS

>1E11.C2 VL nucleic acid sequence
(SEQ ID NO: 124)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C2 VL amino acid sequence
(SEQ ID NO: 125)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2 antibody have the following sequences: GYPIRFGYS (SEQ ID NO: 51); IHYSGYT (SEQ ID NO: 56); and ARKDS-GNYFPY (SEQ ID NO: 58). The light chain CDRs of the 1E11.C1 antibody have the following sequences: QSISDH (SEQ ID NO: 68); YAS (SEQ ID NO: 69); and QQGHSF-PLT (SEQ ID NO: 6).

An exemplary TLR4 monoclonal antibody is the 1E11.C3 antibody described herein.

>1E11.C3 VH nucleic acid sequence
(SEQ ID NO: 126)
CAGGTGCAGCTTCAGGAGTCCGGCCCAGGACTGGTGAAGCCTTCGGACAC

CCTGTCCCTCACCTGCGCTGTCTCTGGTTACCCCATCCGGCACGGGTACA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C3 VH amino acid sequence
(SEQ ID NO: 127)
QVQLQESGPGLVKPSDTLSLTCAVSGYPIRHGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C3 VL nucleic acid sequence
(SEQ ID NO: 128)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C3 VL amino acid sequence
(SEQ ID NO: 129)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C3 antibody have the following sequences: GYPIRHGYS (SEQ ID NO: 52); IHYSGYT (SEQ ID NO: 56); and ARKDS-GNYFPY (SEQ ID NO: 58). The light chain CDRs of the 1E11.C1 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11.C4 antibody described herein.

>1E11.C4 VH nucleic acid sequence
(SEQ ID NO: 130)
CAGGTGCAGCTTCAGGAGTCCGGCCCAGGACTGGTGAAGCCTTCGGACAC

CCTGTCCCTCACCTGCGCTGTCTCTGGTTTCCCGATCGGCCAGGGGTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C4 VH amino acid sequence
(SEQ ID NO: 131)
QVQLQESGPGLVKPSDTLSLTCAVSGFPIGQGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C4 VL nucleic acid sequence
(SEQ ID NO: 132)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C4 VL amino acid sequence
(SEQ ID NO: 133)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C4 antibody have the following sequences: GFPIGQGYS (SEQ ID NO: 53); IHYSGYT (SEQ ID NO: 56); and ARKDSGNYFPY (SEQ ID NO: 58). The light chain CDRs of the 1E11.C1 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11.C5 antibody described herein.

>1E11.C5 VH nucleic acid sequence
(SEQ ID NO: 134)
CAGGTGCAGCTTCAGGAGTCCGGCCCAGGACTGGTGAAGCCTTCGGACAC

CCTGTCCCTCACCTGCGCTGTCTCTGGTTACCCGATCTGGGGGGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCCGCCTCCACC

>1E11.C5 VH amino acid sequence
(SEQ ID NO: 135)
QVQLQESGPGLVKPSDTLSLTCAVSGYPIWGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C5 VL nucleic acid sequence
(SEQ ID NO: 136)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C5 VL amino acid sequence
(SEQ ID NO: 137)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C5 antibody have the following sequences: GYPIWGGYS (SEQ ID NO: 54); IHYSGYT (SEQ ID NO: 56); and ARKDSGNYFPY (SEQ ID NO: 58). The light chain CDRs of the 1E11.C1 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11.C6 antibody described herein.

1E11.C6 VH nucleic acid sequence
(SEQ ID NO: 138)
CAGGTGCAGCTTCAGGAGTCCGGCCCAGGACTGGTGAAGCCTTCGGACAC

CCTGTCCCTCACCTGCGCTGTCTCTGGTTACCCCATCGGCGGCGGCTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C6 VH amino acid sequence
(SEQ ID NO: 139)
QVQLQESGPGLVKPSDTLSLTCAVSGYPIGGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C6 VL nucleic acid sequence
(SEQ ID NO: 140)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGTCACAGTTTTCCGCTCACTTTCGGCGGA

GGGACCAAGGTGGAGATCAAA

>1E11.C6 VL amino acid sequence
(SEQ ID NO: 141)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C6 antibody have the following sequences: GYPIGGGYS (SEQ ID NO: 55); IHYSGYT (SEQ ID NO: 56); and ARKDSGNYFPY (SEQ ID NO: 58). The light chain CDRs of the 1E11.C1 antibody have the following sequences: QSISDH (SEQ ID NO: 68); YAS (SEQ ID NO: 69); and QQGHSFPLT (SEQ ID NO: 6).

An exemplary TLR4 monoclonal antibody is the 1E11.E1 antibody described herein.

>1E11.E1 VH nucleic acid sequence
(SEQ ID NO: 142)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E1 VH amino acid sequence
(SEQ ID NO: 143)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E1 VL nucleic acid sequence
(SEQ ID NO: 144)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGGAACGACTTCCCGGTGACTTTCGGCGGA

GGGACCAAGGTGGAGATCAAA

>1E11.E1 VL amino acid sequence
(SEQ ID NO: 145)
EIVLTQSPDFQSVTPKEKVTITCRASQSISDHLHWYQQKPDQSPKLLIKY

ASHAISGVPSRFSGSGSGTDFTLTINSLEAEDAATYYCQQGNDFPVTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E1 antibody have the following sequences: GYSITGGYS (SEQ ID NO: 49); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGNDFPVT (SEQ ID NO: 71).

An exemplary TLR4 monoclonal antibody is the 1E11.E2 antibody described herein.

>1E11.E2 VH nucleic acid sequence
(SEQ ID NO: 146)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.E2 VH amino acid sequence
(SEQ ID NO: 147)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E2 VL nucleic acid sequence
(SEQ ID NO: 148)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

```
CAACGTATTACTGTCAGCAGGGGTACGACGAGCCGTTCACTTTCGGCGGA

GGGACCAAGGTGGAGATCAAA

>1E11.E2 VL amino acid sequence
                                         (SEQ ID NO: 149)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDEPFTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E2 antibody have the following sequences: GYSITGGYS (SEQ ID NO: 49); IHYSGYT (SEQ ID NO: 56); and ARKDS-GNYFPY (SEQ ID NO: 58). The light chain CDRs of the 1E11 antibody have the following sequences: QSISDH (SEQ ID NO: 68); YAS (SEQ ID NO: 69); and QQGYDEPFT (SEQ ID NO: 72).

An exemplary TLR4 monoclonal antibody is the 1E11.E3 antibody described herein.

```
>1E11.E3 VH nucleic acid sequence
                                         (SEQ ID NO: 150)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
>1E11.E3 VH amino acid sequence
                                         (SEQ ID NO: 151)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E3 VL nucleic acid sequence
                                         (SEQ ID NO: 152)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTTCCCGTTGACTTTCGGCGGA

GGGACCAAGGTGGAGATCAAA

>1E11.E3 VL amino acid sequence
                                         (SEQ ID NO: 153)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDFPLTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E3 antibody have the following sequences: GYSITGGYS (SEQ ID NO: 49); IHYSGYT (SEQ ID NO: 56); and ARKDS-GNYFPY (SEQ ID NO: 58). The light chain CDRs of the 1E11 antibody have the following sequences: QSISDH (SEQ ID NO: 68); YAS (SEQ ID NO: 69); and QQGYDFPLT (SEQ ID NO: 73).

An exemplary TLR4 monoclonal antibody is the 1E11.E4 antibody described herein.

```
>1E11.E4 VH nucleic acid sequence
                                         (SEQ ID NO: 154)
CAGGTGCAGCTTCAGGAGTCCGGCCCAGGACTGGTGAAGCCTTCGGACAC

CCTGTCCCTCACCTGCGCTGTCTCTGGTTACTCCATCACCGGTGGTTATA

GCTGGCACTGGATACGGCAGCCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC
>1E11.E4 VH amino acid sequence
                                         (SEQ ID NO: 155)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.E4 VL nucleic acid sequence
                                         (SEQ ID NO: 156)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTACCCGCTCACTTTCGGCGGA

GGGACCAAGGTGGAGATCAAA

>1E11.E4 VL amino acid sequence
                                         (SEQ ID NO: 157)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDYPLTFGG

GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E4 antibody have the following sequences: GYSITGGYS (SEQ ID NO: 49); IHYSGYT (SEQ ID NO: 56); and ARKDS-GNYFPY (SEQ ID NO: 58). The light chain CDRs of the 1E11 antibody have the following sequences: QSISDH (SEQ ID NO: 68); YAS (SEQ ID NO: 69); and QQGYDYPLT (SEQ ID NO: 74).

An exemplary TLR4 monoclonal antibody is the 1E11.E5 antibody described herein.

>1E11.E5 VH nucleic acid sequence
(SEQ ID NO: 158)
CAGGTGCAGCTTCAGGAGTCCGGCCCAGGACTGGTGAAGCCTTCGGACAC
CCTGTCCCTCACCTGCGCTGTCTCTGGTTACTCCATCACCGGTGGTTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.E5 VH amino acid sequence
(SEQ ID NO: 159)
QVQLQESGPGLVKPSDTLSLTCAVSGYSITGGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.E5 VL nucleic acid sequence
(SEQ ID NO: 160)
GAAATTGTGTTGACGCAGTCTCCAGACTTTCAGTCTGTGACTCCAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC
TGGGACAGACTTCACTCTCACCATCAATAGCCTAGAGGCTGAAGATGCTG
CAACGTATTACTGTCAGCAGGGCTACGAGTTCCCGTTGACTTTCGGCGGA
GGGACCAAGGTGGAGATCAAA >1E11.E5 VL amino acid sequence
(SEQ ID NO: 161)
EIVLTQSPDFQSVTPKEKVTITCRASQSISDHLHWYQQKPDQSPKLLIKY
ASHAISGVPSRFSGSGSGTDFTLTINSLEAEDAATYYCQQGYEFPLTFGG
GTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E5 antibody have the following sequences: GYSITGGYS (SEQ ID NO: 49); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGYEFPLT (SEQ ID NO: 75).

An exemplary TLR4 monoclonal antibody is the 1E11.C2E1 antibody described herein.

>1E11.C2E1 VH nucleic acid sequence
(SEQ ID NO: 162)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E1 VH amino acid sequence
(SEQ ID NO: 163)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E1 VL nucleic acid sequence
(SEQ ID NO: 164)
GAAATTGTGTTGACGCAGTCTCCAGACTTTCAGTCTGTGACTCCAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC
TGGGACAGACTTCACTCTCACCATCAATAGCCTAGAGGCTGAAGATGCTG
CAACGTATTACTGTCAGCAGGGGAACGACTTCCCGGTGACTTTCGGCGGA
GGGACCAAGGTGGAGATCAAA >1E11.C2E1 VL amino acid sequence
(SEQ ID NO: 165)
EIVLTQSPDFQSVTPKEKVTITCRASQSISDHLHWYQQKPDQSPKLLIKY
ASHAISGVPSRFSGSGSGTDFTLTINSLEAEDAATYYCQQGNDFPVTFGG
GTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E1 antibody have the following sequences: GYPIRFGYS (SEQ ID NO: 51); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGNDFPVT (SEQ ID NO: 71).

An exemplary TLR4 monoclonal antibody is the 1E11.C2E3 antibody described herein.

>1E11.C2E3 VH nucleic acid sequence
(SEQ ID NO: 166)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E3 VH amino acid sequence
(SEQ ID NO: 167)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E3 VL nucleic acid sequence
(SEQ ID NO: 168)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTTCCCGTTGACTTTCGGCGGA

GGGACCAAGGTGGAGATCAAA

>1E11.C2E3 VL amino acid sequence
(SEQ ID NO: 169)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E3 antibody have the following sequences: GYPIRFGYS (SEQ ID NO: 51); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGYDFPLT (SEQ ID NO: 73).

An exemplary TLR4 monoclonal antibody is the 1E11.C2E4 antibody described herein.

>1E11.C2E4 VH nucleic acid sequence
(SEQ ID NO: 170)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2E4 VH amino acid sequence
(SEQ ID NO: 171)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2E4 VL nucleic acid sequence
(SEQ ID NO: 172)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGACTACCCGCTCACTTTCGGCGGA

GGGACCAAGGTGGAGATCAAA

>1E11.C2E4 VL amino acid sequence
(SEQ ID NO: 173)
EIVLTQSPDFQSVTPKEKVTITCRASQSISDHLHWYQQKPDQSPKLLIKY

ASHAISGVPSRFSGSGSGTDFTLTINSLEAEDAATYYCQQGYDYPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E4 antibody have the following sequences: GYPIRFGYS (SEQ ID NO: 51); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGYDYPLT (SEQ ID NO: 74).

An exemplary TLR4 monoclonal antibody is the 1E11.C2E5 antibody described herein.

>1E11.C2E5 VH nucleic acid sequence
(SEQ ID NO: 174)
CAGGTGCAGCTTCAGGAGTCCGGCCCAGGACTGGTGAAGCCTTCGGACAC

CCTGTCCCTCACCTGCGCTGTCTCTGGTTACCCGATCCGGTTCGGCTATA

GCTGGCACTGGATACGGCAGCCCCAGGGAAGGGACTGGAGTGGATGGGG

TATATCCACTACAGTGGTTACACTGACTTCAACCCCTCCCTCAAGACTCG

AATCACCATATCACGTGACACGTCCAAGAACCAGTTCTCCCTGAAGCTGA

GCTCTGTGACCGCTGTGGACACTGCAGTGTATTACTGTGCGAGAAAAGAT

TCGGGCAACTACTTCCCTTACTGGGGCCAAGGGACTCTGGTCACTGTCTC

TTCC

>1E11.C2E5 VH amino acid sequence
(SEQ ID NO: 175)
QVQLQESGPGLVKPSDTLSLTCAVSGYPIRFGYSWHWIRQPPGKGLEWMG

YIHYSGYTDFNPSLKTRITISRDTSKNQFSLKLSSVTAVDTAVYYCARKD

SGNYFPYWGQGTLVTVSS

>1E11.C2E5 VL nucleic acid sequence
(SEQ ID NO: 176)
GAAATTGTGTTGACGCAGTCTCCAGACTTTCAGTCTGTGACTCCAAAGGA

AAAAGTCACCATCACCTGCAGGGCCAGTCAGAGTATCAGCGACCACTTAC

ACTGGTACCAACAGAAACCTGATCAGTCTCCCAAGCTCCTCATCAAATAT

GCTTCCCATGCCATTTCTGGGGTCCCATCGAGGTTCAGTGGCAGTGGGTC

TGGGACAGACTTCACTCTCACCATCAATAGCCTAGAGGCTGAAGATGCTG

CAACGTATTACTGTCAGCAGGGCTACGAGTTCCCGTTGACTTTCGGCGGA

GGGACCAAGGTGGAGATCAAA

>1E11.C2E5 VL amino acid sequence
(SEQ ID NO: 177)
EIVLTQSPDFQSVTPKEKVTITCRASQSISDHLHWYQQKPDQSPKLLIKY

ASHAISGVPSRFSGSGSGTDFTLTINSLEAEDAATYYCQQGYEFPLTFGG

GTKVEIK

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E5 antibody have the following sequences: GYPIRFGYS (SEQ ID NO: 51); IHYSGYT (SEQ ID NO: 56); and ARKDSGNYFPY (SEQ ID NO: 58). The light chain CDRs of the 1E11 antibody have the following sequences: QSISDH (SEQ ID NO: 68); YAS (SEQ ID NO: 69); and QQGYEFPLT (SEQ ID NO: 75).

In some embodiments, the TLR4 antibodies are formatted in an IgG isotype. In some embodiments, the TLR4 antibodies are formatted in an IgG1 isotype.

An exemplary IgG1-formatted antibody is the IgG1-formatted 1E11 antibody comprising the heavy chain sequence of SEQ ID NO: 178 and the light chain sequence of SEQ ID NO: 179, as shown below:

```
>1E11 Heavy Chain Amino Acid Sequence
                                    (SEQ ID NO: 178)
QVQLQESGPGLVKPSDTLSLTCAVSGYSITGGYSWHWIRQPPGKGLEWMG

YIHYSGYTDFNPSLKTRITISRDTSKNQFSLKLSSVTAVDTAVYYCARKD

SGNYFPYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG

>1E11 Light Chain Amino Acid Sequence
                                    (SEQ ID NO: 179)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

>1E11 Light Chain Nucleic Acid Sequence
                                    (SEQ ID NO: 180)
ATGAGTGTGCCCACTCAGGTCCTGGGGTTGCTGCTGCTGTGGCTTACAGA

TGCCAGATGTGAAATTGTGTTGACGCAGTCTCCAGACTTTCAGTCTGTGA

CTCCAAAGGAAAAAGTCACCATCACCTGCAGGGCCAGTCAGAGTATCAGC

GACCACTTACACTGGTACCAACAGAAACCTGATCAGTCTCCCAAGCTCCT

CATCAAATATGCTTCCCATGCCATTTCTGGGGTCCCATCGAGGTTCAGTG

GCAGTGGGTCTGGGACAGACTTCACTCTCACCATCAATAGCCTAGAGGCT

GAAGATGCTGCAACGTATTACTGTCAGCAGGGTCACAGTTTTCCGCTCAC

TTTCGGCGGAGGGACCAAGGTGGAGATCAAACGTACGGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG
```

```
CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAA

>1E11 Heavy Chain Nucleic Acid Sequence
                                    (SEQ ID NO: 181)
ATGGAATGGAGCTGGGTCTTTCTCTTCTTCCTGTCAGTAACTACAGGTGT

CCACCAGGTGCAGCTTCAGGAGTCCGGCCCAGGACTGGTGAAGCCTTCGG

ACACCCTGTCCCTCACCTGCGCTGTCTCTGGTTACTCCATCACCGGTGGT

TATAGCTGGCACTGGATACGGCAGCCCCCAGGGAAGGGACTGGAGTGGAT

GGGGTATATCCACTACAGTGGTTACACTGACTTCAACCCCTCCCTCAAGA

CTCGAATCACCATATCACGTGACACGTCCAAGAACCAGTTCTCCCTGAAG

CTGAGCTCTGTGACCGCTGTGGACACTGCAGTGTATTACTGTGCGAGAAA

AGATCCGTCCGACGCCTTTCCTTACTGGGGCCAAGGGACTCTGGTCACTG

TCTCTTCCGCCTCCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACAGTCTCGTGGAACTCAGGAGCCCTGACCA

GCGGCGTGCACACCTTCCCGGCTGTCCTACAGTCCTCAGGACTCTACTCC

CTCAGCAGCGTGGTGACTGTGCCCTCCAGCAGCTTGGGCACCCAGACCTA

CATCTGCAACGTGAATCACAAGCCCAGCAACACCAAGGTGGACAAGAGAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAA

GGACACCCTCATGATCTCCCGGACCCCTGAGGTCACATGCGTGGTGGTGG

ACGTGAGCCACGAAGACCCTGAGGTCAAGTTCAACTGGTACGTGGACGGC

GTGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGT

GTATACCCTGCCCCCATCTCGGGAGGAGATGACCAAGAACCAGGTCAGCC

TGACTTGCCTGGTCAAAGGCTTCTATCCCAGCGACATCGCCGTGGAGTGG

GAGAGCAACGGGCAGCCGGAGAACAACTACAAGACCACGCCTCCCGTGCT

GGACTCCGACGGCTCCTTCTTCCTCTATAGCAAGCTCACCGTGGACAAGT

CCAGGTGGCAGCAGGGGAACGTCTTCTCATGCTCCGTGATGCATGAGGCT

CTGCACAACCACTACACGCAGAAGAGCCTCTCCCTGTCTCCGGGTAA
```

An exemplary IgG1-formatted antibody is the IgG1-formatted 1E11.C11 antibody comprising the heavy chain sequence of SEQ ID NO: 182 and the light chain sequence of SEQ ID NO: 183, as shown below:

```
>1E11.C1 Light Chain Amino Acid Sequence
                                    (SEQ ID NO: 182)
EIVLTQSPDFQSVTPKEKVTITCRASQSISDHLHWYQQKPDQSPKLLIKY

ASHAISGVPSRFSGSGSGTDFTLTINSLEAEDAATYYCQQGHSFPLTFGG

GTKVEIKRTVAAPSVFIFPPSDEQLKSGTASVVCLLNNFYPREAKVQWKV
```

```
DNALQSGNSQESVTEQDSKDSTYSLSSTLTLSKADYEKHKVYACEVTHQG

LSSPVTKSFNRGEC

>1E11.C1 Heavy Chain Amino Acid Sequence
                                        (SEQ ID NO: 183)
QVQLQESGPGLVKPSDTLSLTCAVSGFPIRYGYSWHWIRQPPGKGLEWMG

YIHYSGYTDFNPLKTRITISRDTSKNQFSLKLSSVTAVDTAVYYCARKDS

GNYFPYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPG

>1E11.C1 Light Chain Nucleic Acid Sequence
                                        (SEQ ID NO: 184)
ATGAGTGTGCCCACTCAGGTCCTGGGGTTGCTGCTGCTGTGGCTTACAGA

TGCCAGATGTGAAATTGTGTTGACGCAGTCTCCAGACTTTCAGTCTGTGA

CTCCAAAGGAAAAAGTCACCATCACCTGCAGGGCCAGTCAGAGTATCAGC

GACCACTTACACTGGTACCAACAGAAACCTGATCAGTCTCCCAAGCTCCT

CATCAAATATGCTTCCCATGCCATTTCTGGGGTCCCATCGAGGTTCAGTG

GCAGTGGGTCTGGGACAGACTTCACTCTCACCATCAATAGCCTAGAGGCT

GAAGATGCTGCAACGTATTACTGTCAGCAGGGTCACAGTTTTCCGCTCAC

TTTCGGCGGAGGGACCAAGGTGGAGATCAAACGTACGGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAA

>1E11.C1 Heavy Chain Nucleic Acid Sequence
                                        (SEQ ID NO: 185)
ATGGAATGGAGCTGGGTCTTTCTCTTCTTCCTGTCAGTAACTACAGGTGT

CCACCAGGTGCAGCTTCAGGAGTCCGGCCCAGGACTGGTGAAGCCTTCG

ACACCCTGTCCCTCACCTGCGCTGTCTCTGGTTTCCCGATCCGCTACGGG

TATAGCTGGCACTGGATACGGCAGCCCCCAGGGAAGGGACTGGAGTGGAT

GGGGTATATCCACTACAGTGGTTACACTGACTTCAACCCCTCCCTCAAGA

CTCGAATCACCATATCACGTGACACGTCCAAGAACCAGTTCTCCCTGAAG

CTGAGCTCTGTGACCGCTGTGGACACTGCAGTGTATTACTGTGCGAGAAA

AGATTCGGGCAACTACTTCCCTTACTGGGGCCAAGGGACTCTGGTCACTG

TCTCTTCCGCCTCCACCAAGGGCCCATCGGTCTTCCCCCTGGCACCCTCC

TCCAAGAGCACCTCTGGGGGCACAGCGGCCCTGGGCTGCCTGGTCAAGGA

CTACTTCCCCGAACCGGTGACAGTCTCGTGGAACTCAGGAGCCCTGACCA

GCGGCGTGCACACCTTCCCGGCTGTCCTACAGTCCTCAGGACTCTACTCC

CTCAGCAGCGTGGTGACTGTGCCCTCCAGCAGCTTGGGCACCCAGACCTA

CATCTGCAACGTGAATCACAAGCCCAGCAACACCAAGGTGGACAAGAGAG

TTGAGCCCAAATCTTGTGACAAAACTCACACATGCCCACCGTGCCCAGCA

CCTGAACTCCTGGGGGGACCGTCAGTCTTCCTCTTCCCCCCAAAACCCAA

GGACACCCTCATGATCTCCCGGACCCCTGAGGTCACATGCGTGGTGGTGG

ACGTGAGCCACGAAGACCCTGAGGTCAAGTTCAACTGGTACGTGGACGGC

GTGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGGT

GTATACCCTGCCCCCATCTCGGGAGGAGATGACCAAGAACCAGGTCAGCC

TGACTTGCCTGGTCAAAGGCTTCTATCCCAGCGACATCGCCGTGGAGTGG

GAGAGCAACGGGCAGCCGGAGAACAACTACAAGACCACGCCTCCCGTGCT

GGACTCCGACGGCTCCTTCTTCCTCTATAGCAAGCTCACCGTGGACAAGT

CCAGGTGGCAGCAGGGGAACGTCTTCTCATGCTCCGTGATGCATGAGGCT

CTGCACAACCACTACACGCAGAAGAGCCTCTCCCTGTCTCCGGGTTAA
```

In some embodiments, TLR4 antibodies of the invention specifically bind human and/or cynomolgus TLR4/MD-2 complex, wherein the antibody binds to an epitope that includes one or more amino acid residues on human and/or cynomolgus TLR4 between residues 325 and 374 of SEQ ID NO: 11 (human) and SEQ ID NO: 77 (cynomolgus). Alternatively, the monoclonal antibody is an antibody that binds to the same epitope as 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5.

The anti-TLR4 antibodies of the invention include an altered antibody in which at least the amino acid residue at EU position 325 and at least the amino acid residue at EU position 328 in the CH2 domain of the Fc portion of the antibody has been modified. For example, at least the amino acid residue at EU position 325 has been substituted with serine, and at least the amino acid residue at EU position 328 has been substituted with phenylalanine These anti-TLR4 antibodies with a modified Fc portion elicit modified effector functions e.g., a modified Fc receptor activity, as compared to an unaltered antibody. For example, the human Fc receptor is CD32A. In some embodiments, these anti-TLR4 antibodies elicit a prevention of proinflammatory mediators release following ligation to CD32A as compared to an unaltered antibody. Thus, these anti-TLR4 antibodies elicit a modified Fc receptor activity, such as the prevention of proinflammatory mediators release while retaining the ability to bind a target antigen. In some embodiments, these anti-TLR4 antibodies are neutralizing antibodies, wherein the anti-TLR4 antibody elicits a modified Fc receptor activity, while retaining the ability to neutralize one or more biological activities of a target antigen.

For example, anti-TLR4 antibodies of the invention include monoclonal antibodies that bind the human TLR4/MD-2 receptor complex. This receptor complex is activated by lipopolysaccharide (LPS), the major component of the outer membrane of gram-negative bacteria. The anti-TLR4 antibodies of the invention inhibit receptor activation and subsequent intracellular signaling via LPS. Thus, the anti-TLR4 antibodies neutralize the activation of the TLR4/MD-2 receptor complex. In particular, the invention provides anti-TLR4 antibodies that recognize the TLR4/MD-2 receptor complex expressed on the cell surface. These anti-TLR4 antibodies block LPS-induced and other TLR4 ligand-induced pro-inflammatory cytokine (e.g., IL-6, IL-8, TNFα) production. In addition, some anti-TLR4 antibodies of the invention also recognize TLR4 when not complexed with MD-2. The altered antibody is, e.g., a humanized antibody.

Monoclonal antibodies of the invention (e.g., murine monoclonal, humanized antibodies or fully human monoclonal antibodies) specifically bind TLR4. Also included in the invention are antibodies that bind to the same epitope as the antibodies described herein. For example, antibodies of the invention that specifically bind TLR4 and/or the TLR4/MD-2 complex bind to an epitope that includes one or more amino acid residues on human TLR4 (SEQ ID NO: 11)

Those skilled in the art will recognize that it is possible to determine, without undue experimentation, if a monoclonal antibody (e.g., a murine monoclonal or humanized antibody) has the same specificity as a monoclonal antibody described herein by ascertaining whether the former prevents the latter from binding to the TLR4/MD-2 complex or to TLR4 when not complexed to MD-2. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of monoclonal antibody of the invention is to pre-incubate the monoclonal antibody of the invention with the TLR4/MD-2 complex or a soluble TLR4 protein (with which it is normally reactive), and then add the monoclonal antibody being tested to determine if the monoclonal antibody being tested is inhibited in its ability to bind the TLR4/MD-2 complex or to bind TLR4 and TLR4 complexed with MD-2. If the monoclonal antibody being tested is inhibited then, in all likelihood, it has the same, or functionally equivalent, epitopic specificity as the monoclonal antibody of the invention.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; preferably ≤100 nM and most preferably ≤10 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the Toll-like Receptor 4 (TLR4)/MD-2 complex or to TLR4 when not complexed to MD-2, when the equilibrium binding constant ($K_d$) is ≤1 µM, preferably ≤100 nM, more preferably ≤10 nM, and most preferably ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology-A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to TLR4/MD2 complex or TLR4 alone, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p.392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Use of Anti-TLR4 Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an anti-TLR4 antibody, are used to inhibit GvHD and/or improve survival of a GvHD subject.

Efficaciousness of treatment is determined in association with any known method for diagnosing or treating GvHD or other transplant related disorders. Inhibiting GvHD or improving survival of a GvHD subject indicates that the antibody confers a clinical benefit.

Anti-TLR4 antibodies are administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macro emulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Figure 2A:
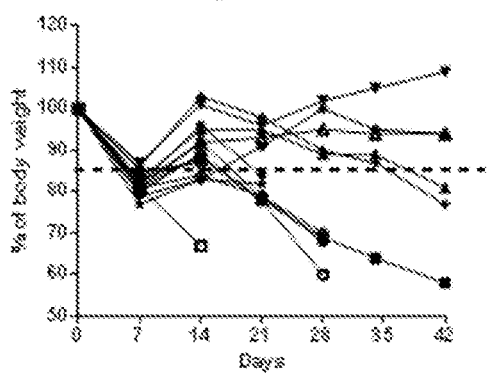
FIGS. 2A, 2B, and 2C are a series of graphs depicting the effect of anti-TLR4 treatment on body weight change of individual mice, in a murine model of GvHD. Note that at day 42, only 3 out of the 15 mice treated with an isotype control had more than 85% of the original body weight (threshold marked with dotted line), whilst 9 out 15 mice from both the prophylactic and therapeutic anti-TLR4 treatment groups were above this value.
Figure 2B:
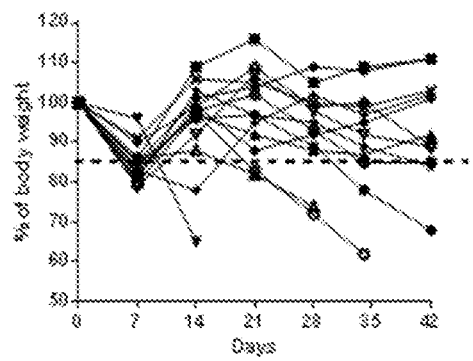
Figure 2C:
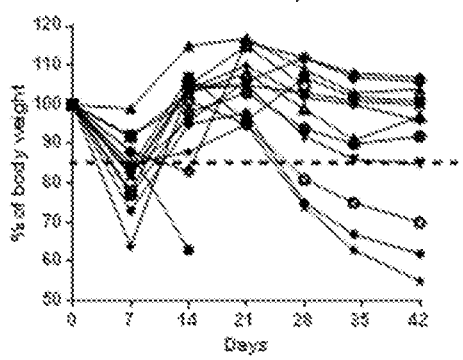

The Examples and data provided herein assess the role of TLR4 blockade in inhibiting GvHD and improving survival of GvHD subjects. Briefly, B6D2F1 and C57BL/6 mice (female, 8 weeks of age) were lethally irradiated and administered $5\times10^6$ bone marrow derived cells and $6\times10^6$ splenocytes from either syngeneic (B6D2F1) or allogeneic (C57Bl/6) donors. Mice transplanted with allogeneic cells were treated intravenously with 100 mg/kg of anti-TLR4 monoclonal antibody, 5E3, or isotype control either prophylactically (day -1, 3, 7, 14, 21, 28 and 35) or therapeutically (day 7, 10, 14, 21, 28 and 35). Body weight (FIGS. 2A, 2B, and 2C) and survival (FIG. 1) were followed weekly starting from day 0 for 6 weeks. Survival data demonstrated that only six out of fifteen mice from isotype control treated group survived 6 weeks post allo-transplantation. In contrast, eleven out of fifteen mice from anti-TLR4 prophylactic treatment group and twelve out fifteen mice from the anti-TLR4 therapeutic treatment group survived 6 weeks post allo-transplantation. The survival rate improved from 40% of the isotype control group to 73% of the anti-TLR4 prophylactic group and 80% of the anti-TLR4 therapeutic group 6 weeks post allo-transplantation. These results demonstrate that TLR4 blockade can efficiently inhibit GvHD and improve survival of the GvHD subjects.

While the studies described herein use allogeneic bone marrow cells, the materials, methods, and examples are illustrative only and are not intended to be limiting.

Materials and Methods for the Generation of 5E3 Monoclonal Antibody:

The 5E3 monoclonal antibody is a monoclonal antibody that binds mouse TLR4. (See Daubeuf et al., "TLR4/MD-2 Monoclonal Antibody Therapy Affords Protection in Experimental Models of Septic Shock," J Immunol vol. 179:6107-6114 (1997).

Animals:

B6D2F1 and C57BL/6 mice (female, 8 weeks of age) were purchased from Charles River laboratories and housed in a conventional facility with free access to food and water. All experiments were conducted under protocols reviewed and approved by institutional animal care and use committee.

Isolation of Mouse Bone Marrow Cells:

Place the femurs from the donor B6D2F1 and C57BL/6 mice in a small dish (35×10 mm) on ice containing RPMI 1640+2% FBS. Flush the femurs with 10 ml of RPMI+2% FBS using a 26G needle. Pipette cells up and down several times to disperse aggregates. Pass the cells through a sterile 40-μm nylon Cell Strainer (Falcon 352340). Bring the volume to 50 ml with medium and centrifuge at 2000 rpm (900×g), 10 min, 4° C. Wash the cell pellet twice with 50 ml of serum-free RPMI. Centrifuge at 2000 rpm, 5 min, 4° C. Resuspend cells in 20 ml medium and count cells. Centrifuge again and resuspend cells to $5 \times 10^7$ cells/ml.

Isolation of Mouse Splenocytes:

Place the femurs from the donor B6D2F1 and C57BL/6 mice in a small dish (35×10 mm) on ice containing RPMI 1640+2% FBS. Move the spleen to a sterile wire mesh screen (200 um bar width and 340 um open space). Gently push the spleen through the screen with the plunger of a 10 ml syringe into the petri dish. Rinse the screen with 3 ml of RPMI 1640+2% FBS. Transfer the cell suspension to a centrifuge tube and centrifuge to pellet the cells. Lyse the red blood cells using ACK (Ammonium-Chloride-Potassium) Lysing Buffer (1 ml of Tris-NH4Cl per 0.1 ml of packed cells for 2 min at room temperature. Wash cells three times with medium, count cells and resuspend cells to $6 \times 10^7$ cells/ml.

Allo-Bone Marrow Transplantation:

Recipient B6D2F1 female mice were immobilized in individual boxes and exposed to 900 rads administered over 9 minutes utilizing a gamma irradiator. Isolated bone marrow cells and splenocytes from the same donor mouse (from B6D2F1 for syngeneic and from C57BL/6 for allogeneic) were mixed 1:1 in volume and 200 μl of the cell mix (containing $5 \times 10^6$ bone marrow derived cells and $6 \times 10^6$ splenocytes) was administered into the irradiated recipients.

Administration of Monoclonal Antibodies:

B6D2F1 mice transplanted with allogeneic cells (from C57BL/6) were treated intravenously (i.v.) with 100 mg/kg of anti-TLR4 monoclonal antibody, 5E3, or isotype control either prophylactically (day −1, 3, 7, 14, 21, 28 and 35) or therapeutically (day 7, 10, 14, 21, 28 and 35). On the days specified above and immediately prior to the administration of the antibodies, the antibodies were thawed at room temperature and diluted with PBS to reach required antibody concentrations for injection. Mice were injected with 200 μl of antibody/PBS solution (i.v.). Body weight and survival were followed weekly starting from day 0 for 6 weeks.

Statistical Analysis:

Statistical analysis was performed using GraphPad Prism version 5.0d. Survival curves were analyzed by Log-rank (Mantel-Cox) test in comparison to the isotype control treated allo-transplantation group. The p-values were shown in the figures.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preventing or reducing the likelihood of Graft-versus-Host disease (GvHD) in a human subject in need of an allogeneic stem cell transplant comprising:
(i) contacting a stem cell population that is allogeneic to said human subject with an antibody or immunologically active fragment thereof that specifically binds a human Toll-like receptor 4 (TLR4) polypeptide comprising a variable heavy chain complementarity determining region 1 ($V_H$ CDR1) comprising the amino acid sequence of GGYSWH (SEQ ID NO: 1); a $V_H$ CDR2 region comprising the amino acid sequence of YIHYSGYTDFNPSLKT (SEQ ID NO: 2); a $V_H$ CDR3 region comprising the amino acid sequence of KDPSDAFPY (SEQ ID NO: 3); a variable light chain complementarity determining region 1 ($V_L$ CDR1) region comprising the amino acid sequence of RASQSISDHLH (SEQ ID NO: 4); a $V_L$ CDR2 region comprising the amino acid sequence of YASHAIS (SEQ ID NO: 5); and a $V_L$ CDR3 region comprising the amino acid sequence of QQGHSFPLT (SEQ ID NO: 6), to produce a transplantable composition; and
(ii) implanting the transplantable composition at a desired location in the subject.

2. The method of claim 1, further comprising:
(iii) administering to the subject one or more doses of the antibody or immunologically active fragment thereof of step (i) in an amount sufficient to prevent or reduce the likelihood of GvHD in said human subject.

3. The method of claim 1 or 2, wherein allogeneic stem cell transplant is a bone marrow derived stem cell transplant or hematopoietic stem cell transplant.

4. The method of claim 2, where the antibody or immunologically active fragment thereof that specifically binds TLR4 in steps (i) and (iii) are the same antibody or immunologically active fragment.

5. The method of claim 2, where the antibody or immunologically active fragment thereof that specifically binds TLR4 in step (i) and the antibody or immunologically active fragment thereof that specifically binds TLR4 in step (iii) are different antibodies or immunologically active fragments.

6. The method of claim 2, wherein the antibody or immunologically active fragment thereof that specifically binds TLR4 is administered in step (iii) in combination with one or more additional agents.

7. The method of claim 6, wherein the one or more additional agents is one or more immunosuppressive agents.

8. The method of claim 6, wherein the one or more additional agents is selected from methotrexate, cyclosporin A, tacrolimus, sirolimus, everolimus, a corticosteroid, anti-thymocyte globulin, Infliximab, Etanercept and Adalimumab.

9. The method of claim 1 or 2, wherein the antibody or immunologically active fragment thereof that binds TLR4 is a mouse monoclonal antibody, a chimeric monoclonal antibody, a humanized monoclonal antibody, a fully human monoclonal antibody, a domain antibody, a single chain antibody, a $F_{ab}$ fragment, a $F_{ab'}$ fragment, a $F_{(ab')2}$ fragment, an scFv or an $F_{ab}$ expression library.

10. The method of claim 1 or 2, wherein the antibody or immunologically active fragment thereof that binds TLR4 further comprises a heavy chain variable amino acid sequence of QVQLQESGPGLVKPSDTLSLTCAVSGYSITGGYSWHWIRQPPGKGLEWMGYIHYSGYTDFNPSLKTRITISRDTSKNQFSLKLSSVTAVDTAVYYCARKDPSDAFPYWGQGTLVTVSS (SEQ ID NO: 7) and a light chain variable amino acid sequence of EIVLTQSPDFQSVTPKEKVTITCRASQSISDHLHWYQQKPDQSPKLLIKYASHAISGVPSR FSGSGSGTDFTLTINSLEAEDAATYYCQQGHSFPLTFGGGTKVEIK (SEQ ID NO: 8).

11. The method of claim 1 or 2, wherein the antibody or immunologically active fragment thereof that binds TLR4 further comprises a heavy chain amino acid sequence of MGWSWIFLFLLSGTAGVHCQVQLQESGPGLVKPSDTLSLTCAVSGYSITGGYSWHWIR QPPGKGLEWMGYIHYSGYTDFNPSLKTRITISRDTSKNQFSLKLSSVTAVDTAVYYCAR KDPSDAFPYWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKRVE PKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSSKAFPAPIE KTISKAKGQPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPGK (SEQ ID NO: 9) and a light chain amino acid sequence of MEWSWVFLFFLSVTTGVHSEIVLTQSPDFQSVTPKEKVTITCRASQSISDHLHWYQQKPD QSPKLLIKYASHAISGVPSRFSGSGSGTDFTLTINSLEAEDAATYYCQQGHSFPLTFGGGT KVEIKRTVAAPSVFIFPPSDEQLKSGTASVVCLLNNFYPREAKVQWKVDNALQSGNSQE SVTEQDSKDSTYSLSSTLTLSKADYEKHKVY-ACEVTHQGLSSPVTKSFNRGEC (SEQ ID NO: 10).

12. A method of preventing or reducing the likelihood of GvHD in a human subject who has received or will receive an allogeneic stem cell transplant comprising administering to the subject one or more doses of an antibody or immunologically an antibody or immunologically active fragment thereof that specifically binds a human Toll-like receptor 4 (TLR4) polypeptide comprising a variable heavy chain complementarity determining region 1 ($V_H$ CDR1) comprising the amino acid sequence of GGYSWH (SEQ ID NO: 1); a $V_H$ CDR2 region comprising the amino acid sequence of YIHYSGYTDFNPSLKT (SEQ ID NO: 2); a $V_H$ CDR3 region comprising the amino acid sequence of KDPSDAFPY (SEQ ID NO: 3); a variable light chain complementarity determining region 1 ($V_L$ CDR1) region comprising the amino acid sequence of RASQSISDHLH (SEQ ID NO: 4); a $V_L$ CDR2 region comprising the amino acid sequence of YASHAIS (SEQ ID NO: 5); and a $V_L$ CDR3 region comprising the amino acid sequence of QQGHSF- PLT (SEQ ID NO: 6) in an amount sufficient to prevent or reduce the likelihood of GvHD in said human subject.

13. The method of claim 12, wherein allogeneic stem cell transplant is a bone marrow derived stem cell transplant or hematopoietic stem cell transplant.

14. The method of claim 12, wherein the antibody or immunologically active fragment thereof that specifically binds TLR4 is administered in combination with one or more additional agents.

15. The method of claim 14, wherein the one or more additional agents is one or more immunosuppressive agents.

16. The method of claim 15, wherein the one or more additional agents is selected from methotrexate, cyclosporin A, tacrolimus, sirolimus, everolimus, a corticosteroid, anti-thymocyte globulin, Infliximab, Etanercept and Adalimumab.

17. The method of claim 12, wherein the antibody or immunologically active fragment thereof that binds TLR4 is a mouse monoclonal antibody, a chimeric monoclonal antibody, a humanized monoclonal antibody, a fully human monoclonal antibody, a domain antibody, a single chain antibody, a $F_{ab}$ fragment, a $F_{ab'}$ fragment, a $F_{(ab')2}$ fragment, an scFv or an $F_{ab}$ expression library.

18. The method of claim 12, wherein the antibody or immunologically active fragment thereof that binds TLR4 further comprises the heavy chain variable amino acid sequence QVQLQESGPGLVKPSDTLSLTCAVSGYSITGGYSWHWIRQPPGKGLEWMGYIHYSGYT DFNPSLKTRITISRDTSKNQFSLKLSSVTAVDTAVYYCARKDPSDAFPYWGQGTLVTVSS (SEQ ID NO: 7) and the light chain variable amino acid sequence EIVLTQSPDFQSVTPKEKVTITCRASQSISDHLHWYQQKPDQSPKLLIKYASHAISGVPSR FSGSGSGTDFTLTINSLEAEDAATYYCQQGHSFPLTFGGGTKVEIK (SEQ ID NO: 8).

19. The method of claim 12, wherein the antibody or immunologically active fragment thereof that binds TLR4 further comprises the heavy chain amino acid sequence MGWSWIFLFLLSGTAGVHCQVQLQESGPGLVKPSDTLSLTCAVSGYSITGGYSWHWIR QPPGKGLEWMGYIHYSGYTDFNPSLKTRITISRDTSKNQFSLKLSSVTAVDTAVYYCAR KDPSDAFPYWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKRVE PKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSSKAFPAPIE KTISKAKGQPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPGK(SEQ ID NO: 9) and the light chain amino acid sequence MEWSWVFLFFLSVTTGVHSEIVLTQSPDFQSVTPKEKVTITCRASQSISDHLHWYQQKPD QSPKLLIKYASHAISGVPSRFSGSGSGTDFTLTINSLEAEDAATYYCQQGHSFPLTFGGGT KVEIKRTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC(SEQ ID NO: 10).

* * * * *

SEQUENCE LISTING

```
<160> NUMBER OF SEQ ID NOS: 185

<210> SEQ ID NO 1
<211> LENGTH: 6
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 1

Gly Gly Tyr Ser Trp His
1               5

<210> SEQ ID NO 2
<211> LENGTH: 16
<212> TYPE: PRT
<213> ORGANISM: Artificial Sequence
<220> FEATURE:
<223> OTHER INFORMATION: anti-TLR4 variable heavy chain complementarity
      determining region 2

<400> SEQUENCE: 2

Tyr Ile His Tyr Ser Gly Tyr Thr Asp Phe Asn Pro Ser Leu Lys Thr
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 3
```

```
<400> SEQUENCE: 3

Lys Asp Pro Ser Asp Ala Phe Pro Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: anti-TLR4 variable light chain complementarity
      determining region 1

<400> SEQUENCE: 4

Arg Ala Ser Gln Ser Ile Ser Asp His Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: anti-TLR4 variable light chain complementarity
      determining region 2

<400> SEQUENCE: 5

Tyr Ala Ser His Ala Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 6

Gln Gln Gly His Ser Phe Pro Leu Thr
1               5

<210> SEQ ID NO 7
<211> LENGTH: 118
<212> TYPE: PRT
<213> ORGANISM: Artificial Sequence
<220> FEATURE:
<223> OTHER INFORMATION: anti-TLR4 variable heavy chain

<400> SEQUENCE: 7

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
```

<210> SEQ ID NO 8
<211> LENGTH: 107
<212> TYPE: PRT
<213> ORGANISM: Artificial Sequence
<220> FEATURE:
<223> OTHER INFORMATION: anti-TLR4 variable light chain

<400> SEQUENCE: 8

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105
```

<210> SEQ ID NO 9
<211> LENGTH: 467
<212> TYPE: PRT
<213> ORGANISM: Artificial Sequence
<220> FEATURE:
<223> OTHER INFORMATION: anti-TLR4 heavy chain

<400> SEQUENCE: 9

```
Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30

Pro Ser Asp Thr Leu Ser Leu Thr Cys Ala Val Ser Gly Tyr Ser Ile
        35                  40                  45

Thr Gly Gly Tyr Ser Trp His Trp Ile Arg Gln Pro Pro Gly Lys Gly
    50                  55                  60

Leu Glu Trp Met Gly Tyr Ile His Tyr Ser Gly Tyr Thr Asp Phe Asn
65                  70                  75                  80

Pro Ser Leu Lys Thr Arg Ile Thr Ile Ser Arg Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Arg Lys Asp Pro Ser Asp Ala Phe Pro Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Ser Lys Ala Phe Pro Ala Pro Ile
                340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 10
<211> LENGTH: 233
<212> TYPE: PRT
<213> ORGANISM: Artificial Sequence
<220> FEATURE:
<223> OTHER INFORMATION: anti-TLR4 light chain

<400> SEQUENCE: 10

Met Glu Trp Ser Trp Val Phe Leu Phe Phe Leu Ser Val Thr Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Ser Asp His Leu His Trp Tyr Gln Gln Lys Pro Asp Gln Ser Pro Lys
    50                  55                  60

Leu Leu Ile Lys Tyr Ala Ser His Ala Ile Ser Gly Val Pro Ser Arg
65                  70                  75                  80
```

```
Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys Gln Gln Gly His Ser
            100                 105                 110

Phe Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 11
<211> LENGTH: 839
<212> TYPE: PRT
<213> ORGANISM: Homo sapiens

<400> SEQUENCE: 11

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Leu Glu Asn Phe
        130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
210                 215                 220
```

```
Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
            245                 250                 255

Arg Leu Val Leu Gly Glu Phe Arg Asn Glu Gly Asn Leu Glu Lys Phe
        260                 265                 270

Asp Lys Ser Ala Leu Glu Gly Leu Cys Asn Leu Thr Ile Glu Glu Phe
    275                 280                 285

Arg Leu Ala Tyr Leu Asp Tyr Tyr Leu Asp Asp Ile Ile Asp Leu Phe
290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640
```

```
Val Leu Val Val Ser Val Ala Val Leu Val Tyr Lys Phe Tyr Phe
                645                 650                 655
His Leu Met Leu Leu Ala Gly Cys Ile Lys Tyr Gly Arg Gly Glu Asn
        660                 665                 670
Ile Tyr Asp Ala Phe Val Ile Tyr Ser Ser Gln Asp Glu Asp Trp Val
    675                 680                 685
Arg Asn Glu Leu Val Lys Asn Leu Glu Glu Gly Val Pro Pro Phe Gln
690                 695                 700
Leu Cys Leu His Tyr Arg Asp Phe Ile Pro Gly Val Ala Ile Ala Ala
705                 710                 715                 720
Asn Ile Ile His Glu Gly Phe His Lys Ser Arg Lys Val Ile Val
                725                 730                 735
Val Ser Gln His Phe Ile Gln Ser Arg Trp Cys Ile Phe Glu Tyr Glu
            740                 745                 750
Ile Ala Gln Thr Trp Gln Phe Leu Ser Ser Arg Ala Gly Ile Ile Phe
        755                 760                 765
Ile Val Leu Gln Lys Val Glu Lys Thr Leu Leu Arg Gln Gln Val Glu
    770                 775                 780
Leu Tyr Arg Leu Leu Ser Arg Asn Thr Tyr Leu Glu Trp Glu Asp Ser
785                 790                 795                 800
Val Leu Gly Arg His Ile Phe Trp Arg Arg Leu Arg Lys Ala Leu Leu
                805                 810                 815
Asp Gly Lys Ser Trp Asn Pro Glu Gly Thr Val Gly Thr Gly Cys Asn
            820                 825                 830
Trp Gln Glu Ala Thr Ser Ile
        835

<210> SEQ ID NO 12
<211> LENGTH: 1404
<212> TYPE: DNA
<213> ORGANISM: Artificial Sequence
<220> FEATURE:
<223> OTHER INFORMATION: NI-0101 heavy chain

<400> SEQUENCE: 12
atgggatgga gctggatctt tctcttcctc ctgtcaggaa ctgcaggtgt acattgccag      60
gtgcagcttc aggagtccgg cccaggactg gtgaagcctt cggacaccct gtccctcacc     120
tgcgctgtct ctggttactc catcaccggt ggttatagct ggcactggat acggcagccc     180
ccagggaagg gactggagtg gatggggtat atccactaca gtggttacac tgacttcaac     240
ccctccctca gactcgaat caccatatca cgtgacacgt ccaagaacca gttctccctg      300
aagctgagct ctgtgaccgc tgtggacact gcagtgtatt actgtgcgag aaaagatccg     360
tccgacgcct tccttactg gggccaaggg actctggtca ctgtctcttc cgcctccacc      420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgccc accgtgccca gcacctgaac tcctgggggg accgtcagtc     780
ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900
```

| | |
|---|---|
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaaa | 1020 |
| tgcaaggtct ccagtaaagc tttccctgcc cccatcgaga aaaccatctc caaagccaaa | 1080 |
| gggcagcccc gagaaccaca ggtgtacacc ctgcccccat cccgggagga tgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta tagcaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggtaa atag | 1404 |

<210> SEQ ID NO 13
<211> LENGTH: 702
<212> TYPE: DNA
<213> ORGANISM: Artificial Sequence
<220> FEATURE:
<223> OTHER INFORMATION: NI-0101 light chain

<400> SEQUENCE: 13

| | |
|---|---|
| atggaatgga gctgggtctt tctcttcttc ctgtcagtaa ctacaggtgt ccactccgaa | 60 |
| attgtgttga cgcagtctcc agactttcag tctgtgactc caaaggaaaa agtcaccatc | 120 |
| acctgcaggg ccagtcagag tatcagcgac cacttacact ggtaccaaca gaaacctgat | 180 |
| cagtctccca agctcctcat caaatatgct tcccatgcca tttctggggt cccatcgagg | 240 |
| ttcagtggca gtgggtctgg gacagacttc actctcacca tcaatagcct agaggctgaa | 300 |
| gatgctgcaa cgtattactg tcagcagggt cacagttttc cgctcacttt cggcggaggg | 360 |
| accaaggtgg agatcaaacg tacggtggct gcaccatctg tcttcatctt cccgccatct | 420 |
| gatgagcagt tgaaatctgg aactgcctct gttgtgtgcc tgctgaataa cttctatccc | 480 |
| agagaggcca aagtacagtg gaaggtggat aacgccctcc aatcgggtaa ctcccaggag | 540 |
| agtgtcacag agcaggacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgtt ag | 702 |

<210> SEQ ID NO 14
<211> LENGTH: 118
<212> TYPE: PRT
<213> ORGANISM: Artificial Sequence
<220> FEATURE:
<223> OTHER INFORMATION: 15C1 Hu VH version 4-28
<220> FEATURE:
<221> NAME/KEY: misc_feature
<222> LOCATION: (30)..(30)
<223> OTHER INFORMATION: Xaa may be Thr or Ser
<220> FEATURE:
<221> NAME/KEY: misc_feature
<222> LOCATION: (49)..(49)
<223> OTHER INFORMATION: Xaa may be Ile or Met
<220> FEATURE:
<221> NAME/KEY: misc_feature
<222> LOCATION: (68)..(68)
<223> OTHER INFORMATION: Xaa may be Val or Ile
<220> FEATURE:
<221> NAME/KEY: misc_feature
<222> LOCATION: (70)..(70)
<223> OTHER INFORMATION: Xaa may be Met or Ile

<400> SEQUENCE: 14

Gln Val Gln Leu Gln Glu Ser Gly Pro Gly Leu Val Lys Pro Ser Asp

-continued

```
1               5                   10                  15
Thr Leu Ser Leu Thr Cys Ala Val Ser Gly Tyr Ser Ile Xaa Gly Gly
            20                  25                  30

Tyr Ser Trp His Trp Ile Arg Gln Pro Pro Gly Lys Gly Leu Glu Trp
        35                  40                  45

Xaa Gly Tyr Ile His Tyr Ser Gly Tyr Thr Asp Phe Asn Pro Ser Leu
    50                  55                  60

Lys Thr Arg Xaa Thr Xaa Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Gly Phe Pro Tyr Trp Gly Gln Gly Thr
                100                 105                 110

Leu Val Thr Val Ser Ser
            115
```

<210> SEQ ID NO 15
<211> LENGTH: 118
<212> TYPE: PRT
<213> ORGANISM: Artificial Sequence
<220> FEATURE:
<223> OTHER INFORMATION: 15C1 Hu VH version 3-66
<220> FEATURE:
<221> NAME/KEY: misc_feature
<222> LOCATION: (24)..(24)
<223> OTHER INFORMATION: Xaa may be Ala or Val
<220> FEATURE:
<221> NAME/KEY: misc_feature
<222> LOCATION: (49)..(49)
<223> OTHER INFORMATION: Xaa may be Val or Met
<220> FEATURE:
<221> NAME/KEY: misc_feature
<222> LOCATION: (79)..(79)
<223> OTHER INFORMATION: Xaa may be Leu or Phe

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Xaa Ser Gly Tyr Ser Ile Thr Gly Gly
            20                  25                  30

Tyr Ser Trp His Trp Val Arg Gln Ala Pro Gly Lys Gly Leu Glu Trp
        35                  40                  45

Xaa Ser Tyr Ile His Tyr Ser Gly Tyr Thr Asp Phe Asn Pro Ser Leu
    50                  55                  60

Lys Thr Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Arg Lys Asp Pro Ser Asp Gly Phe Pro Tyr Trp Gly Gln Gly Thr
                100                 105                 110

Leu Val Thr Val Ser Ser
            115
```

<210> SEQ ID NO 16
<211> LENGTH: 107
<212> TYPE: PRT
<213> ORGANISM: Artificial Sequence
<220> FEATURE:
<223> OTHER INFORMATION: 15C1 Hu VL version L6
<220> FEATURE:
<221> NAME/KEY: misc_feature
<222> LOCATION: (49)..(49)

<223> OTHER INFORMATION: Xaa may be Lys or Tyr

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys
            100                 105
```

<210> SEQ ID NO 17
<211> LENGTH: 9
<212> TYPE: PRT
<213> ORGANISM: Artificial Sequence
<220> FEATURE:
<223> OTHER INFORMATION: 15C1 Hu VL version L6 CDR3

<400> SEQUENCE: 17

```
Gln Asn Gly His Ser Phe Pro Leu Thr
1               5
```

<210> SEQ ID NO 18
<211> LENGTH: 107
<212> TYPE: PRT
<213> ORGANISM: Artificial Sequence
<220> FEATURE:
<223> OTHER INFORMATION: 15C1 Hu VL version A26

<400> SEQUENCE: 18

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Ser Phe Pro Leu
                85                  90                  95

Thr Phe Gly Gly Gly Thr Lys Val Glu Ile Lys
            100                 105
```

<210> SEQ ID NO 19
<211> LENGTH: 120
<212> TYPE: PRT
<213> ORGANISM: Artificial Sequence
<220> FEATURE:
<223> OTHER INFORMATION: 18H10 Hu VH version 1-69
<220> FEATURE:
<221> NAME/KEY: misc_feature
<222> LOCATION: (48)..(48)

<223> OTHER INFORMATION: Xaa may be Met or Ile
<220> FEATURE:
<221> NAME/KEY: misc_feature
<222> LOCATION: (74)..(74)
<223> OTHER INFORMATION: Xaa may be Lys or Thr
<220> FEATURE:
<221> NAME/KEY: misc_feature
<222> LOCATION: (81)..(81)
<223> OTHER INFORMATION: Xaa may be Met or Leu

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Ser
            20                  25                  30

Tyr Ile His Trp Val Arg Gln Ala Pro Gly Gln Gly Leu Glu Trp Xaa
        35                  40                  45

Gly Trp Thr Asp Pro Glu Asn Val Asn Ser Ile Tyr Asp Pro Arg Phe
    50                  55                  60

Gln Gly Arg Val Thr Ile Thr Ala Asp Xaa Ser Thr Ser Thr Ala Tyr
65                  70                  75                  80

Xaa Glu Leu Ser Ser Leu Arg Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120

<210> SEQ ID NO 20
<211> LENGTH: 5
<212> TYPE: PRT
<213> ORGANISM: Artificial Sequence
<220> FEATURE:
<223> OTHER INFORMATION: 18H10 Hu VH version 1-69 CDR1

<400> SEQUENCE: 20

Asp Ser Tyr Ile His
1               5

<210> SEQ ID NO 21
<211> LENGTH: 17
<212> TYPE: PRT
<213> ORGANISM: Artificial Sequence
<220> FEATURE:
<223> OTHER INFORMATION: 18H10 Hu VH version 1-69 CDR2

<400> SEQUENCE: 21

Trp Thr Asp Pro Glu Asn Val Asn Ser Ile Tyr Asp Pro Arg Phe Gln
1               5                   10                  15

Gly

<210> SEQ ID NO 22
<211> LENGTH: 11
<212> TYPE: PRT
<213> ORGANISM: Artificial Sequence
<220> FEATURE:
<223> OTHER INFORMATION: 18H10 Hu VH version 1-69 CDR3

<400> SEQUENCE: 22

Gly Tyr Asn Gly Val Tyr Tyr Ala Met Asp Tyr
1               5                   10

<210> SEQ ID NO 23

<211> LENGTH: 106
<212> TYPE: PRT
<213> ORGANISM: Artificial Sequence
<220> FEATURE:
<223> OTHER INFORMATION: 18H10 Hu VL version L6
<220> FEATURE:
<221> NAME/KEY: misc_feature
<222> LOCATION: (70)..(70)
<223> OTHER INFORMATION: Xaa may be Phe or Tyr

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ile Tyr Met
            20                  25                  30

His Trp Tyr Gln Gln Lys Pro Gly Gln Ala Pro Arg Leu Leu Ile Tyr
        35                  40                  45

Arg Thr Tyr Asn Leu Ala Ser Gly Ile Pro Ala Arg Phe Ser Gly Ser
    50                  55                  60

Gly Ser Gly Thr Asp Xaa Thr Leu Thr Ile Ser Ser Leu Glu Pro Glu
65                  70                  75                  80

Asp Phe Ala Val Tyr Tyr Cys His Gln Trp Ser Ser Phe Pro Tyr Thr
                85                  90                  95

Phe Gly Gln Gly Thr Lys Val Glu Ile Lys
            100                 105

<210> SEQ ID NO 24
<211> LENGTH: 10
<212> TYPE: PRT
<213> ORGANISM: Artificial Sequence
<220> FEATURE:
<223> OTHER INFORMATION: 18H10 Hu VL version L6 CDR1

<400> SEQUENCE: 24

Ser Ala Ser Ser Ser Val Ile Tyr Met His
1               5                   10

<210> SEQ ID NO 25
<211> LENGTH: 7
<212> TYPE: PRT
<213> ORGANISM: Artificial Sequence
<220> FEATURE:
<223> OTHER INFORMATION: 18H10 Hu VL version L6 CDR2

<400> SEQUENCE: 25

Arg Thr Tyr Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: 18H10 Hu VL version L6 CDR3

<400> SEQUENCE: 26

His Gln Trp Ser Ser Phe Pro Tyr Thr
1               5

<210> SEQ ID NO 27
<211> LENGTH: 121
<212> TYPE: PRT
<213> ORGANISM: Artificial Sequence
<220> FEATURE:
<223> OTHER INFORMATION: 7E3 Hu VH version 2-70

```
<220> FEATURE:
<221> NAME/KEY: misc_feature
<222> LOCATION: (30)..(30)
<223> OTHER INFORMATION: Xaa may be Ser or Thr
<220> FEATURE:
<221> NAME/KEY: misc_feature
<222> LOCATION: (71)..(71)
<223> OTHER INFORMATION: Xaa may be Ile or Phe
<220> FEATURE:
<221> NAME/KEY: misc_feature
<222> LOCATION: (98)..(98)
<223> OTHER INFORMATION: Xaa may be Ile or Ala

<400> SEQUENCE: 27

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
    50                  55                  60

Leu Lys Ser Arg Leu Thr Xaa Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120

<210> SEQ ID NO 28
<211> LENGTH: 7
<212> TYPE: PRT
<213> ORGANISM: Artificial Sequence
<220> FEATURE:
<223> OTHER INFORMATION: 7E3 Hu VH version 2-70 CDR1

<400> SEQUENCE: 28

Thr Tyr Asn Ile Gly Val Gly
1               5

<210> SEQ ID NO 29
<211> LENGTH: 16
<212> TYPE: PRT
<213> ORGANISM: Artificial Sequence
<220> FEATURE:
<223> OTHER INFORMATION: 7E3 Hu VH version 2-70 CDR2

<400> SEQUENCE: 29

His Ile Trp Trp Asn Asp Asn Ile Tyr Tyr Asn Thr Val Leu Lys Ser
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: 7E3 Hu VH version 2-70 CDR3

<400> SEQUENCE: 30

Met Ala Glu Gly Arg Tyr Asp Ala Met Asp Tyr
1               5                   10
```

```
<210> SEQ ID NO 31
<211> LENGTH: 121
<212> TYPE: PRT
<213> ORGANISM: Artificial Sequence
<220> FEATURE:
<223> OTHER INFORMATION: 7E3 Hu VH version 3-66
<220> FEATURE:
<221> NAME/KEY: misc_feature
<222> LOCATION: (24)..(24)
<223> OTHER INFORMATION: Xaa may be Phe or Ala
<220> FEATURE:
<221> NAME/KEY: misc_feature
<222> LOCATION: (50)..(50)
<223> OTHER INFORMATION: Xaa may be Val or Leu
<220> FEATURE:
<221> NAME/KEY: misc_feature
<222> LOCATION: (71)..(71)
<223> OTHER INFORMATION: Xaa may be Ile or Phe
<220> FEATURE:
<221> NAME/KEY: misc_feature
<222> LOCATION: (73)..(73)
<223> OTHER INFORMATION: Xaa may be Lys or Arg
<220> FEATURE:
<221> NAME/KEY: misc_feature
<222> LOCATION: (80)..(80)
<223> OTHER INFORMATION: Xaa may be Leu or Val
<220> FEATURE:
<221> NAME/KEY: misc_feature
<222> LOCATION: (98)..(98)
<223> OTHER INFORMATION: Xaa may be Ile or Ala

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Thr Thr Tyr
            20                  25                  30

Asn Ile Gly Val Gly Trp Val Arg Gln Ala Pro Gly Lys Gly Leu Glu
        35                  40                  45

Trp Xaa Ser His Ile Trp Trp Asn Asp Asn Ile Tyr Tyr Asn Thr Val
    50                  55                  60

Leu Lys Ser Arg Leu Thr Xaa Ser Xaa Asp Asn Ser Lys Asn Thr Xaa
65                  70                  75                  80

Tyr Leu Gln Met Asn Ser Leu Arg Ala Glu Asp Thr Ala Val Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: 7E3 Hu VL version L19
<220> FEATURE:
<221> NAME/KEY: misc_feature
<222> LOCATION: (71)..(71)
<223> OTHER INFORMATION: Xaa may be Phe or Tyr
<220> FEATURE:
<221> NAME/KEY: misc_feature
<222> LOCATION: (87)..(87)
<223> OTHER INFORMATION: Xaa may be Tyr or Phe

<400> SEQUENCE: 32

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Thr Asn Tyr
```

```
                 20                  25                  30

Leu Asn Trp Tyr Gln Gln Lys Pro Gly Lys Ala Pro Lys Leu Leu Ile
             35                  40                  45

Tyr Tyr Thr Ser Lys Leu His Ser Gly Val Pro Ser Arg Phe Ser Gly
         50                  55                  60

Ser Gly Ser Gly Thr Asp Xaa Thr Leu Thr Ile Ser Ser Leu Gln Pro
 65                  70                  75                  80

Glu Asp Phe Ala Thr Tyr Xaa Cys Gln Gln Gly Asn Thr Phe Pro Trp
                 85                  90                  95

Thr Phe Gly Gly Gly Thr Lys Val Glu Ile Lys
             100                 105

<210> SEQ ID NO 33
<211> LENGTH: 11
<212> TYPE: PRT
<213> ORGANISM: Artificial Sequence
<220> FEATURE:
<223> OTHER INFORMATION: 7E3 Hu VL version L19 CDR1

<400> SEQUENCE: 33

Arg Ala Ser Gln Asp Ile Thr Asn Tyr Leu Asn
 1               5                  10

<210> SEQ ID NO 34
<211> LENGTH: 7
<212> TYPE: PRT
<213> ORGANISM: Artificial Sequence
<220> FEATURE:
<223> OTHER INFORMATION: 7E3 Hu VL version L19 CDR2

<400> SEQUENCE: 34

Tyr Thr Ser Lys Leu His Ser
 1               5

<210> SEQ ID NO 35
<211> LENGTH: 9
<212> TYPE: PRT
<213> ORGANISM: Artificial Sequence
<220> FEATURE:
<223> OTHER INFORMATION: 7E3 Hu VL version L19 CDR3

<400> SEQUENCE: 35

Gln Gln Gly Asn Thr Phe Pro Trp Thr
 1               5

<210> SEQ ID NO 36
<211> LENGTH: 118
<212> TYPE: PRT
<213> ORGANISM: Artificial Sequence
<220> FEATURE:
<223> OTHER INFORMATION: 15C1 humanized VH mutant 1

<400> SEQUENCE: 36

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Thr Gly Gly
             20                  25                  30

Tyr Ser Trp His Trp Ile Arg Gln Pro Pro Gly Lys Gly Leu Glu Trp
         35                  40                  45

Met Gly Tyr Ile His Tyr Ser Gly Tyr Thr Asp Phe Asn Pro Ser Leu
     50                  55                  60

Lys Thr Arg Ile Thr Ile Ser Arg Asp Thr Ser Lys Asn Gln Phe Ser
```

```
                65                  70                  75                  80
Leu Lys Leu Ser Ser Val Thr Ala Val Asp Thr Ala Val Tyr Tyr Cys
                    85                  90                  95

Ala Arg Lys Asp Pro Ser Asp Ala Phe Pro Tyr Trp Gly Gln Gly Thr
                100                 105                 110

Leu Val Thr Val Ser Ser
        115
```

<210> SEQ ID NO 37
<211> LENGTH: 354
<212> TYPE: DNA
<213> ORGANISM: Artificial Sequence
<220> FEATURE:
<223> OTHER INFORMATION: 15C1 humanized VH mutant 1

<400> SEQUENCE: 37

```
caggtgcagc ttcaggagtc cggcccagga ctggtgaagc cttcggacac cctgtccctc    60
acctgcgctg tctctggtta ctccatcacc ggtggttata ctggcactg gatacggcag    120 cccccaggga agggactgga gtggatgggg tatatccact acagtggtta cactgacttc    180 aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
ccgtccgacg cctttcctta ctggggccaa gggactctgg tcactgtctc ttcc         354
```

<210> SEQ ID NO 38
<211> LENGTH: 118
<212> TYPE: PRT
<213> ORGANISM: Artificial Sequence
<220> FEATURE:
<223> OTHER INFORMATION: 15C1 humanized VH mutant 2

<400> SEQUENCE: 38

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
                20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
        50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                    85                  90                  95

Ala Arg Lys Asp Pro Ser Glu Gly Phe Pro Tyr Trp Gly Gln Gly Thr
                100                 105                 110

Leu Val Thr Val Ser Ser
        115
```

<210> SEQ ID NO 39
<211> LENGTH: 354
<212> TYPE: DNA
<213> ORGANISM: Artificial Sequence
<220> FEATURE:
<223> OTHER INFORMATION: 15C1 humanized VH mutant 2

<400> SEQUENCE: 39

```
caggtgcagc ttcaggagtc cggcccagga ctggtgaagc cttcggacac cctgtccctc    60
```

```
acctgcgctg tctctggtta ctccatcacc ggtggttata gctggcactg gatacggcag    120
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgagg gatttcctta ctggggccaa gggactctgg tcactgtctc ttcc          354
```

```
<210> SEQ ID NO 40
<211> LENGTH: 107
<212> TYPE: PRT
<213> ORGANISM: Artificial Sequence
<220> FEATURE:
<223> OTHER INFORMATION: 15C1 humanized VL mutant 1

<400> SEQUENCE: 40
```

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser His Ser Phe Pro Leu
                85                  90                  95

Thr Phe Gly Gly Gly Thr Lys Val Glu Ile Lys
            100                 105
```

```
<210> SEQ ID NO 41
<211> LENGTH: 321
<212> TYPE: DNA
<213> ORGANISM: Artificial Sequence
<220> FEATURE:
<223> OTHER INFORMATION: 15C1 humanized VL mutant 1

<400> SEQUENCE: 41
gaaattgtgt tgacgcagtc tccagacttt cagtctgtga ctccaaagga aaaagtcacc    60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagaat agtcacagtt ttccgctcac tttcggcgga    300
gggaccaagg tggagatcaa a                                              321
```

```
<210> SEQ ID NO 42
<211> LENGTH: 107
<212> TYPE: PRT
<213> ORGANISM: Artificial Sequence
<220> FEATURE:
<223> OTHER INFORMATION: 15C1 humanized VL mutant 2

<400> SEQUENCE: 42
```

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30
```

```
Leu His Trp Tyr Gln Gln Lys Pro Asp Gln Ser Pro Lys Leu Leu Ile
         35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly His Ser Phe Pro Leu
                 85                  90                  95

Thr Phe Gly Gly Gly Thr Lys Val Glu Ile Lys
            100                 105
```

<210> SEQ ID NO 43
<211> LENGTH: 321
<212> TYPE: DNA
<213> ORGANISM: Artificial Sequence
<220> FEATURE:
<223> OTHER INFORMATION: 15C1 humanized VL mutant 2

<400> SEQUENCE: 43

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                                321
```

<210> SEQ ID NO 44
<211> LENGTH: 107
<212> TYPE: PRT
<213> ORGANISM: Artificial Sequence
<220> FEATURE:
<223> OTHER INFORMATION: 15C1 humanized VL mutant 3

<400> SEQUENCE: 44

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
                 20                  25                  30

Leu His Trp Tyr Gln Gln Lys Pro Asp Gln Ser Pro Lys Leu Leu Ile
         35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Asn Ser Ser Ser Phe Pro Leu
                 85                  90                  95

Thr Phe Gly Gly Gly Thr Lys Val Glu Ile Lys
            100                 105
```

<210> SEQ ID NO 45
<211> LENGTH: 321
<212> TYPE: DNA
<213> ORGANISM: Artificial Sequence
<220> FEATURE:
<223> OTHER INFORMATION: 15C1 humanized VL mutant 3

<400> SEQUENCE: 45

```
gaaattgtgt tgacgcagtc tccagacttt cagtctgtga ctccaaagga aaaagtcacc      60
```

```
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagaat agtagtagtt ttccgctcac tttcggcgga    300
gggaccaagg tggagatcaa a                                              321
```

<210> SEQ ID NO 46
<211> LENGTH: 107
<212> TYPE: PRT
<213> ORGANISM: Artificial Sequence
<220> FEATURE:
<223> OTHER INFORMATION: 15C1 humanized VL mutant 4

<400> SEQUENCE: 46

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Phe Pro Leu
                85                  90                  95

Thr Phe Gly Gly Gly Thr Lys Val Glu Ile Lys
            100                 105
```

<210> SEQ ID NO 47
<211> LENGTH: 321
<212> TYPE: DNA
<213> ORGANISM: Artificial Sequence
<220> FEATURE:
<223> OTHER INFORMATION: 15C1 humanized VL mutant 4

<400> SEQUENCE: 47

```
gaaattgtgt tgacgcagtc tccagacttt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag agtcacagtt ttccgctcac tttcggcgga    300
gggaccaagg tggagatcaa a                                              321
```

<210> SEQ ID NO 48
<211> LENGTH: 9
<212> TYPE: PRT
<213> ORGANISM: Artificial Sequence
<220> FEATURE:
<223> OTHER INFORMATION: anti-TLR4 variable heavy chain complementarity
    determining region 1
<220> FEATURE:
<221> NAME/KEY: misc_feature
<222> LOCATION: (2)..(2)
<223> OTHER INFORMATION: Xaa may be Phe or Tyr
<220> FEATURE:
<221> NAME/KEY: misc_feature
<222> LOCATION: (5)..(5)

```
<223> OTHER INFORMATION: Xaa may be Arg, Gly or Trp
<220> FEATURE:
<221> NAME/KEY: misc_feature
<222> LOCATION: (6)..(6)
<223> OTHER INFORMATION: Xaa may be Tyr, Phe or Gly

<400> SEQUENCE: 48

Gly Xaa Pro Ile Xaa Xaa Gly Tyr Ser
1               5

<210> SEQ ID NO 49
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 49

Gly Tyr Ser Ile Thr Gly Gly Tyr Ser
1               5

<210> SEQ ID NO 50
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 50

Gly Phe Pro Ile Arg Tyr Gly Tyr Ser
1               5

<210> SEQ ID NO 51
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 51

Gly Tyr Pro Ile Arg Phe Gly Tyr

<210> SEQ ID NO 54
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 54

Gly Tyr Pro Ile Trp Gly Gly Tyr Ser
1               5

<210> SEQ ID NO 55
<211> LENGTH: 9
<212> TYPE: PRT
<213> ORGANISM: Artificial Sequence
<220> FEATURE:
<223> OTHER INFORMATION: anti-TLR4 variable heavy chain complementarity
      determining region 1

<400> SEQUENCE: 55

Gly Tyr Pro Ile Gly Gly Gly Tyr Ser
1               5

<210> SEQ ID NO 56
<211> LENGTH: 7
<212> TYPE: PRT
<213> ORGANISM: Artificial Sequence
<220> FEATURE:
<223> OTHER INFORMATION: anti-TLR4 variable heavy chain complementarity
      determining region 2

<400> SEQUENCE: 56

Ile His Tyr Ser Gly Tyr Thr
1               5

<210> SEQ ID NO 57
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3
<220> FEATURE:
<221> NAME/KEY: misc_feature
<222> LOCATION: (7)..(7)
<223> OTHER INFORMATION: Xaa may be Asn, Gln, Asp or Glu
<220> FEATURE:
<221> NAME/KEY: misc_feature
<222> LOCATION: (8)..(9)
<223> OTHER INFORMATION: Xaa may be any hydrophobic amino acid

<400> SEQUENCE: 57

Ala Arg Lys Asp Ser Gly Xaa Xaa Xaa Pro Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 58

Ala Arg Lys Asp Ser Gly Asn Tyr Phe Pro Tyr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 59

Ala Arg Lys Asp Ser Gly Arg Leu Leu Pro Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 60

Ala Arg Lys Asp Ser Gly Lys Trp Leu Pro Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 61

Ala Arg Lys Asp Ser Gly His Leu Met Pro Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 62

Ala Arg Lys Asp Ser Gly His Asn Tyr Pro Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 63

Ala Arg Lys Asp Ser Gly Lys Asn Phe Pro Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

```
<400> SEQUENCE: 64

Ala Arg Lys Asp Ser Gly Gln Leu Phe Pro Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 65

Ala Arg Lys Asp Ser Gly His Asn Leu Pro Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 66

Ala Arg Lys Asp Ser Gly Asp Tyr Phe Pro Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: anti-TLR4 variable heavy chain complementarity
      determining region 3

<400> SEQUENCE: 67

Ala Arg Lys Asp Ser Gly Arg Tyr Trp Pro Tyr
1               5                   10

<210> SEQ ID NO 68
<211> LENGTH: 6
<212> TYPE: PRT
<213> ORGANISM: Artificial Sequence
<220> FEATURE:
<223> OTHER INFORMATION: anti-TLR4 variable light chain complementarity
      determining region 1

<400> SEQUENCE: 68

Gln Ser Ile Ser Asp His
1               5

<210> SEQ ID NO 69
<211> LENGTH: 3
<212> TYPE: PRT
<213> ORGANISM: Artificial Sequence
<220> FEATURE:
<223> OTHER INFORMATION: anti-TLR4 variable light chain complementarity
      determining region 2

<400> SEQUENCE: 69

Tyr Ala Ser
1

<210> SEQ ID NO 70
<211> LENGTH: 9
```

```
-continued

<212> TYPE: PRT
<213> ORGANISM: Artificial Sequence
<220> FEATURE:
<223> OTHER INFORMATION: anti-TLR4 variable light chain complementarity
      determining region 3
<220> FEATURE:
<221> NAME/KEY: misc_feature
<222> LOCATION: (4)..(4)
<223> OTHER INFORMATION: Xaa may be Tyr or Asn
<220> FEATURE:
<221> NAME/KEY: misc_feature
<222> LOCATION: (5)..(5)
<223> OTHER INFORMATION: Xaa may be Asp or Glu
<220> FEATURE:
<221> NAME/KEY: misc_feature
<222> LOCATION: (6)..(6)
<223> OTHER INFORMATION: Xaa may be Phe or Tyr
<220> FEATURE:
<221> NAME/KEY: misc_feature
<222> LOCATION: (8)..(8)
<223> OTHER INFORMATION: Xaa may be any hydrophobic amino acid

<400> SEQUENCE: 70

Gln Gln Gly Xaa Xaa Xaa Pro Xaa Thr
1               5

<210> SEQ ID NO 71
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 71

Gln Gln Gly Asn Asp Phe Pro Val Thr
1               5

<210> SEQ ID NO 72
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 72

Gln Gln Gly Tyr Asp Glu Pro Phe Thr
1               5

<210> SEQ ID NO 73
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 73

Gln Gln Gly Tyr Asp Phe Pro Leu Thr
1               5

<210> SEQ ID NO 74
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 74
```

Gln Gln Gly Tyr Asp Tyr Pro Leu Thr
1               5

<210> SEQ ID NO 75
<211> LENGTH: 9
<212> TYPE: PRT
<213> ORGANISM: Artificial Sequence
<220> FEATURE:
<223> OTHER INFORMATION: anti-TLR4 variable light chain complementarity
      determining region 3

<400> SEQUENCE: 75

Gln Gln Gly Tyr Glu Phe Pro Leu Thr
1               5

<210> SEQ ID NO 76
<211> LENGTH: 4
<212> TYPE: PRT
<213> ORGANISM: Artificial Sequence
<220> FEATURE:
<223> OTHER INFORMATION: altered human IgG1 gamma heavy chain constant
      region

<400> SEQUENCE: 76

Ser Lys Ala Phe
1

<210> SEQ ID NO 77
<211> LENGTH: 826
<212> TYPE: PRT
<213> ORGANISM: Cynomolgus sp.

<400> SEQUENCE: 77

Met Thr Ser Ala Leu Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Lys Phe Tyr Lys Ile
        35                  40                  45

Pro Asp Asn Ile Pro Phe Ser Thr Lys Asn Leu Asp Leu Ser Phe Asn
    50                  55                  60

Pro Leu Arg His Leu Gly Ser Tyr Ser Phe Arg Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Asn Ile Tyr Cys
            180                 185                 190

Lys Asp Leu Gln Val Leu His Gln Met Pro Leu Ser Asn Leu Ser Leu
        195                 200                 205

```
Asp Leu Ser Leu Asn Pro Ile Asn Phe Ile Gln Pro Gly Ala Phe Lys
    210                 215                 220

Glu Ile Arg Leu His Lys Leu Thr Leu Arg Ser Asn Phe Asp Asp Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Arg Asn Leu Glu Glu Phe
            260                 265                 270

Asp Lys Ser Ser Leu Glu Gly Leu Cys Asn Leu Thr Ile Glu Glu Phe
        275                 280                 285

Arg Leu Thr Tyr Leu Asp Cys Tyr Leu Asp Asn Ile Ile Asp Leu Phe
290                 295                 300

Asn Cys Leu Ala Asn Val Ser Ser Phe Ser Leu Val Ser Val Asn Ile
305                 310                 315                 320

Lys Arg Val Glu Asp Phe Ser Tyr Asn Phe Arg Trp Gln His Leu Glu
                325                 330                 335

Leu Val Asn Cys Lys Phe Glu Gln Phe Pro Thr Leu Glu Leu Lys Ser
            340                 345                 350

Leu Lys Arg Leu Thr Phe Thr Ala Asn Lys Gly Gly Asn Ala Phe Ser
        355                 360                 365

Glu Val Asp Leu Pro Ser Leu Glu Phe Leu Asp Leu Ser Arg Asn Gly
370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Asp Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Gln Phe Ser Val Phe Leu Ser Leu Arg Asn
        435                 440                 445

Leu Ile Tyr Leu Asp Ile Ser His Thr His Thr Arg Val Ala Phe Asn
450                 455                 460

Gly Ile Phe Asp Gly Leu Leu Ser Leu Lys Val Leu Lys Met Ala Gly
465                 470                 475                 480

Asn Ser Phe Gln Glu Asn Phe Leu Pro Asp Ile Phe Thr Asp Leu Lys
                485                 490                 495

Asn Leu Thr Phe Leu Asp Leu Ser Gln Cys Gln Leu Glu Gln Leu Ser
            500                 505                 510

Pro Thr Ala Phe Asp Thr Leu Asn Lys Leu Gln Val Leu Asn Met Ser
        515                 520                 525

His Asn Asn Phe Phe Ser Leu Asp Thr Phe Pro Tyr Lys Cys Leu Pro
530                 535                 540

Ser Leu Gln Val Leu Asp Tyr Ser Leu Asn His Ile Met Thr Ser Asn
545                 550                 555                 560

Asn Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Ala Glu Arg Met Glu
        595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Phe Ser
```

```
                625                 630                 635                 640
Val Leu Val Val Ser Val Val Ala Val Leu Val Tyr Lys Phe Tyr Phe
                        645                 650                 655

His Leu Met Leu Leu Ala Gly Cys Ile Lys Tyr Gly Arg Gly Glu Asn
                660                 665                 670

Ile Tyr Asp Ala Phe Val Ile Tyr Ser Ser Gln Asp Glu Asp Trp Val
                    675                 680                 685

Arg Asn Glu Leu Val Lys Asn Leu Glu Glu Gly Val Pro Pro Phe Gln
            690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                    725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
                755                 760                 765

Ile Val Leu Gln Lys Val Glu Lys Thr Leu Leu Arg Gln Gln Val Glu
                770                 775                 780

Leu Tyr Arg Leu Leu Ser Arg Asn Thr Tyr Leu Glu Trp Glu Asp Ser
785                 790                 795                 800

Val Leu Gly Gln His Ile Phe Trp Arg Arg Leu Arg Lys Ala Leu Leu
                    805                 810                 815

Asp Gly Lys Ser Trp Asn Pro Glu Glu Gln
                820                 825

<210> SEQ ID NO 78
<211> LENGTH: 354
<212> TYPE: DNA
<213> ORGANISM: Artificial Sequence
<220> FEATURE:
<223> OTHER INFORMATION: 1E11 anti-TLR4 variable heavy chain

<400> SEQUENCE: 78
caggtgcagc ttcaggagtc cggcccagga ctggtgaagc cttcggacac cctgtccctc      60
acctgcgctg tctctggtta ctccatcacc ggtggttata ctggcactg gatacggcag     120 cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc           354

<210> SEQ ID NO 79
<211> LENGTH: 118
<212> TYPE: PRT
<213> ORGANISM: Artificial Sequence
<220> FEATURE:
<223> OTHER INFORMATION: 1E11 anti-TLR4 variable heavy chain

<400> SEQUENCE: 79

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45
```

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 80
<211> LENGTH: 321
<212> TYPE: DNA
<213> ORGANISM: Artificial Sequence
<220> FEATURE:
<223> OTHER INFORMATION: 1E11 anti-TLR4 variable light chain

<400> SEQUENCE: 80
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321

<210> SEQ ID NO 81
<211> LENGTH: 107
<212> TYPE: PRT
<213> ORGANISM: Artificial Sequence
<220> FEATURE:
<223> OTHER INFORMATION: 1E11 anti-TLR4 variable light chain

<400> SEQUENCE: 81

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 82
<211> LENGTH: 354
<212> TYPE: DNA
<213> ORGANISM: Artificial Sequence
<220> FEATURE:
<223> OTHER INFORMATION: 1A1 anti-TLR4 variable heavy chain

<400> SEQUENCE: 82
caggtgcagc ttcaggagtc cggcccagga ctggtgaagc cttcggacac cctgtccctc    60

```
acctgcgctg tctctggtta ctccatcacc ggtggttata gctggcactg gatacggcag    120
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
tccggccgcc cctcccctta ctggggccaa gggactctgg tcactgtctc ttcc          354
```

<210> SEQ ID NO 83
<211> LENGTH: 118
<212> TYPE: PRT
<213> ORGANISM: Artificial Sequence
<220> FEATURE:
<223> OTHER INFORMATION: 1A1 anti-TLR4 variable heavy chain

<400> SEQUENCE: 83

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Arg Leu Leu Pro Tyr Trp Gly Gln Gly Thr
            100                 105                 110

Leu Val Thr Val Ser Ser
        115
```

<210> SEQ ID NO 84
<211> LENGTH: 321
<212> TYPE: DNA
<213> ORGANISM: Artificial Sequence
<220> FEATURE:
<223> OTHER INFORMATION: 1A1 anti-TLR4 variable light chain

<400> SEQUENCE: 84

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321
```

<210> SEQ ID NO 85
<211> LENGTH: 107
<212> TYPE: PRT
<213> ORGANISM: Artificial Sequence
<220> FEATURE:
<223> OTHER INFORMATION: 1A1 anti-TLR4 variable light chain

<400> SEQUENCE: 85

```
Glu Ile Val Leu Thr Gln Ser Pro Asp Phe Gln Ser Val Thr Pro Lys
1               5                   10                  15
```

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 86
<211> LENGTH: 354
<212> TYPE: DNA
<213> ORGANISM: Artificial Sequence
<220> FEATURE:
<223> OTHER INFORMATION: 1A6 anti-TLR4 variable heavy chain

<400> SEQUENCE: 86
caggtgcagc ttcaggagtc cggcccagga ctggtgaagc cttcggacac cctgtccctc    60
acctgcgctg tctctggtta ctccatcacc ggtggttata ctggcactg gatacggcag   120 cccccaggga agggactgga gtggatgggg tatatccact acagtggtta cactgacttc   180 aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
agcggcaagt ggttgcctta ctggggccaa gggactctgg tcactgtctc ttcc         354

<210> SEQ ID NO 87
<211> LENGTH: 118
<212> TYPE: PRT
<213> ORGANISM: Artificial Sequence
<220> FEATURE:
<223> OTHER INFORMATION: 1A6 anti-TLR4 variable heavy chain

<400> SEQUENCE: 87

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Lys Trp Leu Pro Tyr Trp Gly Gln Gly Thr
            100                 105                 110

Leu Val Thr Val Ser Ser
        115

<210> SEQ ID NO 88
<211> LENGTH: 321
<212> TYPE: DNA

<213> ORGANISM: Artificial Sequence
<220> FEATURE:
<223> OTHER INFORMATION: 1A6 anti-TLR4 variable light chain

<400> SEQUENCE: 88

| | |
|---|---|
| gaaattgtgt tgacgcagtc tccagacttt cagtctgtga ctccaaagga aaaagtcacc | 60 |
| atcacctgca gggccagtca gagtatcagc gaccacttac actggtacca acagaaacct | 120 |
| gatcagtctc ccaagctcct catcaaatat gcttcccatg ccatttctgg ggtcccatcg | 180 |
| aggttcagtg gcagtgggtc tgggacagac ttcactctca ccatcaatag cctagaggct | 240 |
| gaagatgctg caacgtatta ctgtcagcag ggtcacagtt ttccgctcac tttcggcgga | 300 |
| gggaccaagg tggagatcaa a | 321 |

<210> SEQ ID NO 89
<211> LENGTH: 107
<212> TYPE: PRT
<213> ORGANISM: Artificial Sequence
<220> FEATURE:
<223> OTHER INFORMATION: 1A6 anti-TLR4 variable light chain

<400> SEQUENCE: 89

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 90
<211> LENGTH: 354
<212> TYPE: DNA
<213> ORGANISM: Artificial Sequence
<220> FEATURE:
<223> OTHER INFORMATION: 1B12 anti-TLR4 variable heavy chain

<400> SEQUENCE: 90

| | |
|---|---|
| caggtgcagc ttcaggagtc cggcccagga ctggtgaagc cttcggacac cctgtccctc | 60 |
| acctgcgctg tctctggtta ctccatcacc ggtggttata ctggcactg gatacggcag | 120 |
| cccccaggga agggactgga gtggatgggg tatatccact acagtggtta cactgacttc | 180 |
| aaccctccc tcaagactcg aatcaccata tcacgtgaca cgtccaagaa ccagttctcc | 240 |
| ctgaagctga gctctgtgac cgctgtggac actgcagtgt attactgtgc gagaaaagat | 300 |
| agcgggcacc tcatgcctta ctggggccaa gggactctgg tcactgtctc ttcc | 354 |

<210> SEQ ID NO 91
<211> LENGTH: 118
<212> TYPE: PRT
<213> ORGANISM: Artificial Sequence
<220> FEATURE:
<223> OTHER INFORMATION: 1B12 anti-TLR4 variable heavy chain

<400> SEQUENCE: 91

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Leu Met Pro Tyr Trp Gly Gln Gly Thr
            100                 105                 110

Leu Val Thr Val Ser Ser
            115

<210> SEQ ID NO 92
<211> LENGTH: 321
<212> TYPE: DNA
<213> ORGANISM: Artificial Sequence
<220> FEATURE:
<223> OTHER INFORMATION: 1B12 anti-TLR4 variable light chain

<400> SEQUENCE: 92
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321

<210> SEQ ID NO 93
<211> LENGTH: 107
<212> TYPE: PRT
<213> ORGANISM: Artificial Sequence
<220> FEATURE:
<223> OTHER INFORMATION: 1B12 anti-TLR4 variable light chain

<400> SEQUENCE: 93

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 94
<211> LENGTH: 354
<212> TYPE: DNA
<213> ORGANISM: Artificial Sequence
<220> FEATURE:
<223> OTHER INFORMATION: 1C7 anti-TLR4 variable heavy chain

<400> SEQUENCE: 94

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tccgggcaca actacccctta ctggggccaa gggactctgg tcactgtctc ttcc          354
```

<210> SEQ ID NO 95
<211> LENGTH: 118
<212> TYPE: PRT
<213> ORGANISM: Artificial Sequence
<220> FEATURE:
<223> OTHER INFORMATION: 1C7 anti-TLR4 variable heavy chain

<400> SEQUENCE: 95

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Asn Tyr Pro Tyr Trp Gly Gln Gly Thr
            100                 105                 110

Leu Val Thr Val Ser Ser
        115
```

<210> SEQ ID NO 96
<211> LENGTH: 321
<212> TYPE: DNA
<213> ORGANISM: Artificial Sequence
<220> FEATURE:
<223> OTHER INFORMATION: 1C7 anti-TLR4 variable light chain

<400> SEQUENCE: 96

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                                321
```

```
<210> SEQ ID NO 97
<211> LENGTH: 107
<212> TYPE: PRT
<213> ORGANISM: Artificial Sequence
<220> FEATURE:
<223> OTHER INFORMATION: 1C7 anti-TLR4 variable light chain

<400> SEQUENCE: 97

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln His Ser Phe Pro Leu
                85                  90                  95

Thr Phe Gly Gly Gly Thr Lys Val Glu Ile Lys
            100                 105

<210> SEQ ID NO 98
<211> LENGTH: 354
<212> TYPE: DNA
<213> ORGANISM: Artificial Sequence
<220> FEATURE:
<223> OTHER INFORMATION: 1C10 anti-TLR4 variable heavy chain

<400> SEQUENCE: 98
caggtgcagc ttcaggagtc cggcccagga ctggtgaagc cttcggacac cctgtccctc     60
acctgcgctg tctctggtta ctccatcacc ggtggttata gctggcactg gatacggcag    120
cccccaggga agggactgga gtggatgggg tatatccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggcaaga acttccctta ctggggccaa gggactctgg tcactgtctc ttcc          354

<210> SEQ ID NO 99
<211> LENGTH: 118
<212> TYPE: PRT
<213> ORGANISM: Artificial Sequence
<220> FEATURE:
<223> OTHER INFORMATION: 1C10 anti-TLR4 variable heavy chain

<400> SEQUENCE: 99

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95
```

Ala Arg Lys Asp Ser Gly Lys Asn Phe Pro Tyr Trp Gly Gln Gly Thr
            100                 105                 110

Leu Val Thr Val Ser Ser
        115

<210> SEQ ID NO 100
<211> LENGTH: 321
<212> TYPE: DNA
<213> ORGANISM: Artificial Sequence
<220> FEATURE:
<223> OTHER INFORMATION: 1C10 anti-TLR4 variable light chain

<400> SEQUENCE: 100
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321

<210> SEQ ID NO 101
<211> LENGTH: 107
<212> TYPE: PRT
<213> ORGANISM: Artificial Sequence
<220> FEATURE:
<223> OTHER INFORMATION: 1C10 anti-TLR4 variable light chain

<400> SEQUENCE: 101

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 102
<211> LENGTH: 354
<212> TYPE: DNA
<213> ORGANISM: Artificial Sequence
<220> FEATURE:
<223> OTHER INFORMATION: 1C12 anti-TLR4 variable heavy chain

<400> SEQUENCE: 102
caggtgcagc ttcaggagtc cggcccagga ctggtgaagc cttcggacac cctgtccctc    60
acctgcgctg tctctggtta ctccatcacc ggtggttata ctggcactg gatacggcag   120 cccccaggga agggactgga gtggatgggg tatatccact acagtggtta cactgacttc   180 aaccccctccc tcaagactcg aatcaccata tcacgtgaca cgtccaagaa ccagttctcc   240
ctgaagctga gctctgtgac cgctgtggac actgcagtgt attactgtgc gagaaaagat   300

```
agcggccagt tgttccctta ctggggccaa gggactctgg tcactgtctc ttcc      354
```

<210> SEQ ID NO 103
<211> LENGTH: 118
<212> TYPE: PRT
<213> ORGANISM: Artificial Sequence
<220> FEATURE:
<223> OTHER INFORMATION: 1C12 anti-TLR4 variable heavy chain

<400> SEQUENCE: 103

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Gln Leu Phe Pro Tyr Trp Gly Gln Gly Thr
            100                 105                 110

Leu Val Thr Val Ser Ser
        115
```

<210> SEQ ID NO 104
<211> LENGTH: 321
<212> TYPE: DNA
<213> ORGANISM: Artificial Sequence
<220> FEATURE:
<223> OTHER INFORMATION: 1C12 anti-TLR4 variable light chain

<400> SEQUENCE: 104

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                               321
```

<210> SEQ ID NO 105
<211> LENGTH: 107
<212> TYPE: PRT
<213> ORGANISM: Artificial Sequence
<220> FEATURE:
<223> OTHER INFORMATION: 1C12 anti-TLR4 variable light chain

<400> SEQUENCE: 105

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
```

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 106
<211> LENGTH: 354
<212> TYPE: DNA
<213> ORGANISM: Artificial Sequence
<220> FEATURE:
<223> OTHER INFORMATION: 1D10 anti-TLR4 variable heavy chain

<400> SEQUENCE: 106
caggtgcagc ttcaggagtc cggcccagga ctggtgaagc cttcggacac cctgtccctc    60
acctgcgctg tctctggtta ctccatcacc ggtggttata ctggcactg gatacggcag   120 cccccaggga agggactgga gtggatgggg tatatccact acagtggtta cactgacttc   180
aaccctctcc tcaagactcg aatcaccata tcacgtgaca cgtccaagaa ccagttctcc   240
ctgaagctga gctctgtgac cgctgtggac actgcagtgt attactgtgc gagaaaagat   300
agcggccaca acttgcctta ctggggccaa gggactctgg tcactgtctc ttcc        354

<210> SEQ ID NO 107
<211> LENGTH: 118
<212> TYPE: PRT
<213> ORGANISM: Artificial Sequence
<220> FEATURE:
<223> OTHER INFORMATION: 1D10 anti-TLR4 variable heavy chain

<400> SEQUENCE: 107

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
                20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
        50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Asn Leu Pro Tyr Trp Gly Gln Gly Thr
            100                 105                 110

Leu Val Thr Val Ser Ser
        115

<210> SEQ ID NO 108
<211> LENGTH: 321
<212> TYPE: DNA
<213> ORGANISM: Artificial Sequence
<220> FEATURE:
<223> OTHER INFORMATION: 1D10 anti-TLR4 variable light chain

<400> SEQUENCE: 108
gaaattgtgt tgacgcagtc tccagacttt cagtctgtga ctccaaagga aaaagtcacc    60

```
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggtcacagtt ttccgctcac tttcggcgga    300
gggaccaagg tggagatcaa a                                              321
```

<210> SEQ ID NO 109
<211> LENGTH: 107
<212> TYPE: PRT
<213> ORGANISM: Artificial Sequence
<220> FEATURE:
<223> OTHER INFORMATION: 1D10 anti-TLR4 variable light chain

<400> SEQUENCE: 109

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105
```

<210> SEQ ID NO 110
<211> LENGTH: 354
<212> TYPE: DNA
<213> ORGANISM: Artificial Sequence
<220> FEATURE:
<223> OTHER INFORMATION: 1E11 N103D anti-TLR4 variable heavy chain

<400> SEQUENCE: 110

```
caggtgcagc ttcaggagtc cggcccagga ctggtgaagc cttcggacac cctgtccctc     60
acctgcgctg tctctggtta ctccatcacc ggtggttata ctggcactg gatacggcag    120 cccccaggga agggactgga gtggatgggg tatatccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcgact acttcccta ctggggccaa gggactctgg tcactgtctc ttcc           354
```

<210> SEQ ID NO 111
<211> LENGTH: 118
<212> TYPE: PRT
<213> ORGANISM: Artificial Sequence
<220> FEATURE:
<223> OTHER INFORMATION: 1E11 N103D anti-TLR4 variable heavy chain

<400> SEQUENCE: 111

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30
```

```
Tyr Ser Trp His Trp Ile Arg Gln Pro Pro Gly Lys Gly Leu Glu Trp
        35                  40                  45
Met Gly Tyr Ile His Tyr Ser Gly Tyr Thr Asp Phe Asn Pro Ser Leu
 50                  55                  60
Lys Thr Arg Ile Thr Ile Ser Arg Asp Thr Ser Lys Asn Gln Phe Ser
 65                  70                  75                  80
Leu Lys Leu Ser Ser Val Thr Ala Val Asp Thr Ala Val Tyr Tyr Cys
                 85                  90                  95
Ala Arg Lys Asp Ser Gly Asp Tyr Phe Pro Tyr Trp Gly Gln Gly Thr
            100                 105                 110
Leu Val Thr Val Ser Ser
            115

<210> SEQ ID NO 112
<211> LENGTH: 321
<212> TYPE: DNA
<213> ORGANISM: Artificial Sequence
<220> FEATURE:
<223> OTHER INFORMATION: 1E11 N103D anti-TLR4 variable light chain

<400> SEQUENCE: 112
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccattctggg gtcccatcg    180 aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321

<210> SEQ ID NO 113
<211> LENGTH: 107
<212> TYPE: PRT
<213> ORGANISM: Artificial Sequence
<220> FEATURE:
<223> OTHER INFORMATION: 1E11 N103D anti-TLR4 variable light chain

<400> SEQUENCE: 113

Glu Ile Val Leu Thr Gln Ser Pro Asp Phe Gln Ser Val Thr Pro Lys
 1               5                  10                  15
Glu Lys Val Thr Ile Thr Cys Arg Ala Ser Gln Ser Ile Ser Asp His
                 20                  25                  30
Leu His Trp Tyr Gln Gln Lys Pro Asp Gln Ser Pro Lys Leu Leu Ile
            35                  40                  45
Lys Tyr Ala Ser His Ala Ile Ser Gly Val Pro Ser Arg Phe Ser Gly
 50                  55                  60
Ser Gly Ser Gly Thr Asp Phe Thr Leu Thr Ile Asn Ser Leu Glu Ala
 65                  70                  75                  80
Glu Asp Ala Ala Thr Tyr Tyr Cys Gln Gln Gly His Ser Phe Pro Leu
                 85                  90                  95
Thr Phe Gly Gly Gly Thr Lys Val Glu Ile Lys
            100                 105

<210> SEQ ID NO 114
<211> LENGTH: 354
<212> TYPE: DNA
<213> ORGANISM: Artificial Sequence
<220> FEATURE:
<223> OTHER INFORMATION: 1G12 anti-TLR4 variable heavy chain
```

<400> SEQUENCE: 114

```
caggtgcagc ttcaggagtc cggcccagga ctggtgaagc cttcggacac cctgtccctc    60
acctgcgctg tctctggtta ctccatcacc ggtggttata ctggcactg gatacggcag   120
cccccaggga agggactgga gtggatgggg tatatccact acagtggtta cactgacttc   180
aaccccteee tcaagactcg aatcaccata tcacgtgaca cgtccaagaa ccagttctcc   240
ctgaagctga gctctgtgac cgctgtggac actgcagtgt attactgtgc gagaaaagat   300
tccgggcggt actggcctta ctggggccaa gggactctgg tcactgtctc ttcc         354
```

<210> SEQ ID NO 115
<211> LENGTH: 118
<212> TYPE: PRT
<213> ORGANISM: Artificial Sequence
<220> FEATURE:
<223> OTHER INFORMATION: 1G12 anti-TLR4 variable heavy chain

<400> SEQUENCE: 115

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Arg Tyr Trp Pro Tyr Trp Gly Gln Gly Thr
            100                 105                 110

Leu Val Thr Val Ser Ser
        115
```

<210> SEQ ID NO 116
<211> LENGTH: 321
<212> TYPE: DNA
<213> ORGANISM: Artificial Sequence
<220> FEATURE:
<223> OTHER INFORMATION: 1G12 anti-TLR4 variable light chain

<400> SEQUENCE: 116

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt tccgctcac tttcggcgga   300
gggaccaagg tggagatcaa a                                            321
```

<210> SEQ ID NO 117
<211> LENGTH: 107
<212> TYPE: PRT
<213> ORGANISM: Artificial Sequence
<220> FEATURE:
<223> OTHER INFORMATION: 1G12 anti-TLR4 variable light chain

<400> SEQUENCE: 117

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
                35                  40                  45

Lys Tyr Ala Ser His Ala Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
                100                 105

<210> SEQ ID NO 118
<211> LENGTH: 354
<212> TYPE: DNA
<213> ORGANISM: Artificial Sequence
<220> FEATURE:
<223> OTHER INFORMATION: 1E11.C1 anti-TLR4 variable heavy chain

<400> SEQUENCE: 118
caggtgcagc ttcaggagtc cggcccagga ctggtgaagc cttcggacac cctgtccctc      60
acctgcgctg tctctggttt cccgatccgc tacgggtata gctggcactg gatcggcag     120 cccccaggga agggactgga gtggatgggg tatatcccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccttta ctggggccaa gggactctgg tcactgtctc ttcc          354

<210> SEQ ID NO 119
<211> LENGTH: 118
<212> TYPE: PRT
<213> ORGANISM: Artificial Sequence
<220> FEATURE:
<223> OTHER INFORMATION: 1E11.C1 anti-TLR4 variable heavy chain

<400> SEQUENCE: 119

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
                35                  40                  45

Met Gly Tyr Ile His Tyr Ser Gly Tyr Thr Asp Phe Asn Pro Ser Leu
        50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
                100                 105                 110

Leu Val Thr Val Ser Ser
            115

<210> SEQ ID NO 120
<211> LENGTH: 321
<212> TYPE: DNA
<213> ORGANISM: Artificial Sequence
<220> FEATURE:
<223> OTHER INFORMATION: 1E11.C1 anti-TLR4 variable light chain

<400> SEQUENCE: 120

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                               321
```

<210> SEQ ID NO 121
<211> LENGTH: 107
<212> TYPE: PRT
<213> ORGANISM: Artificial Sequence
<220> FEATURE:
<223> OTHER INFORMATION: 1E11.C1 anti-TLR4 variable light chain

<400> SEQUENCE: 121

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105
```

<210> SEQ ID NO 122
<211> LENGTH: 354
<212> TYPE: DNA
<213> ORGANISM: Artificial Sequence
<220> FEATURE:
<223> OTHER INFORMATION: 1E11.C2 anti-TLR4 variable heavy chain

<400> SEQUENCE: 122

```
caggtgcagc ttcaggagtc cggcccagga ctggtgaagc cttcggacac cctgtccctc      60
acctgcgctg tctctggtta cccgatccgg ttcggctata ctggcactg gatacggcag     120 cccccaggga agggactgga gtggatgggg tatatccact acagtggtta cactgacttc     180
aaccctctcc ctcaagactc gaatcaccat atcacgtgaca cgtccaagaa ccagttctcc     240
ctgaagctga gctctgtgac cgctgtggac actgcagtgt attactgtgc gagaaaagat     300
tcgggcaact acttccctta ctggggccaa gggactctgg tcactgtctc ttcc           354
```

<210> SEQ ID NO 123
<211> LENGTH: 118
<212> TYPE: PRT
<213> ORGANISM: Artificial Sequence
<220> FEATURE:
<223> OTHER INFORMATION: 1E11.C2 anti-TLR4 variable heavy chain

<400> SEQUENCE: 123

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 124
<211> LENGTH: 321
<212> TYPE: DNA
<213> ORGANISM: Artificial Sequence
<220> FEATURE:
<223> OTHER INFORMATION: 1E11.C2 anti-TLR4 variable light chain

<400> SEQUENCE: 124

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                             321
```

<210> SEQ ID NO 125
<211> LENGTH: 107
<212> TYPE: PRT
<213> ORGANISM: Artificial Sequence
<220> FEATURE:
<223> OTHER INFORMATION: 1E11.C2 anti-TLR4 variable light chain

<400> SEQUENCE: 125

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
              100                 105

<210> SEQ ID NO 126
<211> LENGTH: 354
<212> TYPE: DNA
<213> ORGANISM: Artificial Sequence
<220> FEATURE:
<223> OTHER INFORMATION: 1E11.C3 anti-TLR4 variable heavy chain

<400> SEQUENCE: 126
caggtgcagc ttcaggagtc cggcccagga ctggtgaagc cttcggacac cctgtccctc    60
acctgcgctg tctctggtta ccccatccgg cacgggtaca gctggcactg gatacggcag   120
cccccaggga agggactgga gtggatgggg tatatccact acagtggtta cactgacttc   180
aaccctctcc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccta ctggggccaa gggactctgg tcactgtctc ttcc           354

<210> SEQ ID NO 127
<211> LENGTH: 118
<212> TYPE: PRT
<213> ORGANISM: Artificial Sequence
<220> FEATURE:
<223> OTHER INFORMATION: 1E11.C3 anti-TLR4 variable heavy chain

<400> SEQUENCE: 127

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg His Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 128
<211> LENGTH: 321
<212> TYPE: DNA
<213> ORGANISM: Artificial Sequence
<220> FEATURE:
<223> OTHER INFORMATION: 1E11.C3 anti-TLR4 variable light chain

<400> SEQUENCE: 128
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300

```
gggaccaagg tggagatcaa a                                              321
```

<210> SEQ ID NO 129
<211> LENGTH: 107
<212> TYPE: PRT
<213> ORGANISM: Artificial Sequence
<220> FEATURE:
<223> OTHER INFORMATION: 1E11.C3 anti-TLR4 variable light chain

<400> SEQUENCE: 129

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105
```

<210> SEQ ID NO 130
<211> LENGTH: 354
<212> TYPE: DNA
<213> ORGANISM: Artificial Sequence
<220> FEATURE:
<223> OTHER INFORMATION: 1E11.C4 anti-TLR4 variable heavy chain

<400> SEQUENCE: 130

```
caggtgcagc ttcaggagtc cggcccagga ctggtgaagc cttcggacac cctgtccctc    60
acctgcgctg tctctggttt cccgatcggc caggggtata gctggcactg gatacggcag   120
cccccaggga agggactgga gtggatgggg tatatccact acagtggtta cactgacttc   180 aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttccctta ctggggccaa gggactctgg tcactgtctc ttcc          354
```

<210> SEQ ID NO 131
<211> LENGTH: 118
<212> TYPE: PRT
<213> ORGANISM: Artificial Sequence
<220> FEATURE:
<223> OTHER INFORMATION: 1E11.C4 anti-TLR4 variable heavy chain

<400> SEQUENCE: 131

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Gly Gln Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80
```

```
Leu Lys Leu Ser Ser Val Thr Ala Val Asp Thr Ala Val Tyr Tyr Cys
            85                  90                  95

Ala Arg Lys Asp Ser Gly Asn Tyr Phe Pro Tyr Trp Gly Gln Gly Thr
        100                 105                 110

Leu Val Thr Val Ser Ser
        115

<210> SEQ ID NO 132
<211> LENGTH: 321
<212> TYPE: DNA
<213> ORGANISM: Artificial Sequence
<220> FEATURE:
<223> OTHER INFORMATION: 1E11.C4 anti-TLR4 variable light chain

<400> SEQUENCE: 132
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt tccgctcac tttcggcgga      300 gggaccaagg tggagatcaa a                                               321

<210> SEQ ID NO 133
<211> LENGTH: 107
<212> TYPE: PRT
<213> ORGANISM: Artificial Sequence
<220> FEATURE:
<223> OTHER INFORMATION: 1E11.C4 anti-TLR4 variable light chain

<400> SEQUENCE: 133

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 134
<211> LENGTH: 363
<212> TYPE: DNA
<213> ORGANISM: Artificial Sequence
<220> FEATURE:
<223> OTHER INFORMATION: 1E11.C5 anti-TLR4 variable heavy chain

<400> SEQUENCE: 134
caggtgcagc ttcaggagtc cggcccagga ctggtgaagc cttcggacac cctgtccctc      60
acctgcgctg tctctggtta cccgatctgg ggggctata gctggcactg gatacggcag      120
cccccaggga agggactgga gtggatgggg tatatccact acagtggtta cactgacttc     180
```

```
aaccccuccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccttg ctggggccaa gggactctgg tcactgtctc ttccgcctcc    360
acc                                                                 363
```

<210> SEQ ID NO 135
<211> LENGTH: 118
<212> TYPE: PRT
<213> ORGANISM: Artificial Sequence
<220> FEATURE:
<223> OTHER INFORMATION: 1E11.C5 anti-TLR4 variable heavy chain

<400> SEQUENCE: 135

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Trp Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115
```

<210> SEQ ID NO 136
<211> LENGTH: 321
<212> TYPE: DNA
<213> ORGANISM: Artificial Sequence
<220> FEATURE:
<223> OTHER INFORMATION: 1E11.C5 anti-TLR4 variable light chain

<400> SEQUENCE: 136

```
gaaattgtgt tgacgcagtc tccagacttt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggtcacagtt ttccgctcac tttcggcgga    300
gggaccaagg tggagatcaa a                                               321
```

<210> SEQ ID NO 137
<211> LENGTH: 107
<212> TYPE: PRT
<213> ORGANISM: Artificial Sequence
<220> FEATURE:
<223> OTHER INFORMATION: 1E11.C5 anti-TLR4 variable light chain

<400> SEQUENCE: 137

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30
```

Leu His Trp Tyr Gln Gln Lys Pro Asp Gln Ser Pro Lys Leu Leu Ile
            35                  40                  45

Lys Tyr Ala Ser His Ala Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 138
<211> LENGTH: 354
<212> TYPE: DNA
<213> ORGANISM: Artificial Sequence
<220> FEATURE:
<223> OTHER INFORMATION: 1E11.C6 anti-TLR4 variable heavy chain

<400> SEQUENCE: 138
caggtgcagc ttcaggagtc cggcccagga ctggtgaagc cttcggacac cctgtccctc      60
acctgcgctg tctctggtta ccccatcggc ggcggctata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccta ctggggccaa gggactctgg tcactgtctc ttcc            354

<210> SEQ ID NO 139
<211> LENGTH: 118
<212> TYPE: PRT
<213> ORGANISM: Artificial Sequence
<220> FEATURE:
<223> OTHER INFORMATION: 1E11.C6 anti-TLR4 variable heavy chain

<400> SEQUENCE: 139

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Gly Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 140
<211> LENGTH: 321
<212> TYPE: DNA
<213> ORGANISM: Artificial Sequence
<220> FEATURE:
<223> OTHER INFORMATION: 1E11.C6 anti-TLR4 variable light chain -continued

<400> SEQUENCE: 140

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggtcacagtt ttccgctcac tttcggcgga     300
gggaccaagg tggagatcaa a                                                321
```

<210> SEQ ID NO 141
<211> LENGTH: 107
<212> TYPE: PRT
<213> ORGANISM: Artificial Sequence
<220> FEATURE:
<223> OTHER INFORMATION: 1E11.C6 anti-TLR4 variable light chain

<400> SEQUENCE: 141

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105
```

<210> SEQ ID NO 142
<211> LENGTH: 354
<212> TYPE: DNA
<213> ORGANISM: Artificial Sequence
<220> FEATURE:
<223> OTHER INFORMATION: 1E11.E1 anti-TLR4 variable heavy chain

<400> SEQUENCE: 142

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttcccta  ctggggccaa gggactctgg tcactgtctc ttcc            354
```

<210> SEQ ID NO 143
<211> LENGTH: 118
<212> TYPE: PRT
<213> ORGANISM: Artificial Sequence
<220> FEATURE:
<223> OTHER INFORMATION: 1E11.E1 anti-TLR4 variable heavy chain

<400> SEQUENCE: 143

```
Gln Val Gln Leu Gln Glu Ser Gly Pro Gly Leu Val Lys Pro Ser Asp
```

```
            1               5                  10                 15
         Thr Leu Ser Leu Thr Cys Ala Val Ser Gly Tyr Ser Ile Thr Gly Gly
                         20                  25                  30

Tyr Ser Trp His Trp Ile Arg Gln Pro Pro Gly Lys Gly Leu Glu Trp
                     35                  40                  45

Met Gly Tyr Ile His Tyr Ser Gly Tyr Thr Asp Phe Asn Pro Ser Leu
                 50                  55                  60

Lys Thr Arg Ile Thr Ile Ser Arg Asp Thr Ser Lys Asn Gln Phe Ser
         65                  70                  75                  80

Leu Lys Leu Ser Ser Val Thr Ala Val Asp Thr Ala Val Tyr Tyr Cys
                             85                  90                  95

Ala Arg Lys Asp Ser Gly Asn Tyr Phe Pro Tyr Trp Gly Gln Gly Thr
                         100                 105                 110

Leu Val Thr Val Ser Ser
                         115

<210> SEQ ID NO 144
<211> LENGTH: 321
<212> TYPE: DNA
<213> ORGANISM: Artificial Sequence
<220> FEATURE:
<223> OTHER INFORMATION: 1E11.E1 anti-TLR4 variable light chain

<400> SEQUENCE: 144
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggaacgact tcccggtgac tttcggcgga     300
gggaccaagg tggagatcaa a                                                321

<210> SEQ ID NO 145
<211> LENGTH: 107
<212> TYPE: PRT
<213> ORGANISM: Artificial Sequence
<220> FEATURE:
<223> OTHER INFORMATION: 1E11.E1 anti-TLR4 variable light chain

<400> SEQUENCE: 145

Glu Ile Val Leu Thr Gln Ser Pro Asp Phe Gln Ser Val Thr Pro Lys
         1               5                   10                  15

Glu Lys Val Thr Ile Thr Cys Arg Ala Ser Gln Ser Ile Ser Asp His
                         20                  25                  30

Leu His Trp Tyr Gln Gln Lys Pro Asp Gln Ser Pro Lys Leu Leu Ile
                     35                  40                  45

Lys Tyr Ala Ser His Ala Ile Ser Gly Val Pro Ser Arg Phe Ser Gly
                 50                  55                  60

Ser Gly Ser Gly Thr Asp Phe Thr Leu Thr Ile Asn Ser Leu Glu Ala
         65                  70                  75                  80

Glu Asp Ala Ala Thr Tyr Tyr Cys Gln Gln Gly Asn Asp Phe Pro Val
                             85                  90                  95

Thr Phe Gly Gly Gly Thr Lys Val Glu Ile Lys
                         100                 105

<210> SEQ ID NO 146
<211> LENGTH: 354
```

<212> TYPE: DNA
<213> ORGANISM: Artificial Sequence
<220> FEATURE:
<223> OTHER INFORMATION: 1E11.E2 anti-TLR4 variable heavy chain

<400> SEQUENCE: 146

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccttca ctggggccaa gggactctgg tcactgtctc ttcc          354
```

<210> SEQ ID NO 147
<211> LENGTH: 118
<212> TYPE: PRT
<213> ORGANISM: Artificial Sequence
<220> FEATURE:
<223> OTHER INFORMATION: 1E11.E2 anti-TLR4 variable heavy chain

<400> SEQUENCE: 147

Gln Val Gln Leu Gln Glu Ser Gly Pro Gly Leu Val Lys Pro Ser Asp
1               5                   10                  15
Thr Leu Ser Leu Thr Cys Ala Val Ser Gly Tyr Ser Ile Thr Gly Gly
            20                  25                  30
Tyr Ser Trp His Trp Ile Arg Gln Pro Pro Gly Lys Gly Leu Glu Trp
        35                  40                  45
Met Gly Tyr Ile His Tyr Ser Gly Tyr Thr Asp Phe Asn Pro Ser Leu
    50                  55                  60
Lys Thr Arg Ile Thr Ile Ser Arg Asp Thr Ser Lys Asn Gln Phe Ser
65                  70                  75                  80
Leu Lys Leu Ser Ser Val Thr Ala Val Asp Thr Ala Val Tyr Tyr Cys
                85                  90                  95
Ala Arg Lys Asp Ser Gly Asn Tyr Phe Pro Tyr Trp Gly Gln Gly Thr
            100                 105                 110
Leu Val Thr Val Ser Ser
        115

<210> SEQ ID NO 148
<211> LENGTH: 321
<212> TYPE: DNA
<213> ORGANISM: Artificial Sequence
<220> FEATURE:
<223> OTHER INFORMATION: 1E11.E2 anti-TLR4 variable light chain

<400> SEQUENCE: 148

```
gaaattgtgt tgacgcagtc tccagacttt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag gggtacgacg agccgttcac tttcggcgga    300
gggaccaagg tggagatcaa a                                              321
```

<210> SEQ ID NO 149
<211> LENGTH: 107
<212> TYPE: PRT

<213> ORGANISM: Artificial Sequence
<220> FEATURE:
<223> OTHER INFORMATION: 1E11.E2 anti-TLR4 variable light chain

<400> SEQUENCE: 149

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Glu Pro Phe
                85                  90                  95

Thr Phe Gly Gly Gly Thr Lys Val Glu Ile Lys
            100                 105
```

<210> SEQ ID NO 150
<211> LENGTH: 354
<212> TYPE: DNA
<213> ORGANISM: Artificial Sequence
<220> FEATURE:
<223> OTHER INFORMATION: 1E11.E3 anti-TLR4 variable heavy chain

<400> SEQUENCE: 150

```
caggtgcagc ttcaggagtc cggcccagga ctggtgaagc cttcggacac cctgtccctc      60
acctgcgctg tctctggtta ctccatcacc ggtggttata ctggcactg gatacggcag     120
cccccaggga agggactgga gtggatgggg tatatccact acagtggtta cactgacttc     180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccta ctggggccaa gggactctgg tcactgtctc ttcc            354
```

<210> SEQ ID NO 151
<211> LENGTH: 118
<212> TYPE: PRT
<213> ORGANISM: Artificial Sequence
<220> FEATURE:
<223> OTHER INFORMATION: 1E11.E3 anti-TLR4 variable heavy chain

<400> SEQUENCE: 151

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110
```

Leu Val Thr Val Ser Ser
        115

<210> SEQ ID NO 152
<211> LENGTH: 321
<212> TYPE: DNA
<213> ORGANISM: Artificial Sequence
<220> FEATURE:
<223> OTHER INFORMATION: 1E11.E3 anti-TLR4 variable light chain

<400> SEQUENCE: 152

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact cccgttgac tttcggcgga      300 gggaccaagg tggagatcaa a                                                321
```

<210> SEQ ID NO 153
<211> LENGTH: 107
<212> TYPE: PRT
<213> ORGANISM: Artificial Sequence
<220> FEATURE:
<223> OTHER INFORMATION: 1E11.E3 anti-TLR4 variable light chain

<400> SEQUENCE: 153

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Phe Pro Leu
                85                  90                  95

Thr Phe Gly Gly Gly Thr Lys Val Glu Ile Lys
            100                 105

<210> SEQ ID NO 154
<211> LENGTH: 354
<212> TYPE: DNA
<213> ORGANISM: Artificial Sequence
<220> FEATURE:
<223> OTHER INFORMATION: 1E11.E4 anti-TLR4 variable heavy chain

<400> SEQUENCE: 154

```
caggtgcagc ttcaggagtc cggcccagga ctggtgaagc cttcggacac cctgtccctc      60
acctgcgctg tctctggtta ctccatcacc ggtggttata ctggcactg gatacggcag     120 cccccaggga agggactgga gtggatgggg tatatcccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttccctta ctggggccaa gggactctgg tcactgtctc ttcc           354
```

<210> SEQ ID NO 155
<211> LENGTH: 118
<212> TYPE: PRT
<213> ORGANISM: Artificial Sequence
<220> FEATURE:
<223> OTHER INFORMATION: 1E11.E4 anti-TLR4 variable heavy chain

<400> SEQUENCE: 155

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 156
<211> LENGTH: 321
<212> TYPE: DNA
<213> ORGANISM: Artificial Sequence
<220> FEATURE:
<223> OTHER INFORMATION: 1E11.E4 anti-TLR4 variable light chain

<400> SEQUENCE: 156
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact accgctcac tttcggcgga      300 gggaccaagg tggagatcaa a                                               321

<210> SEQ ID NO 157
<211> LENGTH: 107
<212> TYPE: PRT
<213> ORGANISM: Artificial Sequence
<220> FEATURE:
<223> OTHER INFORMATION: 1E11.E4 anti-TLR4 variable light chain

<400> SEQUENCE: 157

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala

```
                65                  70                  75                  80
Glu Asp Ala Ala Thr Tyr Tyr Cys Gln Gln Gly Tyr Asp Tyr Pro Leu
                        85                  90                  95

Thr Phe Gly Gly Gly Thr Lys Val Glu Ile Lys
                100                 105

<210> SEQ ID NO 158
<211> LENGTH: 354
<212> TYPE: DNA
<213> ORGANISM: Artificial Sequence
<220> FEATURE:
<223> OTHER INFORMATION: 1E11.E5 anti-TLR4 variable heavy chain

<400> SEQUENCE: 158
caggtgcagc ttcaggagtc cggcccagga ctggtgaagc cttcggacac cctgtccctc     60
acctgcgctg tctctggtta ctccatcacc ggtggttata ctggcactg gatacggcag    120 cccccaggga agggactgga gtggatgggg tatatccact acagtggtta cactgacttc    180
aaccccctcc caagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccta ctggggccaa gggactctgg tcactgtctc ttcc          354

<210> SEQ ID NO 159
<211> LENGTH: 118
<212> TYPE: PRT
<213> ORGANISM: Artificial Sequence
<220> FEATURE:
<223> OTHER INFORMATION: 1E11.E5 anti-TLR4 variable heavy chain

<400> SEQUENCE: 159

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 160
<211> LENGTH: 321
<212> TYPE: DNA
<213> ORGANISM: Artificial Sequence
<220> FEATURE:
<223> OTHER INFORMATION: 1E11.E5 anti-TLR4 variable light chain

<400> SEQUENCE: 160
gaaattgtgt tgacgcagtc tccagactt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
```

```
aggttcagtg gcagtgggtc tgggacagac ttcactctca ccatcaatag cctagaggct    240
gaagatgctg caacgtatta ctgtcagcag ggctacgagt tcccgttgac tttcggcgga    300
gggaccaagg tggagatcaa a                                              321
```

<210> SEQ ID NO 161
<211> LENGTH: 107
<212> TYPE: PRT
<213> ORGANISM: Artificial Sequence
<220> FEATURE:
<223> OTHER INFORMATION: 1E11.E5 anti-TLR4 variable light chain

<400> SEQUENCE: 161

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Glu Phe Pro Leu
                85                  90                  95

Thr Phe Gly Gly Gly Thr Lys Val Glu Ile Lys
            100                 105
```

<210> SEQ ID NO 162
<211> LENGTH: 354
<212> TYPE: DNA
<213> ORGANISM: Artificial Sequence
<220> FEATURE:
<223> OTHER INFORMATION: 1E11.C2E1 anti-TLR4 variable heavy chain

<400> SEQUENCE: 162

```
caggtgcagc ttcaggagtc cggcccagga ctggtgaagc cttcggacac cctgtccctc     60
acctgcgctg tctctggtta cccgatccgg ttcggctata ctggcactg gatacggcag    120 cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttcccttta ctggggccaa gggactctgg tcactgtctc ttcc         354
```

<210> SEQ ID NO 163
<211> LENGTH: 118
<212> TYPE: PRT
<213> ORGANISM: Artificial Sequence
<220> FEATURE:
<223> OTHER INFORMATION: 1E11.C2E1 anti-TLR4 variable heavy chain

<400> SEQUENCE: 163

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45
```

```
Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
            115

<210> SEQ ID NO 164
<211> LENGTH: 321
<212> TYPE: DNA
<213> ORGANISM: Artificial Sequence
<220> FEATURE:
<223> OTHER INFORMATION: 1E11.C2E1 anti-TLR4 variable light chain

<400> SEQUENCE: 164
gaaattgtgt tgacgcagtc tccagacttt cagtctgtga ctccaaagga aaagtcacc      60 atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag gggaacgact cccggtgac tttcggcgga    300 gggaccaagg tggagatcaa a                                              321

<210> SEQ ID NO 165
<211> LENGTH: 107
<212> TYPE: PRT
<213> ORGANISM: Artificial Sequence
<220> FEATURE:
<223> OTHER INFORMATION: 1E11.C2E1 anti-TLR4 variable light chain

<400> SEQUENCE: 165

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Asn Asp Phe Pro Val
                85                  90                  95

Thr Phe Gly Gly Gly Thr Lys Val Glu Ile Lys
            100                 105

<210> SEQ ID NO 166
<211> LENGTH: 354
<212> TYPE: DNA
<213> ORGANISM: Artificial Sequence
<220> FEATURE:
<223> OTHER INFORMATION: 1E11.C2E3 anti-TLR4 variable heavy chain

<400> SEQUENCE: 166
caggtgcagc ttcaggagtc cggcccagga ctggtgaagc cttcggacac cctgtccctc      60
```

```
acctgcgctg tctctggtta cccgatccgg ttcggctata gctggcactg gatacggcag    120 ccccccaggga agggactgga gtggatgggga tatatcccact acagtggtta cactgacttc    180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc          354
```

<210> SEQ ID NO 167
<211> LENGTH: 118
<212> TYPE: PRT
<213> ORGANISM: Artificial Sequence
<220> FEATURE:
<223> OTHER INFORMATION: 1E11.C2E3 anti-TLR4 variable heavy chain

<400> SEQUENCE: 167

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115
```

<210> SEQ ID NO 168
<211> LENGTH: 321
<212> TYPE: DNA
<213> ORGANISM: Artificial Sequence
<220> FEATURE:
<223> OTHER INFORMATION: 1E11.C2E3 anti-TLR4 variable light chain

<400> SEQUENCE: 168

```
gaaattgtgt tgacgcagtc tccagacttt cagtctgtga ctccaaagga aaaagtcacc    60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggctacgact cccgttgac tttcggcgga    300 gggaccaagg tggagatcaa a                                              321
```

<210> SEQ ID NO 169
<211> LENGTH: 107
<212> TYPE: PRT
<213> ORGANISM: Artificial Sequence
<220> FEATURE:
<223> OTHER INFORMATION: 1E11.C2E3 anti-TLR4 variable light chain

<400> SEQUENCE: 169

```
Glu Ile Val Leu Thr Gln Ser Pro Asp Phe Gln Ser Val Thr Pro Lys
1               5                   10                  15
```

```
Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly Tyr Asp Phe Pro Leu
                85                  90                  95

Thr Phe Gly Gly Gly Thr Lys Val Glu Ile Lys
            100                 105
```

<210> SEQ ID NO 170
<211> LENGTH: 354
<212> TYPE: DNA
<213> ORGANISM: Artificial Sequence
<220> FEATURE:
<223> OTHER INFORMATION: 1E11.C2E4 anti-TLR4 variable heavy chain

<400> SEQUENCE: 170

```
caggtgcagc ttcaggagtc cggcccagga ctggtgaagc cttcggacac cctgtccctc    60
acctgcgctg tctctggtta cccgatccgg ttcggctata gctggcactg gatacgcag   120
cccccaggga agggactgga gtggatgggg tatatccact acagtggtta cactgacttc   180
aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccttac tggggccaa gggactctgg tcactgtctc ttcc        354
```

<210> SEQ ID NO 171
<211> LENGTH: 118
<212> TYPE: PRT
<213> ORGANISM: Artificial Sequence
<220> FEATURE:
<223> OTHER INFORMATION: 1E11.C2E4 anti-TLR4 variable heavy chain

<400> SEQUENCE: 171

```
Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
 50                  55                  60

Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
                100                 105                 110

Leu Val Thr Val Ser Ser
            115
```

<210> SEQ ID NO 172
<211> LENGTH: 321
<212> TYPE: DNA

<213> ORGANISM: Artificial Sequence
<220> FEATURE:
<223> OTHER INFORMATION: 1E11.C2E4 anti-TLR4 variable light chain

<400> SEQUENCE: 172

```
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggctacgact accgctcac tttcggcgga   300
gggaccaagg tggagatcaa a                                             321
```

<210> SEQ ID NO 173
<211> LENGTH: 107
<212> TYPE: PRT
<213> ORGANISM: Artificial Sequence
<220> FEATURE:
<223> OTHER INFORMATION: 1E11.C2E4 anti-TLR4 variable light chain

<400> SEQUENCE: 173

Glu Ile Val Leu Thr Gln Ser Pro Asp Phe Gln Ser Val Thr Pro Lys
1               5                   10                  15
Glu Lys Val Thr Ile Thr Cys Arg Ala Ser Gln Ser Ile Ser Asp His
            20                  25                  30
Leu His Trp Tyr Gln Gln Lys Pro Asp Gln Ser Pro Lys Leu Leu Ile
        35                  40                  45
Lys Tyr Ala Ser His Ala Ile Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys Gln Gln Gly Tyr Asp Tyr Pro Leu
                85                  90                  95
Thr Phe Gly Gly Gly Thr Lys Val Glu Ile Lys
            100                 105

<210> SEQ ID NO 174
<211> LENGTH: 354
<212> TYPE: DNA
<213> ORGANISM: Artificial Sequence
<220> FEATURE:
<223> OTHER INFORMATION: 1E11.C2E5 anti-TLR4 variable heavy chain

<400> SEQUENCE: 174

```
caggtgcagc ttcaggagtc cggcccagga ctggtgaagc cttcggacac cctgtccctc    60
acctgcgctg tctctggtta cccgatccgg ttcggctata ctggcactg gatacggcag   120
cccccaggga agggactgga gtggatgggg tatatccact acagtggtta cactgacttc   180
aaccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttccctta ctggggccaa gggactctgg tcactgtctc ttcc          354
```

<210> SEQ ID NO 175
<211> LENGTH: 118
<212> TYPE: PRT
<213> ORGANISM: Artificial Sequence
<220> FEATURE:
<223> OTHER INFORMATION: 1E11.C2E5 anti-TLR4 variable heavy chain

<400> SEQUENCE: 175

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
            115

<210> SEQ ID NO 176
<211> LENGTH: 321
<212> TYPE: DNA
<213> ORGANISM: Artificial Sequence
<220> FEATURE:
<223> OTHER INFORMATION: 1E11.C2E5 anti-TLR4 variable light chain

<400> SEQUENCE: 176
gaaattgtgt tgacgcagtc tccagacttt cagtctgtga ctccaaagga aaaagtcacc      60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggctacgagt tcccgttgac tttcggcgga    300
gggaccaagg tggagatcaa a                                              321

<210> SEQ ID NO 177
<211> LENGTH: 107
<212> TYPE: PRT
<213> ORGANISM: Artificial Sequence
<220> FEATURE:
<223> OTHER INFORMATION: 1E11.C2E5 anti-TLR4 variable light chain

<400> SEQUENCE: 177

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Glu Phe Pro Leu
                85                  90                  95

Thr Phe Gly Gly Gly Thr Lys Val Glu Ile Lys
            100                 105

<210> SEQ ID NO 178
<211> LENGTH: 447
<212> TYPE: PRT
<213> ORGANISM: Artificial Sequence
<220> FEATURE:
<223> OTHER INFORMATION: 1E11 IgG1 formatted anti-TLR4 heavy chain

<400> SEQUENCE: 178

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 179
<211> LENGTH: 214
<212> TYPE: PRT
<213> ORGANISM: Artificial Sequence
<220> FEATURE:
<223> OTHER INFORMATION: 1E11 IgG1 formatted anti-TLR4 light chain

<400> SEQUENCE: 179

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 180
<211> LENGTH: 705
<212> TYPE: DNA
<213> ORGANISM: Artificial Sequence
<220> FEATURE:
<223> OTHER INFORMATION: 1E11 IgG1 formatted anti-TLR4 light chain

<400> SEQUENCE: 180
atgagtgtgc ccactcaggt cctggggttg ctgctgctgt ggcttacaga tgccagatgt    60
```

```
gaaattgtgt tgacgcagtc tccagacttt cagtctgtga ctccaaagga aaaagtcacc        120
atcacctgca gggccagtca gagtatcagc gaccacttac actggtacca acagaaacct        180
gatcagtctc ccaagctcct catcaaatat gcttcccatg ccatttctgg ggtcccatcg        240
aggttcagtg gcagtgggtc tgggacagac ttcactctca ccatcaatag cctagaggct        300
gaagatgctg caacgtatta ctgtcagcag ggtcacagtt ttccgctcac tttcggcgga        360
gggaccaagg tggagatcaa acgtacggtg gctgcaccat ctgtcttcat cttcccgcca        420
tctgatgagc agttgaaatc tggaactgcc tctgttgtgt gcctgctgaa taacttctat        480
cccagagagg ccaaagtaca gtggaaggtg gataacgccc tccaatcggg taactcccag        540
gagagtgtca cagagcagga cagcaaggac agcacctaca gcctcagcag caccctgacg        600
ctgagcaaag cagactacga gaaacacaaa gtctacgcct gcgaagtcac ccatcagggc        660
ctgagctcgc ccgtcacaaa gagcttcaac aggggagagt gttaa                        705

<210> SEQ ID NO 181
<211> LENGTH: 1398
<212> TYPE: DNA
<213> ORGANISM: Artificial Sequence
<220> FEATURE:
<223> OTHER INFORMATION: 1E11 IgG1 formatted anti-TLR4 heavy chain

<400> SEQUENCE: 181
atggaatgga gctgggtctt tctcttcttc ctgtcagtaa ctacaggtgt ccaccaggtg         60
cagcttcagg agtccggccc aggactggtg aagccttcgg acaccctgtc cctcacctgc        120
gctgtctctg gttactccat caccggtggt tatagctggc actggatacg gcagccccca        180
gggaagggac tggagtggat ggggtatatc cactacagtg gttacactga cttcaacccc        240
tccctcaaga ctcgaatcac catatcacgt gacacgtcca agaaccagtt ctccctgaag        300
ctgagctctg tgaccgctgt ggacactgca gtgtattact gtgcgagaaa agatccgtcc        360
gacgcctttc cttactgggg ccaagggact ctggtcactg tctcttccgc tccaccaag         420 ggcccatcgg tcttccccct ggcaccctcc tccaagagca cctctggggg cacagcggcc        480
ctgggctgcc tggtcaagga ctacttcccc gaaccggtga cagtctcgtg gaactcagga        540
gccctgacca gcggcgtgca caccttcccg gctgtcctac agtcctcagg actctactcc        600
ctcagcagcg tggtgactgt gccctccagc agcttgggca cccagaccta catctgcaac        660
gtgaatcaca agcccagcaa caccaaggtg gacaagagag ttgagcccaa atcttgtgac        720
aaaactcaca catgcccacc gtgcccagca cctgaactcc tggggggacc gtcagtcttc        780
ctcttccccc caaaacccaa ggacaccctc atgatctccc ggacccctga ggtcacatgc        840
gtggtggtgg acgtgagcca cgaagaccct gaggtcaagt tcaactggta cgtggacggc        900
gtggaggtgc ataatgccaa gacaaagccg cgggaggagc agtacaacag cacgtaccgt        960
gtggtcagcg tcctcaccgt cctgcaccag gactggctga atggcaagga gtacaagtgc       1020
aaggtctcca acaaagccct cccagccccc atcgagaaaa ccatctccaa agccaaaggg       1080
cagccccgag aaccacaggt gtataccctg cccccatctc gggaggagat gaccaagaac       1140
caggtcagcc tgacttgcct ggtcaaaggc ttctatccca gcgacatcgc cgtggagtgg       1200
gagagcaacg ggcagccgga gaacaactac aagaccacgc ctcccgtgct ggactccgac       1260
ggctccttct tcctctatag caagctcacc gtggacaagt ccaggtggca gcagggggaac      1320 gtcttctcat gctccgtgat gcatgaggct ctgcacaacc actacacgca gaagagcctc       1380
tccctgtctc cgggttaa                                                     1398
```

<210> SEQ ID NO 182
<211> LENGTH: 214
<212> TYPE: PRT
<213> ORGANISM: Artificial Sequence
<220> FEATURE:
<223> OTHER INFORMATION: 1E11.C1 IgG1 formatted anti-TLR4 light chain

<400> SEQUENCE: 182

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 446
<212> TYPE: PRT
<213> ORGANISM: Artificial Sequence
<220> FEATURE:
<223> OTHER INFORMATION: 1E11.C1 IgG1 formatted anti-TLR4 heavy chain

<400> SEQUENCE: 183

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Leu Lys
    50                  55                  60

Thr Arg Ile Thr Ile Ser Arg Asp Thr Ser Lys Asn Gln Phe Ser Leu
65                  70                  75                  80

Lys Leu Ser Ser Val Thr Ala Val Asp Thr Ala Val Tyr Tyr Cys Ala

```
                         85                   90                    95
Arg Lys Asp Ser Gly Asn Tyr Phe Pro Tyr Trp Gly Gln Gly Thr Leu
                    100                  105                 110

Val Thr Val Ser Ser Ala Ser Thr Lys Gly Pro Ser Val Phe Pro Leu
                115                  120                 125

Ala Pro Ser Ser Lys Ser Thr Ser Gly Gly Thr Ala Ala Leu Gly Cys
            130                  135                 140

Leu Val Lys Asp Tyr Phe Pro Glu Pro Val Thr Val Ser Trp Asn Ser
145                 150                  155                 160

Gly Ala Leu Thr Ser Gly Val His Thr Phe Pro Ala Val Leu Gln Ser
                165                  170                 175

Ser Gly Leu Tyr Ser Leu Ser Ser Val Val Thr Val Pro Ser Ser Ser
                180                  185                 190

Leu Gly Thr Gln Thr Tyr Ile Cys Asn Val Asn His Lys Pro Ser Asn
                195                  200                 205

Thr Lys Val Asp Lys Arg Val Glu Pro Lys Ser Cys Asp Lys Thr His
                210                  215                 220

Thr Cys Pro Pro Cys Pro Ala Pro Glu Leu Leu Gly Gly Pro Ser Val
225                 230                  235                 240

Phe Leu Phe Pro Pro Lys Pro Lys Asp Thr Leu Met Ile Ser Arg Thr
                245                  250                 255

Pro Glu Val Thr Cys Val Val Val Asp Val Ser His Glu Asp Pro Glu
                260                  265                 270

Val Lys Phe Asn Trp Tyr Val Asp Gly Val Glu Val His Asn Ala Lys
                275                  280                 285

Thr Lys Pro Arg Glu Glu Gln Tyr Asn Ser Thr Tyr Arg Val Val Ser
            290                  295                 300

Val Leu Thr Val Leu His Gln Asp Trp Leu Asn Gly Lys Glu Tyr Lys
305                 310                  315                 320

Cys Lys Val Ser Asn Lys Ala Leu Pro Ala Pro Ile Glu Lys Thr Ile
                325                  330                 335

Ser Lys Ala Lys Gly Gln Pro Arg Glu Pro Gln Val Tyr Thr Leu Pro
                340                  345                 350

Pro Ser Arg Glu Glu Met Thr Lys Asn Gln Val Ser Leu Thr Cys Leu
            355                  360                 365

Val Lys Gly Phe Tyr Pro Ser Asp Ile Ala Val Glu Trp Glu Ser Asn
                370                  375                 380

Gly Gln Pro Glu Asn Asn Tyr Lys Thr Thr Pro Pro Val Leu Asp Ser
385                 390                  395                 400

Asp Gly Ser Phe Phe Leu Tyr Ser Lys Leu Thr Val Asp Lys Ser Arg
                405                  410                 415

Trp Gln Gln Gly Asn Val Phe Ser Cys Ser Val Met His Glu Ala Leu
                420                  425                 430

His Asn His Tyr Thr Gln Lys Ser Leu Ser Leu Ser Pro Gly
                435                  440                 445

<210> SEQ ID NO 184
<211> LENGTH: 705
<212> TYPE: DNA
<213> ORGANISM: Artificial Sequence
<220> FEATURE:
<223> OTHER INFORMATION: 1E11.C1 IgG1 formatted anti-TLR4 light chain

<400> SEQUENCE: 184
atgagtgtgc ccactcaggt cctggggttg ctgctgctgt ggcttacaga tgccagatgt     60
```

```
gaaattgtgt tgacgcagtc tccagacttt cagtctgtga ctccaaagga aaaagtcacc    120
atcacctgca gggccagtca gagtatcagc gaccacttac actggtacca acagaaacct    180
gatcagtctc ccaagctcct catcaaatat gcttcccatg ccatttctgg ggtcccatcg    240
aggttcagtg gcagtgggtc tgggacagac ttcactctca ccatcaatag cctagaggct    300
gaagatgctg caacgtatta ctgtcagcag ggtcacagtt tccgctcac tttcggcgga    360 gggaccaagg tggagatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttaa                    705

<210> SEQ ID NO 185
<211> LENGTH: 1398
<212> TYPE: DNA
<213> ORGANISM: Artificial Sequence
<220> FEATURE:
<223> OTHER INFORMATION: 1E11.C1 IgG1 formatted anti-TLR4 heavy chain

<400> SEQUENCE: 185
atggaatgga gctgggtctt tctcttcttc ctgtcagtaa ctacaggtgt ccaccaggtg    60
cagcttcagg agtccggccc aggactggtg aagccttcgg acaccctgtc cctcacctgc    120
gctgtctctg gtttcccgat ccgctacggg tatagctggc actggatacg cagcccccca    180
gggaagggac tggagtggat ggggtatatc cactacagtg gttacactga cttcaacccc    240
tccctcaaga ctcgaatcac catatcacgt gacacgtcca agaaccagtt ctccctgaag    300
ctgagctctg tgaccgctgt ggacactgca gtgtattact gtgcgagaaa agattcgggc    360
aactacttcc cttactgggg ccaagggact ctggtcactg tctcttccgc ctccaccaag    420
ggcccatcgg tcttccccct ggcaccctcc tccaagagca cctctggggg cacagcggcc    480
ctgggctgcc tggtcaagga ctacttcccc gaaccggtga cagtctcgtg gaactcagga    540
gccctgacca gcggcgtgca caccttcccg gctgtcctac agtcctcagg actctactcc    600
ctcagcagcg tggtgactgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaagggg    1080
cagccccgag aaccacaggt gtataccctg cccccatctc gggaggagat gaccaagaac    1140
caggtcagcc tgacttgcct ggtcaaaggc ttctatccca gcgacatcgc cgtggagtgg    1200
gagagcaacg ggcagccgga gaacaactac aagaccacgc ctcccgtgct ggactccgac    1260
```

```
ggctccttct tcctctatag caagctcacc gtggacaagt ccaggtggca gcaggggaac    1320
gtcttctcat gctccgtgat gcatgaggct ctgcacaacc actacacgca gaagagcctc    1380
tccctgtctc cgggttaa                                                  1398
```